United States Patent
Ganguly et al.

(10) Patent No.: US 7,115,578 B2
(45) Date of Patent: *Oct. 3, 2006

(54) RIBAVIRIN-INTERFERON ALFA COMBINATION THERAPY FOR ERADICATING DETECTABLE HCV-RNA IN PATIENTS HAVING CHRONIC HEPATITIS C INFECTION

(75) Inventors: Ashit K. Ganguly, Upper Montclair, NJ (US); Jinping McCormick, Edison, NJ (US); Raymond G. Lovey, West Caldwell, NJ (US); Frank Bennett, Cranford, NJ (US); Anil K. Saksena, Upper Montclair, NJ (US); Viyyoor M. Girijavallabhan, Parsippany, NJ (US)

(73) Assignee: Schering Corporation, Kenilworth, NJ (US)

( * ) Notice: Subject to any disclaimer, the term of this patent is extended or adjusted under 35 U.S.C. 154(b) by 29 days.

This patent is subject to a terminal disclaimer.

(21) Appl. No.: 10/885,374

(22) Filed: Jul. 6, 2004

(65) Prior Publication Data

US 2005/0004053 A1 Jan. 6, 2005

Related U.S. Application Data

(62) Division of application No. 09/837,491, filed on Apr. 18, 2001, now Pat. No. 6,924,270.

(60) Provisional application No. 60/198,801, filed on Apr. 20, 2000.

(51) Int. Cl.
*A01N 43/04* (2006.01)
*A61K 31/70* (2006.01)

(52) U.S. Cl. .............................. 514/43; 514/2; 514/21; 514/894; 424/85.7; 424/85.4; 530/351

(58) Field of Classification Search ............... 514/2, 514/21, 43, 894; 536/28.6, 28.7; 424/85.7, 424/85.4; 530/351
See application file for complete search history.

(56) References Cited

U.S. PATENT DOCUMENTS

| 3,984,396 | A |   | 10/1976 | Witkowski et al. |
| 4,211,771 | A | * | 7/1980  | Witkowski et al. |
| 4,925,930 | A |   | 5/1990  | Robins et al. |
| 5,503,828 | A | * | 4/1996  | Testa et al. |
| 6,277,830 | B1 |  | 8/2001  | Ganguly et al. |
| 6,403,564 | B1 | * | 6/2002 | Ganguly et al. ............... 514/43 |
| 6,673,775 | B1 |  | 1/2004  | Ganguly et al. |

FOREIGN PATENT DOCUMENTS

| DE | 25 11 828 |   | 10/1975 |
| EP | 0 090 405 |   | 10/1983 |
| EP | 0707855   | * | 12/1995 |
| EP | 0 707 855 |   | 4/1996 |
| EP | 0 809 996 |   | 12/1997 |
| WO | WO 94/22887 |   | 10/1994 |
| WO | WO 96/04924 |   | 2/1996 |
| WO | WO 97/04796 |   | 2/1997 |
| WO | WO 97/21452 |   | 6/1997 |
| WO | WO 98/21223 |   | 5/1998 |
| WO | WO 00/23454 |   | 4/2000 |
| WO | WO 00/23455 |   | 4/2000 |
| WO | WO 01/81359 |   | 4/2000 |

OTHER PUBLICATIONS

Brissot, "Traitement de l'hépatite chronique C par les associations thérapeutiques," *Gastroenterolog Clin Biol*, 20(1; Pt 2):S89-S95 (1997).
Drabikowska et al., "Studies on the mechanism of antiviral action of 1-(beta-D-ribofuranosyl)-1,2,4-triazole-3-carboxamide (ribavirin)," *J Med Chem*, 22(6):653-657 (1979).
Allen et al., "Synthesis and antiviral activity of some phosphates of the broad-spectrum antiviral nucleoside, 1-beta-D-ribofuranosyl-1,2,4-triazole-3-carboxamide (ribavirin)," *J Med Chem*, 21(8):742-746 (1978).
Kini et al., "Synthesis and antitumor activity of Ribavirin imidates. A new facile synthesis of ribavirin amidine (1-beta-D-ribofuranosyl-1,2,4-triazole-3-carboxamidine hydrochloride)," *J Med Chem*, 32(7):1447-1449 (1989).
Davis et al., "Interferon alfa-2b alone or in combination with ribavirin for the treatment of relapse of chronic hepatitis C," *N Engl J Med*, 339(21):1493-1499 (1998).
McHutchinson et al., "Interferon alfa-2b alone or in combination with ribavirin as initial treatment for chronic hepatitis C," *N Engl J Med*, 339(21):1485-1492 (1998).

(Continued)

*Primary Examiner*—Patrick Lewis
(74) *Attorney, Agent, or Firm*—Melodie W. Henderson

(57) ABSTRACT

Ribavirin derivatives represented by the formula V, pharmaceutical compositions containing them as well as the use of the ribavirin derivatives represented by the formula V for the preparation of a medicament for the treatment of susceptible viral infections, for example, chronic hepatitis C infections administrating, the ribavirin derivatives being represented by formula V

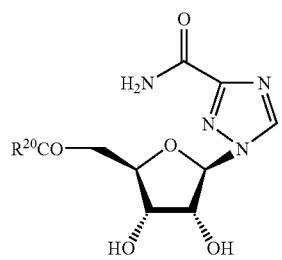

are disclosed.

7 Claims, No Drawings

OTHER PUBLICATIONS

Poynard et al., "Randomised trial of interferon alpha-2b plus ribavirin for 48 weeks or for 24 weeks versus interferon alpha2b plus placebo for 48 weeks for treatment of chronic infection with hepatitis C virus," *Lancet*, 352(9138):1426-1432 (1998).

Reichard et al., "Randomised, double-blind, placebo-controlled trial of interferon alpha-2b with and without ribavirin for chronic hepatitis C," *Lancet*, 351:83-87 (1998).

Zakharieva et al., "Synthesis and antiviral activity of amino acid esters of ribavirin," *Bioorganic Med Chem*, 4(24):2831-2832 (1994).

* cited by examiner

RIBAVIRIN-INTERFERON ALFA COMBINATION THERAPY FOR ERADICATING DETECTABLE HCV-RNA IN PATIENTS HAVING CHRONIC HEPATITIS C INFECTION

This application is a divisional application of U.S. Ser. No. 09/837,491, filed Apr. 18, 2001 now U.S. Pat. No. 6,942,270, now allowed which claims the benefit of U.S. Ser. No. 60/198,801 filed Apr. 20, 2000.

All references cited herein are incorporated in their entirety by reference.

BACKGROUND OF THE INVENTION

The present invention relates to ribavirin derivatives represented by the formula II, pharmaceutical compositions containing them as well as the use of the ribavirin derivatives represented by the formula II for the preparation of a medicament for the treatment of susceptible viral infections, for example, chronic hepatitis C infections administrating, the ribavirin derivatives being represented by formula II

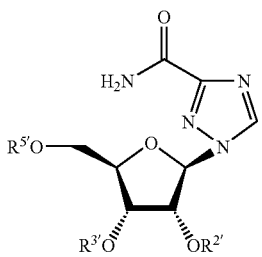

II

Chronic infection with hepatitis C virus is an insidious and slow-progressing disease having a significant impact on the quality of life. It can eventually result in cirrhosis of the liver, decompensated liver disease and/or hepatocelluar carcinoma.

Combination treatment with interferon alfa-2b and ribavirin of patients with chronic hepatitis C is disclosed by Reichard et al. (The Lancet 1998; 351;83–87; and T. Poynard et al. (The Lancet, 1998, Vol. 352, October 31, p 1426–1432). See also J. G. McHutchinson et al. (N. Engl. J. Med., 1998, 339:1485–1492); and G. L. Davis et al. (N. Engl. J. Med., 1998, 339:1493–1499). However, this combination therapy is not always effective due to side effects associated ribavirin such as ribavirin-related hemolysis, and anemia.

There is a definite need for more potent, safer ribavirin derivatives having fewer side effects for use as monotherapy or in combination with antiviral agents, e.g., interferon-alpha, to treat patients having susceptible viral infections, e.g., chronic hepatitis C infections, in a long-term, effective manner.

SUMMARY OF THE INVENTION

The present invention provides a method of treating patients having chronic hepatitis C infection comprising administering a therapeutically effective amount of a ribavirin derivative of formula I and a therapeutically effective amount of interferon-alpha for a time period sufficient to eradicate detectable HCV-RNA at the end of said period of administering and to have no detectable HCV-RNA for at least 24 weeks after the end of said period of administrating, and wherein the ribavirin derivative is represented by formula I:

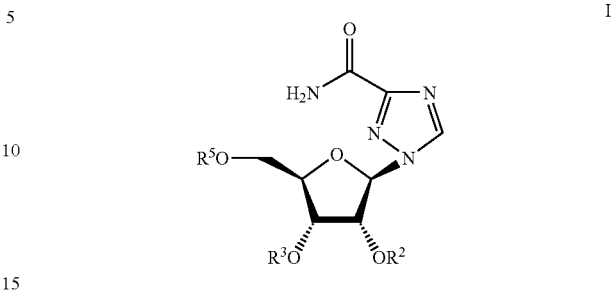

I wherein at least one of $R^2$, $R^3$ or $R^5$ is H, $R^6$—$(W)_x$—CO—, $R^6$—$(W)_x$—CS—$(HO)_2PO$—, $R^6$—$(W)_x$—PO(OH)— or HO—$SO_2$— and wherein at least one of $R^2$, $R^3$ or $R^5$ is not H;

wherein $R^6$ is H, alkyl, alkanoyl, cycloalkyl, heterocylic, aryl, $NR^{7a}R^{7b}$, alkenyl, or alkynyl; or is alkyl, alkanoyl, alkenyl or alkynyl substituted by halo, phenyl, cycloalkyl, $NR^{7a}R^{7b}$, hydroxy or alkoxy;

or $R^6$ is aryl substituted by phenyl, halo, CN, $NO_2$, OH, $R^{18}$, $OR^{18}$, $CF_3$, SH $SR^{7a}$, $SOR^{7a}$, $SO_2R^{7a}$; $NR^{7a}R^{7b}CO_2H$, $CO_2^-M^{+-}$, $O^-M^+OR^{7a}$ or $S^-M^+$;

wherein $M^+$ is an alkali metal cation;

or $R^6$ is —$(CHR^{7a})_e$—$(CH_2)_f$—CO—$OR^{7b}$, —$(CHR^{7a})_e$—$(CH_2)_f$—$OR^{7b}$, or —$(CHR^{7a})_e$—$(CH_2)_f$—$NR^{7a}R^{7b}$

W is O, $NR^{18}$ or S;

$R^{7a}$ is H, alkyl, alkanoyl, aryl or is alkyl, alkanoyl or aryl substituted by halo phenyl CN, $NO_2$, OH, $CO_2H$ or alkoxy; and $R^{7b}$ is H, alkyl or aryl or is alkyl or aryl substituted by halo, CN, $NO_2$, $CO_2H$, OH or alkoxy;

or $R^{7a}$ and $R^{7b}$ taken together with N and one of $CHR^{7a}$, $NR^{7a}$, O, S, SO or $SO_2$ form a five-, six- or seven-membered ring;

$R^{17}$ is H, $OR^{7a}$, $NR^{7a}R^{7b}$, $R^6$—$(W)_x$—CO—, $R^6$—$(W)_x$—CS—, $(HO)_2PO$—, $R^6$—$(W)_x$—PO(OH)—, or HO—$SO_2$—;

$R^{18}$ is H, aryl, alkyl, or alkyl substituted by OH, halo, $NR^{7a}R^{7b}$, or alkanoyl;

e=0 to 6, f=0 to 10, and x=0 or 1;

or a pharmaceutically acceptable salt thereof.

Preferably $R^5$ is $R^6CO$ wherein $R^6$ is aryl substituted by phenyl, halo, CN, $NO_2$, OH, $R^{18}$, $OR^{18}$, $CF_3$, SH $SR^{7a}$, $SOR^{7a}$, $SO_2R^{7a}$; $NR^{7a}R^{7b}CO_2H$, $CO_2^-M^{+-}$, $O^-M^+OR^{7a}$ or $S^-M^+$, wherein $M^+$ is an alkali metal cation.

More preferably $R^5$ is $R^6CO$ wherein $R^6$ is phenyl substituted by, halo, CN, $NO_2$, OH, $R^{18}$, $OR^{18}$, $CF_3$, SH $SR^{7a}$, $SOR^{7a}$, $SO_2R^{7a}$; $NR^{7a}R^{7b}CO_2H$, $CO_2^-M^{+-}$, $O^-M^+OR^{7a}$ or $S^-M^+$, wherein $M^+$ is an alkali metal cation.

The present invention also provides ribavirin derivatives is represented by the formula II, pharmaceutical compositions containing them as well as the use of the ribavirin derivatives represented by the formula II for the preparation of a medicament for the treatment of susceptible viral infections, for example chronic hepatitis C infections; wherein the pharmaceutical compositions comprising a therapeutically effective amount of a ribavirin derivative of formula I and a therapeutically effective amount of interferon-alpha, and wherein the treatment being for a time period of at least 20 to 50 weeks to eradicate detectable HCV-RNA at the end of said 20 to 50 week period of treatment and to have no detectable HCV-RNA for at least 24 weeks after the end of said period of treatment, and wherein the ribavirin derivatives are represented by the formula II:

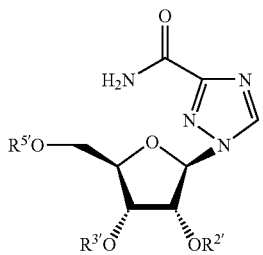

wherein at least one of $R^2$, $R^3$ or $R^5$ is H, $R^6$—$(W)_x$—CO—, $R^6$—$(W)_x$—CS—$(HO)_2PO$—, $R^6$—$(W)_x$—PO(OH)— or HO—$SO_2$— and wherein at least one of $R^2$, $R^3$ or $R^5$ is not H;

wherein $R^6$ is H, alkyl, alkanoyl, cycloalkyl, aryl, heterocyclic, $NR^{7a}R^{7b}$, alkenyl, or alkynyl;

or is alkyl, alkanoyl, alkenyl or alkynyl substituted by halo, phenyl, cycloalkyl, $NR^{7a}R^{7b}$, hydroxy, alkoxy;

or is aryl substituted by phenyl, halo, CN, $NO_2$, OH, $R^{18}$, $OR^{18}$, $CF_3$, SH, $SR^{7a}$, $SOR^{7a}$, $SO_2R^{7a}$; $NR^{7a}R^{7b}CO_2H$, $CO_2^-$, $OR^{7a}$, $O^-M^+$; or $S^-M^+$;

wherein $M^+$ is an alkali metal cation;

or $R^6$ is —$(CHR^{7a})_e$—$(CH_2)_f$—CO—$OR^{7b}$, —$(CHR^{7a})_e$—$(CH_2)_f$—$OR^{7b}$, or —$(CHR^{7a})_e$—$(CH_2)_f$—$NR^{7a}R^{7b}$

W is O, $NR^{18}$ or S;

$R^{7a}$ is H, alkyl, alkanoyl, or aryl is alky, alkanoyll or aryl substituted by halo, CN, $NO_2$, OH, $CO_2H$ or alkoxy;

and $R^{7b}$ is H, alkyl or aryl or is alkyl or aryl substituted by halo, CN, $NO_2$, OH, $CO_2H$ or alkoxy;

or $R^{7a}$ and $R^{7b}$ taken together with N and one of $CHR^{7a}$, $NR^{7a}$, O, S, SO or $SO_2$ form a five-, six- or seven-membered ring;

$R^{17}$ is H, $OR^{7a}$, $NR^{7a}R^{7b}$, $R_6$—$(W)_x$—CO—, $R^6$—$(W)_x$—CS—, $(HO)_2PO$—, $R^6$—$(W)_x$—PO(OH)— or HO—$SO_2$—;

$R^{18}$ is H, aryl, alkyl, or alkyl substituted by OH, halo, $NR^{7a}R^{7b}$, or alkanoyl;

e=0 to 6, f=0 to 10, and x=0 or 1;

or a pharmaceutically acceptable salt thereof.

Preferably $R^5$ is $R^6CO$ wherein $R^6$ is aryl substituted by phenyl, halo, CN, $NO_2$, OH, $R^{18}$, $OR^{18}$, $CF_3$, SH $SR^{7a}$, $SOR^{7a}$, $SO_2R^{7a}$; $NR^{7a}R^{7b}$ $CO_2H$, $CO_2^-M^{+-}$, $O^-M^+OR^{7a}$ or $S^-M^+$, wherein $M^+$ is an alkali metal cation.

More preferably $R^5$ is $R^6CO$ wherein $R^6$ is phenyl substituted by, halo, CN, $NO_2$, OH, $R^{18}$, $OR^8$, $CF_3$, SH $SR^{7a}$, $SOR^{7a}$, $SO_2R^{7a}$; $NR^{7a}R^{7b}$ $CO_2H$, $CO_2^-M^{+-}$, $O^-M^+OR^{7a}$ or $S^-M^+$, wherein $M^+$ is an alkali metal cation.

In another embodiment, the present invention relates to a compound represented by formula II

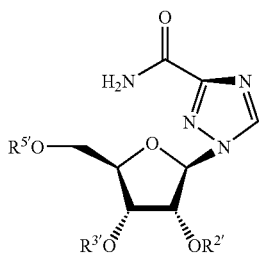

wherein at least one of $R^{2'}$, $R^{3'}$ or $R^{5'}$ is H, $R^{20}$—$(W)_x$—CO—, $R^{20}$—$(W)_x$—CS— or $R^{20}$—$(W)_x$—PO(OH)—; and wherein at least one of $R^{2'}$, $R^{3'}$ or $R^{5'}$ is not H;

wherein $R^{20}$ is H, alkyl, alkanoyl, cycloalkyl, aryl, heterocyclic, $NR^{21}R^{22}$, alkenyl, or alkynyl;

or is alkyl, alkanoyl alkenyl or alkynyl substituted by halogen, phenyl, cycloalkyl, $NR^{21}R^{22}$, hydroxy, alkoxy;

or $R^{20}$ is aryl substituted by halogen, phenyl, CN, $NO_2$, OH, $R^{28}$, $OR^{28}$, $CF_3$, SH, $SR^{21}$ $SOR^{21}$, $SO_2R^{21}$; $NR^{21}R^{22}$, $CO_2H$, $CO_2^-$—, $OR^{21}$, $O^-M^+$ or $S^-M^+$;

wherein $M^+$ is an alkali metal cation;

or $R^{20}$ is —$(CHR^{21})_e$—$(CH_2)_f$—CO—$OR^{22}$, —$(CHR^{21})_e$—$(CH_2)_f$—$OR^{22}$, or —$(CHR^{21})_e$—$(CH_2)_f$—$NR^{21}R^{22}$

W is O, $NR^{28}$ or S;

$R^{21}$ is H, alkyl, alkanoyl, or aryl, or is alkyl, alkanoyl or aryl substituted by halo, phenyl, CN, $NO_2$ OH, $CO_2H$ or alkoxy; and $R^{22}$ is H, alkyl or aryl or is alkyl or aryl substituted by halo, phenyl, CN, $NO_2$, OH, $CO_2H$ or alkoxy;

or $R^{21}$ and $R^{22}$ taken together with N and one of $CHR^{21}$, $NR^{21}$, O, S, SO or $SO_2$ form a five-, six- or seven-membered ring;

$R^{27}$ is H, $OR^{21}$, $NR^{21}R^{22}$, $R^{20}$—$(W)_x$—CO—, $R^{20}$—$(W)_x$—CS—, $(OH)_2PO$—, $R^{20}$—$(W)_x$—PO(OH)— or HO—$SO_2$—;

$R^{28}$ is H, aryl, alkyl, or alkyl substituted by OH, halo, $NR^{21}R^{22}$, or alkanoyl;

e=0 to 6, f=0 to 10; and x=0 or 1;

or a pharmaceutically acceptable salt thereof.

Preferably $R^{5'}$ is $R^{20}CO$ wherein $R^{20}$ is aryl substituted by halogen, phenyl, CN, $NO_2$, OH, $R^{28}$, $OR^{28}$, $CF_3$, SH, $SR^{21}$ $SOR^{21}$, $SO_2R^{21}$; $NR^{21}R^{22}$, $CO_2H$, $CO_2^-$—, $OR^{21}$, $O^-M^+$ or $S^-M^+$;

wherein $M^+$ is an alkali metal cation.

More preferably $R^{5'}$ is $R^{20}CO$ wherein $R^{20}$ is phenyl substituted by halogen, CN, $NO_2$, OH, $R^{28}$, $OR^{28}$, $CF_3$, SH, $SR^{21}$ $SOR^{21}$, $SO_2R^{21}$; $NR^{21}R^{22}$; $CO_2H$, $CO_2^-$—, $OR^{21}$, $O^-M^+$ or $S^-M^+$;

wherein $M^+$ is an alkali metal cation.

In another embodiment, the present invention relates to a method of treating patients having chronic hepatitis C infection comprising administering a therapeutically effective amount of a ribavirin derivative of formula II and a therapeutically effective amount of interferon-alpha for a time period sufficient to eradicate detectable HCV-RNA at the end of said period of administering and to have no detectable HCV-RNA for at least 24 weeks after the end of said period of administrating, and wherein the ribavirin derivative is represented by formula II

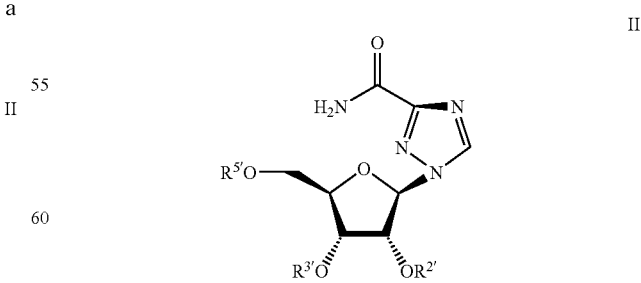

wherein at least one of $R^{2'}$, $R^{3'}$ or $R^{5'}$ is H, $R^{20}$—$(W)_x$—CO—, $R^{20}$—$(W)_x$—CS— or $R^{20}$—$(W)_x$—PO(OH)—; and wherein at least one of $R^2$, $R^3$ or $R^5$ is not H;

wherein $R^{20}$ is H, alkyl, alkanoyl, cycloalkyl, aryl, heterocyclic, $NR^{21}R^{22}$, alkenyl, or alkynyl;

or is alkyl, alkanoyl alkenyl or alkynyl substituted by halo, phenyl, cycloalkyl, $NR^{21}R^{22}$, hydroxy, alkoxy;

or $R^{20}$ is aryl substituted by phenyl, halo, CN, $NO_2$, OH, $R^{28}$, $OR^{28}$, $CF_3$, SH, $SR^{212}$, $SOR^{21}$, $SO_2R^1$; $NR^{21}R^{22}CO_2H$, $CO_2^-$—, $OR^{21}$, $O^-M^+$ or $S^-M^+$;

wherein $M^+$ is an alkali metal cation;

or $R^{20}$ is —$(CHR^{21})_e$—$(CH_2)_f$—CO—$OR^{22}$, —$(CHR^{21})_e$—$(CH_2)_f$—$OR^{22}$, or —$(CHR^{21})_e$—$(CH_2)_f$—$NR^{21}R^{22}$

W is O, $NR^{28}$ or S;

$R^{21}$ is H, alkyl, alkanoyl, or aryl or is alkyl, alkanoyl or aryl substituted by halo, phenyl, CN, $NO_2$, OH, $CO_2H$ or alkoxy; and $R^{22}$ is H, alkyl or aryl or is alkyl or aryl substituted by halo, CN, $NO_2$, OH, $CO_2H$ or alkoxy;

or $R^{21}$ and $R^{22}$ taken together with N and one of $CHR^{21}$, $NR^{21}$, O, S, SO or $SO_2$ form a five-, six- or seven-membered ring;

$R^{27}$ is H, $OR^{21}$, $NR^{21}R^{22}$, $R^{20}$—$(W)_x$—CO—, $R^{20}$—$(W)_x$—CS—, $(HO)_2PO$—, $R^{20}$—$(W)_x$—PO(OH)— or HO—$SO_2$—;

$R^{28}$ is H, aryl, alkyl, or alkyl substituted by OH, halo, $NR^{21}R^{22}$, or alkanoyl;

e=0 to 6, f=0 to 10, and x=0 or 1;

or a pharmaceutically acceptable salt thereof.

Preferably $R^{5'}$ is $R^{20}$ CO wherein $R^{20}$ is aryl substituted by phenyl, halo, CN, $NO_2$, OH, $R^{28}$, $OR^{28}$, $CF_3$, SH, $SR^{212}$, $SOR^{21}$, $SO_2R^{21}$; $NR^{21}R^{22}CO_2H$, $CO_2^-$—, $OR^{21}$, $O^-M^+$ or $S^-M^+$, wherein $M^+$ is an alkali metal cation;

More preferably $R^{5'}$is $R^{20}$ CO $R^{20}$ is phenyl substituted by halo, CN, $NO_2$, OH, $R^{28}$, $OR^{28}$, $CF_3$, SH, $SR^{212}$, $SOR^{21}$, $SO_2R^{21}$; $NR^{21}R^{22}$, $CO_2H$, $CO_2^-$—, $OR^{21}$, $O^-M^+$ or $S^-M^+$, wherein $M^+$ is an alkali metal cation;

The present invention provides a compound represented by formula III

III

[structure diagram]

wherein at least one of $R^{50'}$ $R^{30'}$ or $R^{20'}$ is represented by the formula $$Q-(CR^{51}R^{52})_k-\overset{O}{\underset{\|}{C}}-$$

wherein the other two of $R^{50'}$ $R^{30'}$ or $R^{20'}$ is represented by H or the formula $$Q-(CR^{51}R^{52})_k-\overset{O}{\underset{\|}{C}}-$$

wherein Q is:

$$R^{53}-\underset{R^{56}NR^{55}}{\overset{R^{54}}{C}}-$$

wherein $R^{51}$ and $R^{52}$ are independently H, alkyl, alkenyl, alkynyl, $(C_3-C_7)$cycloalkyl, arylalkyl, or alkyl, alkenyl, alkynyl, $(C_3-C_7)$cycloalkyl, arylalkyl, substituted by halo, OH, SH, $CF_3$, $SR^{57}$, $OR^{57}$ or $NR^{55}R^{56}$ or wherein $R^{51}$ and $R^{52}$ taken together with the carbon atom in $(CR^{51}R^{52})$ form a cyclopropane, cyclobutane, cyclopentane, or cyclohexane;

wherein $R^{53}$ and $R^{54}$ are independently H, alkanoyl, alkyl, aryl, arylalkyl, alkenyl, alkynyl, or alkanoyl, alkyl, aryl, arylalkyl, alkenyl, alkynyl substituted by halo, OH, SH, $CF_3$, $SR^{57}$, $OR^{57}$; or $R^{53}$ and $R^{54}$ are independently

[structure diagrams: pyrrolidine derivative; indolylmethyl; hydroxyphenylmethyl; imidazolylmethyl]

wherein $R^{57}$ is H, alkyl, alkanoyl, alkenoyl, aryl, arylalkyl, alkenyl, alkynyl, or, alkyl, aryl, arylalkyl, alkenyl, alkynyl substituted by halo, OH, SH, $CF_3$, alkanoylthienyl, or alkanoyloxy;

wherein $R^{58}$ is H, alkyl, aryl, arylalkyl, alkenyl, or alkynyl; and q is 0, 1 or 2, and k is 1 or 2;

or a pharmaceutically acceptable salt thereof.

In a preferred embodiment, $R^{30'}$ and $R^{20'}$ in the compounds of Formula III are each H.

The present invention provides a compound represented by the formula IV

IV

[structure diagram]

wherein at least one of $R^{50''}$, $R^{30''}$, $R^{20''}$ is represented by the formula

5 and wherein the other two of $R^{50''}$, $R^{30''}$, $R^{20''}$ is H or is represented by the formula

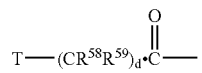

15 wherein T is a moiety represented by the formulas:
$H_2NCH_2-$, $H_2NCH_2CH_2-$, $CH_3CH(H_2N)-$, $CH_3CH_2CH(H_2N)-$, $CH_3(CH_2)_2CH(H_2N)-$, $(CH_3)_2CHCH(H_2N)-$, $(CH_3)_2CHCH_2CH(H_2N)-$, $CH_3CH_2CH(CH_3)CH(H_2N)-$, $PhCH_2CH(H_2N)-$, $HOOCCH_2CH_2CH(H_2N)-$, $HOOCCH_2CH(H_2N)-$, $HSCH_2CH(H_2N)-$, $CH_3SCH_2CH_2CH(H_2N)-$, $HOCH_2CH(H_2N)-$, $H_2N(CH2)_4CH(H_2N)-$, $CH_3CH(OH)CH(H_2N)$,

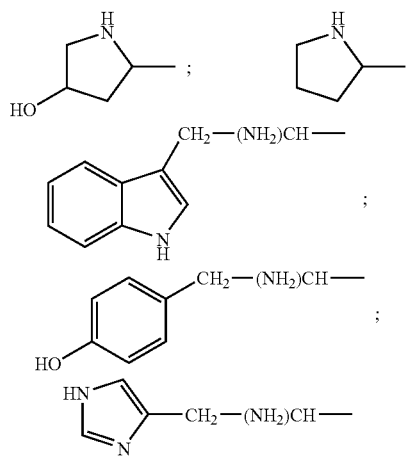

wherein $R^{58}$ and $R^{59}$ are independently H, alkyl, alkenyl, alkynyl, $(C_3-C_7)$cycloalkyl, arylalkyl, or alkyl, alkenyl, alkynyl, $(C_3-C_7)$cycloalkyl, arylalkyl, substituted by halo, OH, SH, $CF_3$, $SR^{60}$, $OR^{60}$ or $NR^{60}R^{61}$ or wherein $R^{58}$ and $R^{59}$ taken together with the carbon atom in $(CR^{58}R^{59})$ form a cyclopropane, cyclobutane, cyclopentane, or cyclohexane.;

wherein $R^{60}$ is H, alkyl, alkanoyl, alkenoyl, aryl, arylalkyl, alkenyl, alkynyl, or, alkyl, aryl, arylalkyl, alkenyl, alkynyl substituted by halo, OH, SH, $CF_3$, alkanoylthienyl, or alkanoyloxy;

wherein $R^{61}$ is H, alkyl, aryl, arylalkyl, alkenyl, or alkynyl;

and d is 0, 1 or 2; or a pharmaceutically acceptable salt thereof.

In a preferred embodiment, $R^{30''}$ and $R^{20''}$ in the compounds of Formula IV are each H.

The present invention provides a compound represented by the formula V

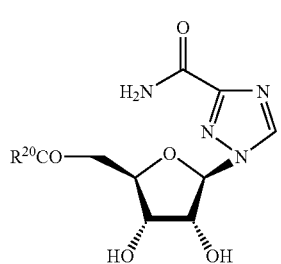

wherein $R^{20}$ C— is a natural or unnatural amino acid moiety represented by the formulas

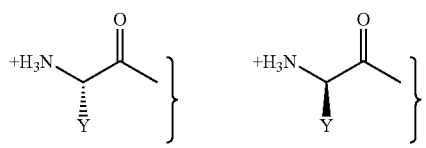

Y=H, $CH_3$; $CH_3CH_2-$; $CH_3CH_2CH_2-$; $Me_2CH-$; $Me_2CH_2CH_2-$; $CH_3CH_2CH(Me)-$ $PhCH_2-$; $HOOCCH_2CH_2-$; $HSCH_2-$; $HOOCCH_2-$; $MeSCH_2CH_2-$; $HOCH_2-$;

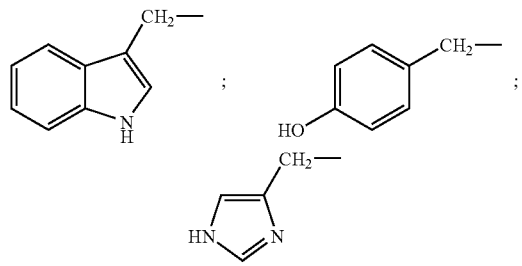

or Y is $H_2N(CH_2)_4-$ or $CH_3CH(OH)-$; or a pharmaceutically acceptable salt thereof; or Y taken together with the α carbon and N form

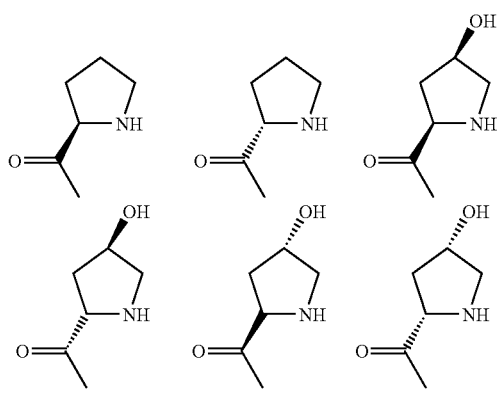

or a pharmaceutically acceptable salt thereof;

or Y taken together with the α carbon and N form
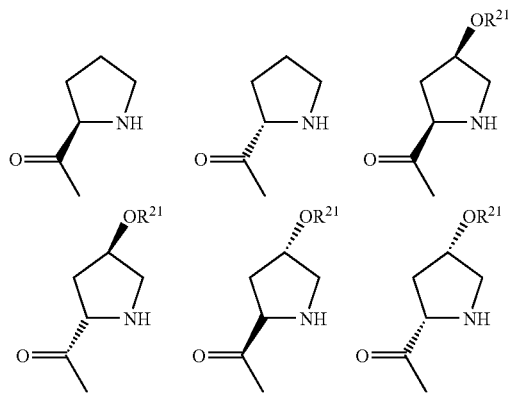
or a phamaceutically acceptable salt thereof.
The present invention provides a compound represented by the formula VI:
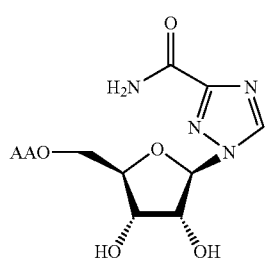
VI
or a pharmaceutically acceptable salt thereof;
wherein AA is a natural or unnatural amino acid moiety of the formula:
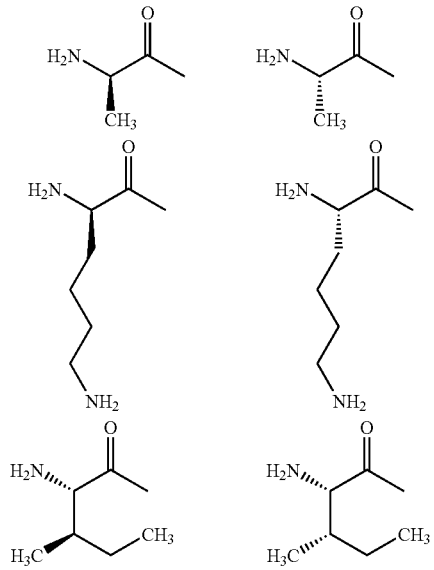
-continued
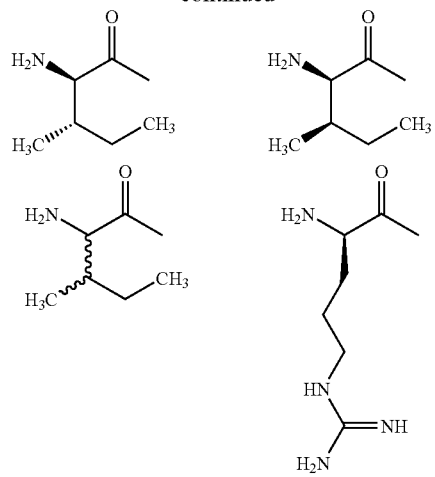
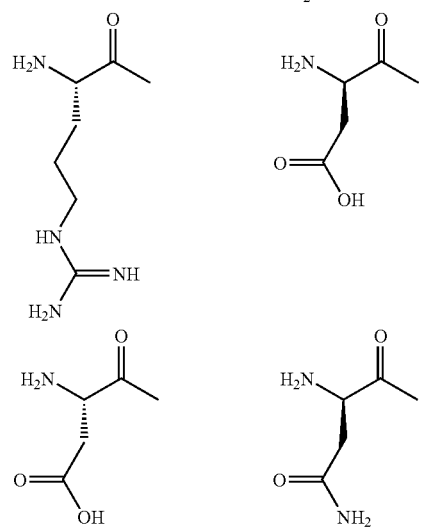
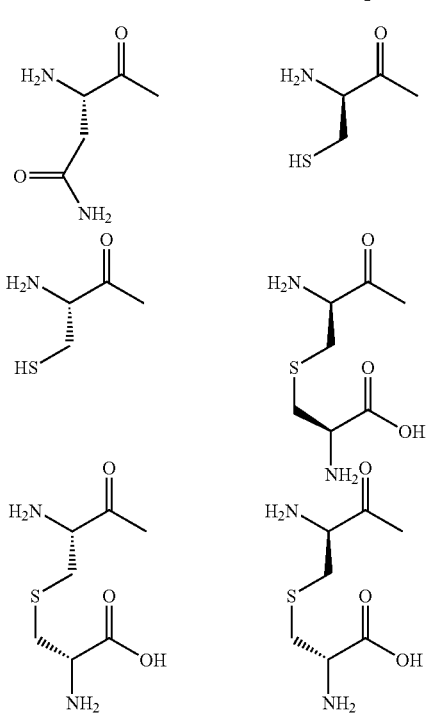

-continued
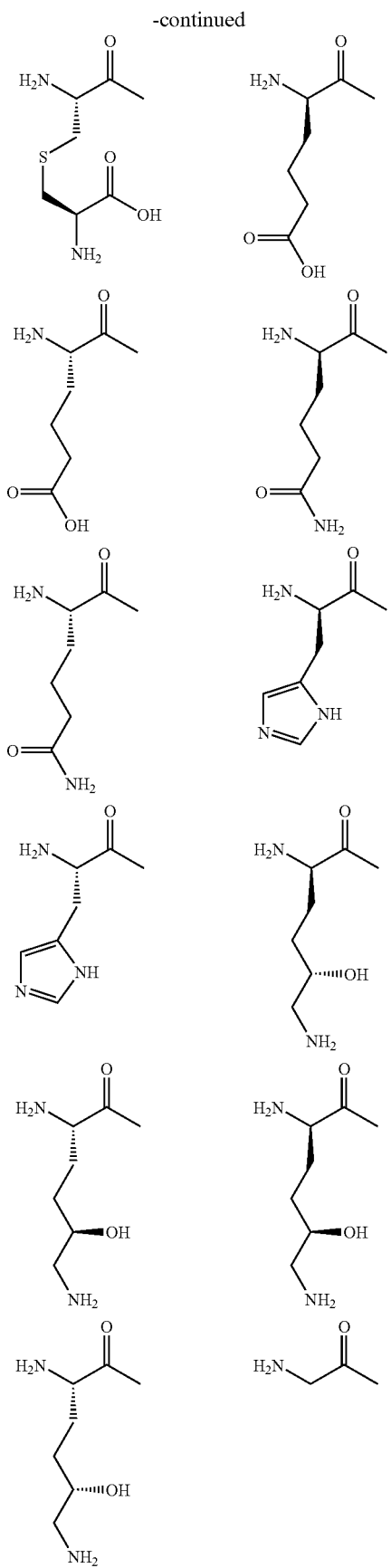
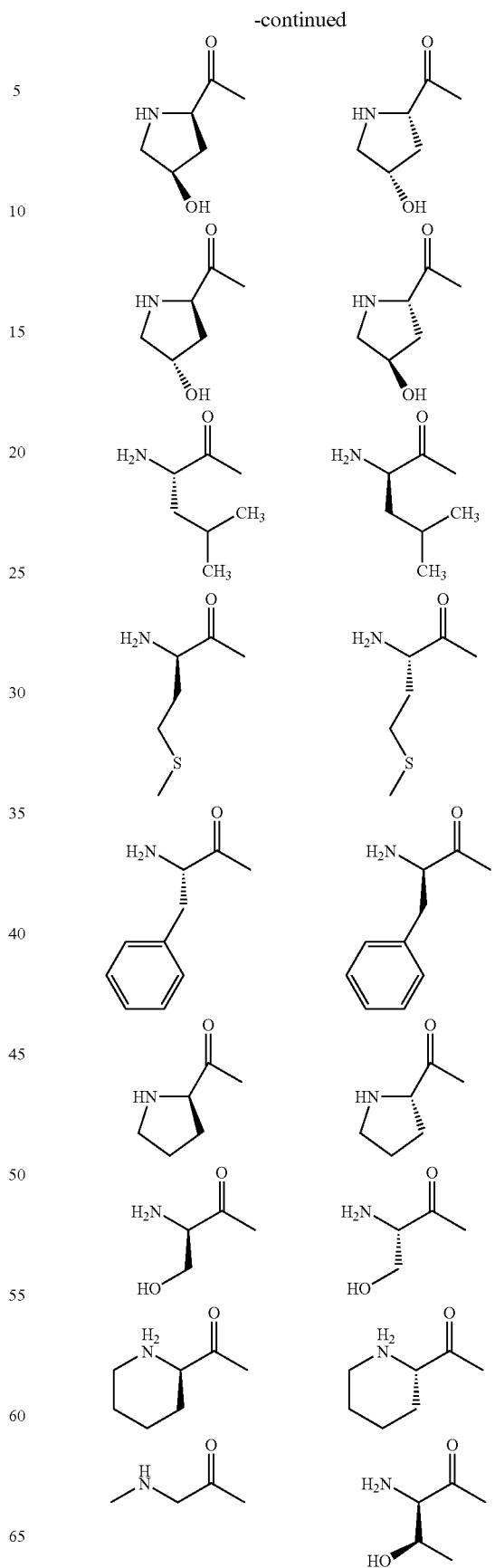

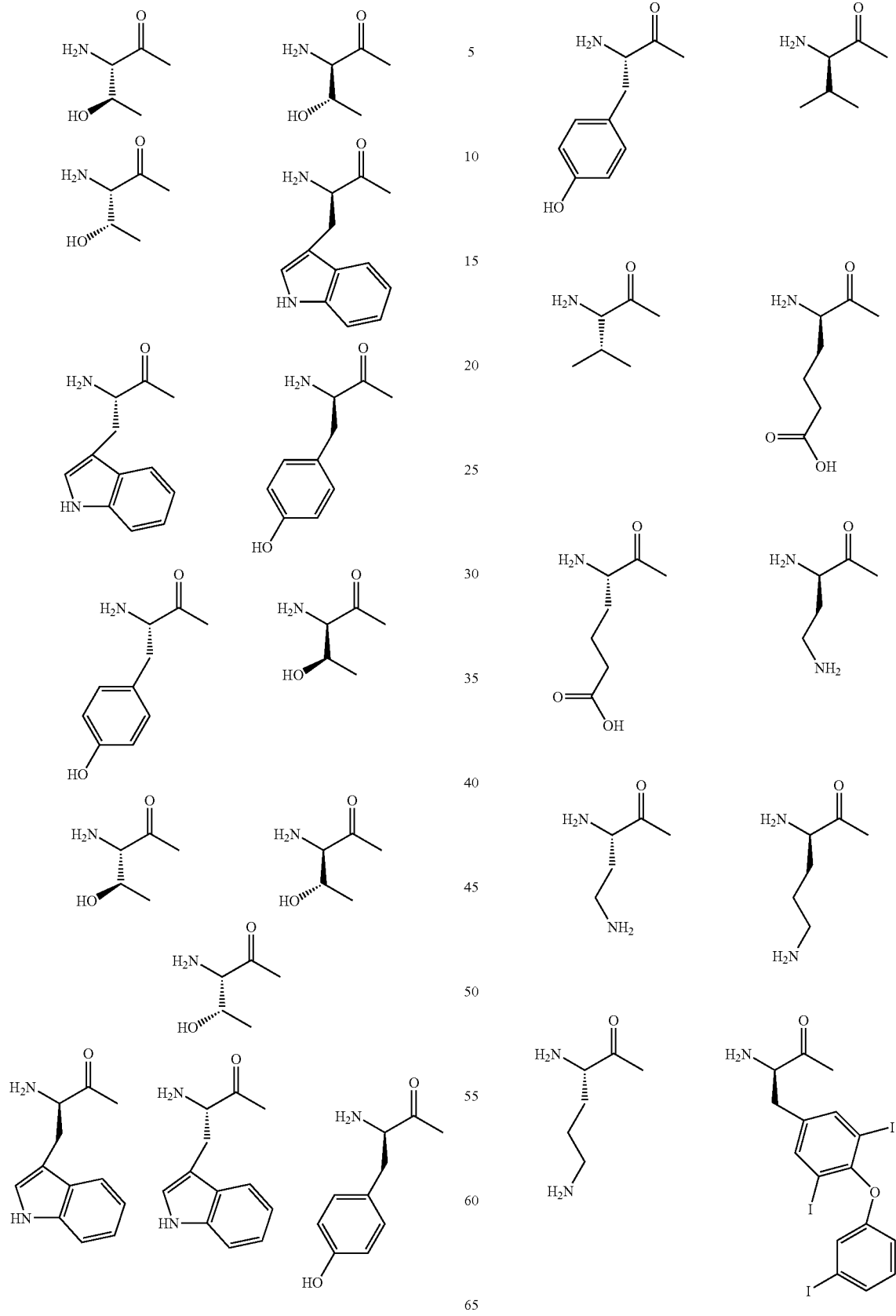

-continued

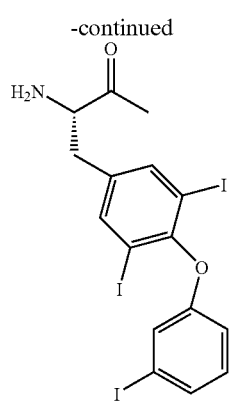

The present invention also provides a compound represented by formula VII

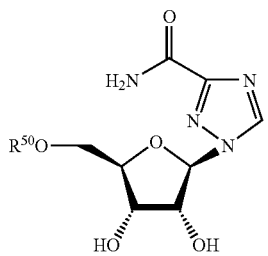
VII wherein $R^{50}$ is $CH_3CH(NH_2)$—CO—, $CH_3CH_2(CH_3)CHCH(NH_2)$—CO— or $H_2N(CH_2)_4CH(NH_2)$—CO—;

or a pharmaceutically acceptable salt thereof.

The present invention also provides pharmaceutical compositions for treating susceptible viral infections comprising a compound of formula VII and at least one pharmaceutically acceptable carrier.

The present invention also provides a method of treating a patient with a susceptible viral infection which comprises administering to said patient an effective amount of a compound of formula VII.

The present invention also provides a method of treating a patient infected with chronic hepatitis C which comprises administering to said patient an effective amount of a compound of formula VII in association with an effective amount of an interferon alfa for a time sufficient to eradicate detectable HCV-RNA levels, wherein the compound represented by the formula VII:

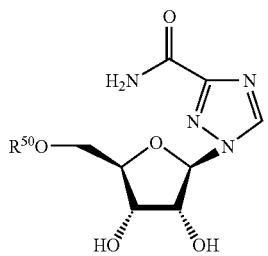
VII wherein $R^{50}$ is $CH_3CH(NH_2)$—CO—, $CH_3CH_2(CH_3)CHCH(NH_2)$—CO— or $H_2N(CH_2)_4CH(NH_2)$—CO—;

or a pharmaceutically acceptable salt thereof.

The present invention provides a compound represented by the formula VIII

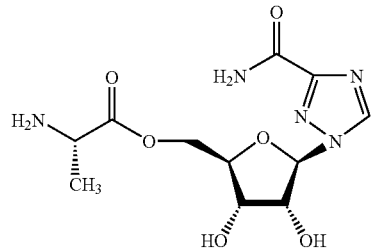
VIII or a pharmaceutically acceptable salt thereof.

The present invention also provides a method of treating a patient infected with chronic hepatitis C which comprises administering to said patient an effective amount of a compound of formula VIII

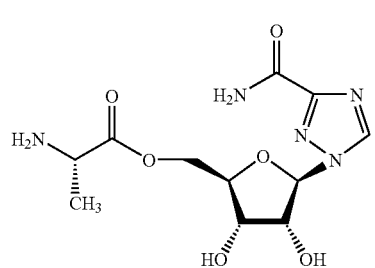
VIII or a pharmaceutically acceptable salt thereof, in association with an effective amount of an interferon alfa for a time sufficient to eradicate detectable HCV-RNA levels.

DETAILED DESCRIPTION

The term "alkyl" as used herein means straight and branched carbon chains of one to twenty carbons, preferably one to six carbons and more preferably one to three carbons.

The term "alkenyl" as used herein means straight and branched chain alkyl groups containing at least one carbon-carbon double bond and two to twenty carbons, preferably two to eight carbons.

The term "alkynyl" as used herein means straight and branched chain alkyl groups containing at least one carbon-carbon triple bond and two to twenty carbons, and preferably two to six carbons containing at least one carbon-carbon triple bond.

The term "cycloalkyl" as used herein means carbocyclic rings of three to twelve carbons, preferably three to seven carbons and more preferably three to six carbons optionally substituted by one double bond.

The term "alkanoyl" as used herein means straight and branched chain alkanoyl groups of one to twenty carbons, preferably two to twelve, more preferably two to ten and most preferably two to six carbons.

The term "alkenoyl" as used herein means straight and branched chain alkenoyl groups of one to twenty carbons containing at least one carbon-carbon double bond, preferably two to twelve, or more preferably two to ten and most preferably two to six carbons containing at least one carbon-carbon double bond.

The term "halo" as used herein means fluoro, chloro or bromo, preferably fluoro or chloro.

The term "alkynoyl" as used herein means straight and branched chain alkenoyl groups of one to twenty carbons containing at least one carbon-carbon triple bond, preferably two to twelve, or more preferably two to ten and most preferably two to six carbons containing at least one carbon-carbon triple bond.

The term "alkoxy" as used herein means straight and branched chain alkyl groups containing one bond to oxygen at the one carbon and one to ten carbons. Typically suitable alkoxy includes methoxy, ethoxy and tert-butoxy.

The term "aryl" as used herein (including the aryl portion of aryloxy and aralkyl, e.g., benzyl)-represents a carbocyclic group containing from 6 to 15 carbon atoms and having at least one aromatic ring (e.g., aryl is a phenyl ring), or is a polycyclic aromatic containing one or more heteroatoms, e.g., N or S such as quinoyl, isoquinolyl with all available substitutable carbon atoms of the carbocyclic group being optionally substituted (e.g., 1 to 3) with one or more of halogen, alkyl, or alkyl substituted by OH, halo, amino diaklylamino, alkanoylamino, or is alkanoyl hydroxy, alkoxy, CN, phenoxy, $CF_3$, amino, alkylamino, dialkylamino, SH, $S^-M^+$ or $-NO_2$; and the term "$M^+$" represents an alkali metal cation such as $Na^+$, $K^+$ and $Li^+$.

The term "arylalkyl" as used herein means an alkyl group substituted by an aryl group.

The term "heterocyclic" as used herein means a cyclic group represented by the formula;

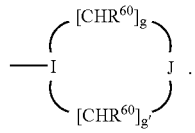

wherein J is $-CHR^{60}-$, $-O-$, $-NR^{60}-$, $-S-$, $-SO-$ or $-SO_2-$, and I is $-CR^{60}$ or $-N-$; and $R^{60}$ is H, alkyl or aryl, and g and g' are independently 1 to 4 and g+g' are 2, 3, 4 or 5. Typically suitable heterocyclics include

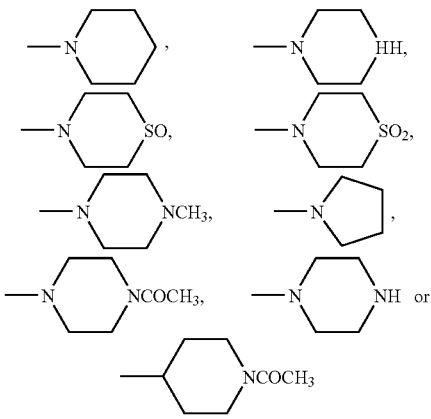

The term "halo" as used herein means fluoro, chloro, bromo or iodo, preferably fluoro or chloro.

In a preferred embodiment of the present invention, the compounds of formula I have one or two of $R^2$, $R^3$ and $R^5$ equal to $R^6(W)_xCO-$, $(HO)_2PO-$ or $R^6(W)_xPO(OH)-$ and at least one of $R^2$, $R^3$ and $R^5$ equal to H. Most preferred compounds of formula I have $R^2=R^3=H$ and $R^5$ equal to $R^6(W)_xCO-$, $(HO)_2PO-$ or $R^6(W)_xPO(OH)-$. In the preferred embodiments of $R^6-(W)_xCO-$ and $R^6(W)_x-PO(OH)-$, W=O and x=0 or 1. In the preferred embodiments of $R^6-(W)_xCO-$ and $R^6(W)_xP(OH)O-$ include $R^{17}(CH_2)_m-NR^{7b}R^{7a}-(CH_2)_nOCO-$ and $R^{17}(CH_2)_m-NR^{7b}R^{7a}-(CH_2)_n-O-PO(OH)$, wherein m=0 to 4 and n=0 to 4; and $R^{17}$ is H, Me, MeCO— or $Me_2N-$ and $R^{7a}R^{7b}N(CH_2)_f-(CHR^{7a})_eOCO-$ or $R^{7a}R^{7b}N(CH_2)_f-(CHR^{7a})_eCO-$ wherein f=0 to 4 and e=1 to 5, and $R^{7a}R^{7b}N$ is $Me_2N-$, MeHN— or MeCONH—.

In most preferred embodiments of $R^6(W)_xCO-$, x=0 and $R^6CO$ is one of

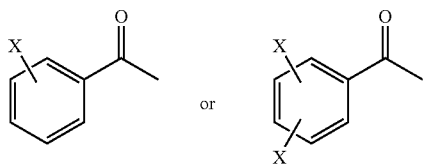

wherein X is independently OH, alkanoyl, e.g., $COCH_3$, $NH_2$, alkanoylamino, e.g., $NHCOCH_3$, hydroxyalkyl, e.g., $CH_2OH$, alkoxy, e.g., $OCH_3NO_2$, or halo, e.g., F, Br or Cl.

Preferably $R^6CO$ is

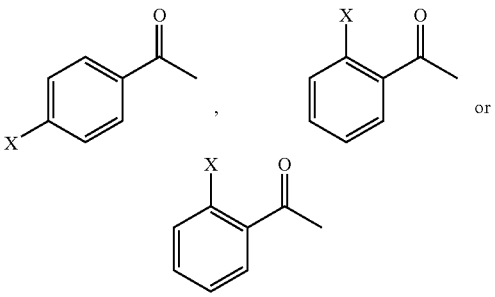

wherein X is $NO_2$, $NH_2$, $NHCOCH_3$ or $OCH_3$.

More preferably $R^6CO$ is

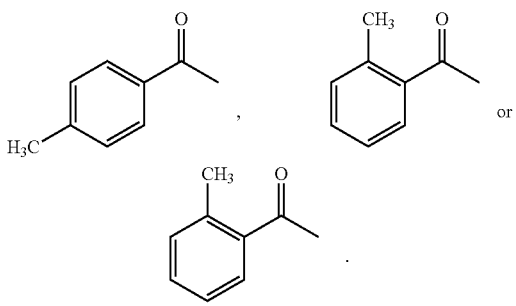

or $R^6$ in $R^6CO$ is one of $HOCH(CH_3)CO-$, $HOCH(C_6H_5)CO-$, $C_2H_5CH(OH)CO-$ or $CH_3CO_2(CH_2)_2CO-$ or $R^6CO$ is a natural or unnatural α-amino acid residue

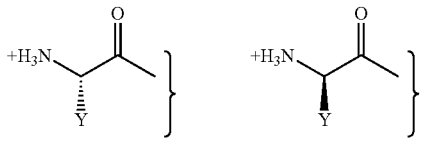

wherein Y=H, CH$_3$; CH$_3$CH$_2$—; CH$_3$CH$_2$CH$_2$—; Me$_2$CH—; Me$_2$CH$_2$CH$_2$—; CH$_3$CH$_2$CH(Me)—PhCH$_2$—; HOOCCH$_2$CH$_2$—; HSCH$_2$—; HOOCCH$_2$—; MeSCH$_2$CH$_2$—; HOCH$_2$—;

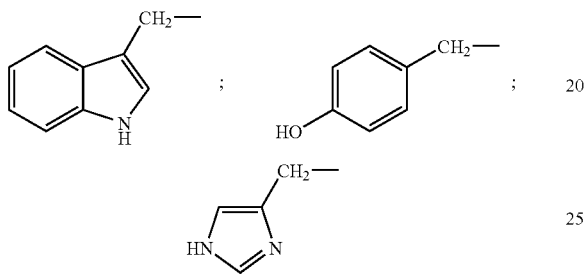

or Y is H$_2$N(CH$_2$)$_4$— or CH$_3$CH(OH)—; or a pharmaceutically acceptable salt thereof;

or Y taken together with the α carbon and N form

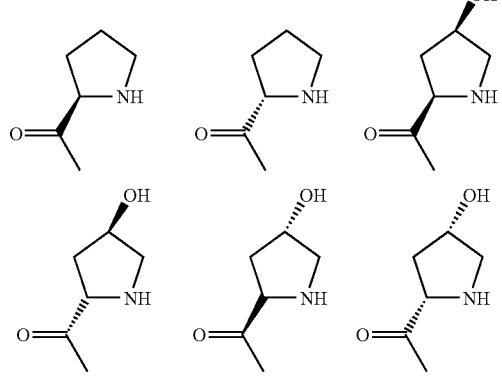

or a pharmaceutically acceptable salt thereof.

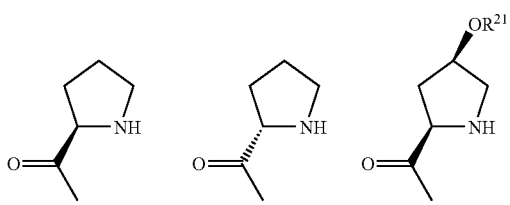

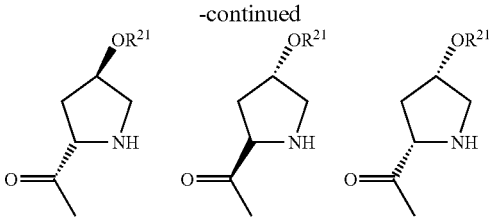

wherein R$^{21}$ is as defined hereinabove; or a pharmaceutically acceptable salt thereof.

Other preferred embodiments for R$^6$CO in the compounds of formula I include

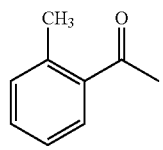

(CH$_3$)$_3$CO—, C$_6$H$_5$CO—, (HO)$_2$PO— and L-C$_6$H$_5$CH$_2$OCONHCH(CH$_3$)CO—, i.e., C$_6$H$_5$CH$_2$OCONHCH In a preferred embodiment of the present invention, the compounds of formula II have one or two of R$^2$, R$^3$ and R$^5$ equal to R$^{20}$(W)$_x$CO— or R$^{20}$(W)$_x$PO(OH)— and at least one of R$^2$, R$^3$ and R$^5$ equal to H. Most preferred compounds of formula II have R$^2$=R$^3$=H and R$^5$ equal to R20$^6$(W)$_x$CO— or R$^{20}$(W)$_x$P(OH)O—. In the preferred embodiments of R$^{20}$(W)$_x$CO— and R$^{20}$(W)$_x$P(OH)O—, W=O and x=0 or 1. In the preferred embodiments of R$^{20}$(W)$_x$CO— and R$^{20}$(W)$_x$P(OH)O— include R$^{27}$(CH$_2$)$_m$—NR$^{21}$R$^{22}$—(CH$_2$)$_n$ OCO— and R$^{27}$(CH$_2$)$_m$—NR$^{21}$R$^{22}$—(CH$_2$)$_n$CO—, R$^{27}$(CH$_2$)$_m$—NR$^{21}$R$^{22}$—(CH$_2$)$_n$O PO(OH)— wherein m=0 to 4 and n=1 to 5; R$^{27}$ is H, Me, MeCO— or Me$_2$N—, R$^{21}$ is H, Me, or MeCO—R$^{22}$ is H, Me, or MeCH$_2$, and R$^{21}$R$^{22}$N is Me$_2$N—, MeHN— or MeCONH—.

In most preferred embodiments of R$^{20}$(W)$_x$CO—, x=0 and R$^{20}$CO is HOCH(CH$_3$)CO—, HOCH(C$_6$H$_5$)CO—, C$_2$H$_5$CH(OH)CO— or CH$_3$CO$_2$(CH$_2$)$_2$CO— or R$^{20}$CO is a natural α-amino acid residue

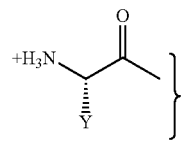

Y=H, CH$_3$; CH$_3$CH$_2$—; CH$_3$CH$_2$CH$_2$—; Me$_2$CH—; Me$_2$CH$_2$CH$_2$—; CH$_3$CH$_2$CH(Me)—PhCH$_2$—; HOOCCH$_2$CH$_2$—; HSCH$_2$—; HOOCCH$_2$—; MeSCH$_2$CH$_2$—

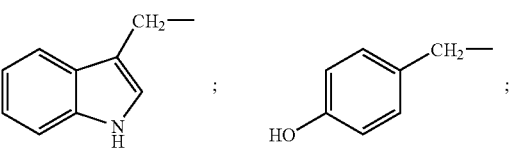

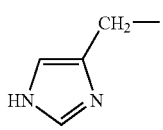

or Y is $H_2N(CH_2)_4$— or $CH_3CH(OH)$—;

or Y taken together with the α carbon and N form

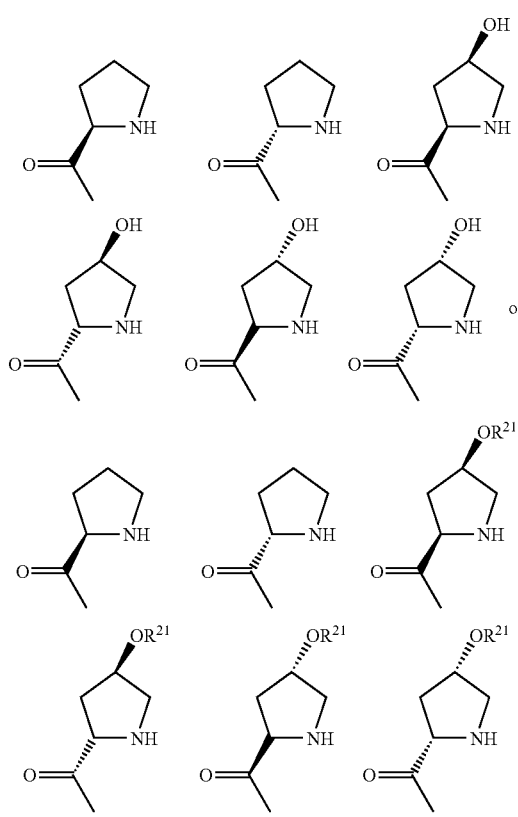

wherein $R^{21}$ is as defined hereinabove; or a pharmaceutically acceptable salt thereof.

or $R^{20}CO$ is

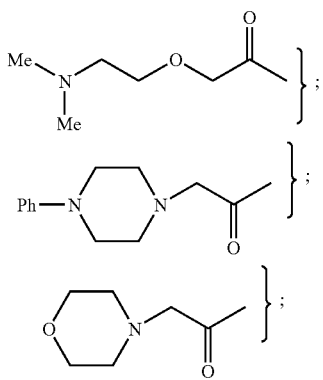

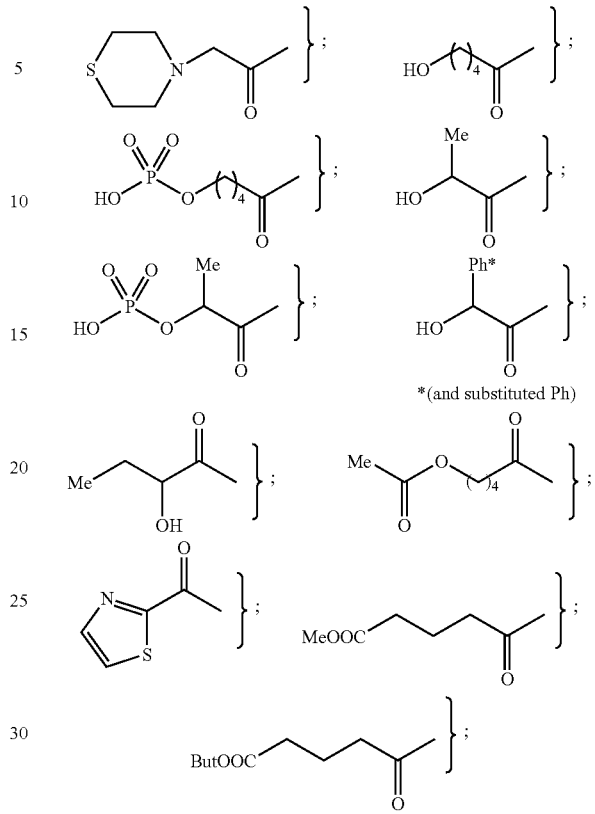

or a pharmaceutically acceptable salt thereof;

wherein Ph is phenyl and phenyl substituted by halo, CN, $NO_2$, OH, $CO_2H$, or alkoxy.

The compounds of formulas I to VIII metabolize in vivo into ribavirin and are useful for treating susceptible viral infections treatable with ribavirin, alone, or in combination with other ant-viral therapies eg., interferon-alfa, and so-called Highly Active Antiretroviral Therapy ("HAART"). A-M. Vandamme et al., *Antiviral Chemistry & Chemotherapy*, 9:187–203 (1998) disclose current clinical treatments of HIV-1 infections in man including at least triple drug combinations or so-called Highly Active Antiretroviral Therapy ("HAART"); HAART involves various combinations of nucleoside reverse transcriptase inhibitors ("NRTI"), non-nucleoside reverse transcriptase inhibitors ("NNRTI") and HIV protease inhibitors ("PI"). The treating of patients having chronic hepatitis C with the compounds of formulas I–VIII is performed as part of a combination therapy with interferon-alfa, including interferon alfa-2a, interferon alfa-2b, consensus interferon especially interferon alfa-2b as well as pegylatyed interferon alfa-2a and pegylatyed interferon alfa-2b.

The present invention provides methods and pharmaceutical compositions containing a compound of formulas II–VIII for treating susceptible viral infections, especially hepatitis C viral infections.

The term "susceptible viral infections" as used herein means viral infections caused by a wide range of RNA and DNA viruses, including, but not limited to, the families of viruses such as flaviviruses-including the genus flavirus, pestivirus of which Kunjin virus is a member, and hepavirus of which hepatitis C virus is a member, and arbovirus of which the West Nile virus is a member-orthomyxoviruses, paramyxoviruses, arenaviruses, bunyaviruses, herpes viruses, adenoviruses, poxviruses, and retroviruses.

Typical suitable "susceptible viral infections" include influenza A and B viral infections; parainfluenza viral infections, respiratory syncytial virus("RSV") infections such as RSV bronchiolitis and RSV pneumonia especially such RSV infections in children and infants as well as RSV pneumonia in patients with preexisting cardiopulmonary disease, measles viral infections, Lassa fever viral infections, Korean Haemorrhagic fever infections, hepatitis B viral (HBV) infections, Crimean-Congo-Haemorrhagic and HCV infections and HIV-1 infections, encephalitis infections such as caused by West Nile virus or Kunjin virus or the St. Louis encephalitis infections as well as viral infections found in immunocompromised patients. Other susceptible viral infections are disclosed in U.S. Pat. No. 4,211,771 at column 2, line 21 to column 3 line 37; doses and dose regimens and formulations are disclosed at column 3, line 4 to column 9, line 5; see also Canadian Patent No. 1,261, 265. Sidwell, R. W., et al. Pharmacol. Ther., 1979, Vol 6 pp 123–146 discloses that the in vivo antiviral experiments conducted with ribavirin generally confirm one broad-spectrum antiviral activity seen in vitro and states that the efficacy of ribavirin is quite dependent upon the site of infection; the manner of treatment; the age of the animal and the virus dosage utilized. Tables 4 and 5 on page 127 list the RNA and DNA virus infections significantly inhibited in vivo by ribavirin.

The in vitro inhibitory concentrations of ribavirin are disclosed in Goodman & Gilman's "*The Pharmacological Basis of Therapeutics*", Ninth Edition, (1996) McGraw Hill, N.Y., at pages 1214–1215. The Virazole product information discloses a dose of 20 mg/mL of Virazole aerosol for 18 hours exposure in the 1999 Physicians Desk Reference at pages 1382–1384.

Ribavirin dosage and dosage regimens are also disclosed by Sidwell, R. W., et al. Pharmacol. Ther 1979 Vol 6. pp123–146 in section 2.2 pp 126–130. Fernandes, H., et al., Eur. J. Epidemiol., 1986, Vol 2(1) pp1–14 at pages 4–9 disclose dosage and dosage regimens for oral, parenteral and aerosol administration of ribavirin in various preclinical and clinical studies.

The term "patients having hepatitis C infections" as used herein means any patient-including a pediatric patient- having hepatitis C and includes treatment-naive patients having hepatitis C infections and treatment-experienced patients having hepatitis C infections as well as those pediatric, treatment-naive and treatment-experienced patients having chronic hepatitis C infections.

These patients having hepatitis C include those who are infected with multiple HCV genotypes including type 1 as well as those infected with, e.g., HCV genotypes 2, 3, 4, 5 and/or 6 and other possible HCV genotypes.

The term "treatment-naive patients having hepatitis C infections" as used herein means patients with hepatitis C who have never been treated with ribavirin or any interferon, including but not limited to interferon-alfa, or pegylated interferon alfa.

The term "treatment-experienced patients having hepatitis C infections" as used herein means patients with hepatitis C who have been treated with ribavirin or any interferon, including but not limited to interferon-alfa, or pegylated interferon alfa, including relapsers and non-responder.

The term "relapsers" as used herein means treatment-experienced patients with hepatitis C who have relapsed after initial response to previous treatment with interferon alone, or in combination with ribavirin.

The term "non-responders" as used herein means treatment-experienced patients with hepatitis C who have not responded to prior treatment with any interferon alone, or in combination with ribavirin.

When the pegylated interferon-alfa administered is a pegylated interferon alfa-2b, the therapeutically effective amount of pegylated interferon alfa-2b administered during the treatment in accordance with the present invention, including in first and second treatment time periods, is in the range of about 0.1 to 9.0 micrograms per kilogram of pegylated interferon alfa-2b administered per week, in single or divided doses, preferably once a week (QW) or twice a week(BIW), preferably in the range of about 0.1 to about 9.0 micrograms per kilogram of pegylated interferon alfa-2b administered once a week (QW) or in the range of about 0.05 to about 4.5 micrograms per kilogram of pegylated interferon alfa-2b administered twice a week(BIW), or is in the range of about 0.5 to about 3.0 micrograms per kilogram of pegylated interferon alfa-2b administered per week, preferably in the range of about 0.5 to about 3.0 micrograms per kilogram of pegylated interferon alfa-2b administered once a week (QW) or in the range of about 0.25 to about 1.5 micrograms per kilogram of pegylated interferon alfa-2b administered twice a week, or is in the range of about 0.75 to about 1.5 micrograms per kilogram of pegylated interferon alfa-2b administered per week, most preferably is in the range of about 0.75 to about 1.5 micrograms per kilogram of pegylated interferon alfa-2b administered once a week or about 0.375 to about 0.75 micrograms per kilogram of pegylated interferon alfa-2b administered twice a week.

When the pegylated interferon-alfa administered to pediatric patients is a pegylated interferon alfa-2b, the therapeutically effective amount of pegylated interferon alfa-2b administered during the treatment in accordance with the present invention is in the range of about 0.1 to 9.0 micrograms per kilogram of pegylated interferon alfa-2b administered per week, in single or divided doses, preferably once a week (QW) or twice a week(BIW), more preferably about 0.1 to about 9.0 micrograms per kilogram of pegylated interferon alfa-2b administered once a week (QW), or about 0.05 to about 4.5 micrograms per kilogram of pegylated interferon alfa-2b administered per week, in single or divided doses, preferably once a week (QW) or twice a week(BIW), more preferably about 0.05 to about 4.5 micrograms per kilogram of pegylated interferon alfa-2b administered once a week, or preferably about 0.75 to about 3.0 micrograms per kilogram of pegylated interferon alfa-2b administered in single or divided doses, preferably once a week (QW) or twice a week(BIW), more preferably about 0.75 to about 3.0 micrograms per kilogram of pegylated interferon alfa-2b administered once a week or about 0.375 to about 1.5 micrograms per kilogram of pegylated interferon alfa-2b administered twice a week, and most preferably about 2.25 to about 2.6 micrograms per kilogram of pegylated interferon alfa-2b administered once a week or about 1.1 to about 1.3 micrograms per kilogram of pegylated interferon alfa-2b administered twice a week(BIW).

When the pegylated interferon-alfa administered is a pegylated interferon alfa-2a, the therapeutically effective amount of pegylated interferon alfa-2a administered in accordance with the present invention, is in the range of about 50 micrograms to about 500 micrograms once a week("QW"), preferably about 150 micrograms to about 250 micrograms QW or the effective amount is in the range of about 50 micrograms to about 250 micrograms twice a week, preferably about 100 micrograms to about 125 micrograms twice a week.

When the pegylated interferon-alfa administered to a pediatric patient is a pegylated interferon alfa-2a, the therapeutically effective amount of pegylated interferon alfa-2a administered in accordance with the present invention, is in the range of about 50 micrograms to about 500 micrograms once a week("QW"), preferably about 300 micrograms to about 375 micrograms QW or the therapeutically effective amount of pegylated interferon alfa-2a administered to a pediatric patient is in the range of about 50 micrograms to about 250 micrograms twice a week, preferably about 150 micrograms to about 190 micrograms once a week The esters of ribavirin represented by formulas I–VIII are administered to the patient having chronic HCV in association with pegylated interferon-alfa, that is, before, after or concurrently with the administration of the pegylated interferon alfa. The pegylated interferon-alfa dose is preferably administered during the same period of time that the patient receives doses of esters of ribavirin represented by formulas I–VIII. The amount of esters of ribavirin represented by formulas I–VIII administered concurrently with the pegylated interferon-alfa is from about 200 to about 1600 mg per day, preferably about 300 to about 1200 mg/day or about 400 to about 800 mg day and most preferably about 400 to about 600 mg a day. The pegylated interferon-alfa dose is also preferably administered to the pediatric patient during the same period of time that such patient receives doses of the esters of ribavirin represented by formulas I–VIII. The amount of the 5'-amino acid esters of ribavirin represented by formulas III–VIII administered to the pediatric patient having chronic HCV concurrently with the interferon-alfa is from about 1 to about 30 mg per kilogram per day, preferably from about 4 to about 15 mg per kilogram per day, more preferably about 6, 8 or 15 mg per kilogram per day, most preferably about 8 to 10 mg per kilogram per day in divided doses.

Pegylated interferon-alfa formulations are not effective when administered orally, so the preferred method of administering the pegylated interferon-alfa is parenterally, preferably by sub-cutaneous(SC), intravenous(IV), or intramuscular(IM) injection. The 5'-amino acid esters of ribavirin represented by formula I may be administered orally in capsule, tablet, or liquid form, intranasally as an aerosol by nasal spray or parenterally, preferably by SC, IV, or IM injection. The esters of ribavirin represented by formulas I–VIII may be orally administered in association with the parenteral administration of pegylated interferon-alfa. Of course, other types of administration of both medicaments, as they become available, are contemplated, such as transdermally, by suppository, by sustained release dosage form, and by pulmonary inhalation. Any form of administration will work so long as the proper dosages are delivered without destroying the active ingredient The term "interferon-alfa" as used herein means the family of highly homologous species-specific proteins that inhibit viral replication and cellular proliferation and modulate immune response. Typical suitable interferon-alfas include, but are not limited to, recombinant interferon alfa-2b, such as Intron-A interferon available from Schering Corporation, Kenilworth, N.J., recombinant interferon alfa-2a, such as Roferon interferon available from Hoffmann-La Roche, Nutley, N.J., recombinant interferon alpha-2c, such as Berofor alpha 2 interferon available from Boehringer Ingelheim Pharmaceutical, Inc., Ridgefield, Conn., interferon alpha-n1, a purified blend of natural alfa interferons, such as Sumiferon available from Sumitomo, Japan or as Wellferon interferon alpha-n1 (INS) available from the Glaxo-Wellcome Ltd., London, Great Britain, or a consensus alpha interferon, such as those described in U.S. Pat. Nos. 4,897,471 and 4,695,623 (especially Examples 7, 8 or 9 thereof) and the specific product available from Amgen, Inc., Newbury Park, Calif., or interferon alfa-n3 a mixture of natural alfa interferons made by Interferon Sciences and available from the Purdue Frederick Co., Norwalk, Conn., under the Alferon Tradename. The use of interferon alfa-2a or alpha 2b is preferred. Since interferon alpha 2b, among all interferons, has the broadest approval throughout the world for treating chronic hepatitis C infection, it is most preferred. The manufacture of interferon alpha 2b is described in U.S. Pat. No. 4,530,901.

The term "pegylated interferon alfa" as used herein means polyethylene glycol modified conjugates of interferon alfa, preferably interferon alfa-2a and -2b. The preferred polyethylene-glycol-interferon alfa -2b conjugate is $PEG_{12000}$-interferon alfa 2b. The phrases "12,000 molecular weight polyethylene glycol conjugated interferon alpha" and "$PEG_{12000}$-IFN alfa" as used herein mean conjugates such as are prepared according to the methods of International Application No. WO 95/13090 and containing urethane linkages between the interferon alfa-2a or -2b amino groups and polyethylene glycol having an average molecular weight of 12000.

The preferred $PEG_{12000}$-interferon alfa-2b is prepared by attaching a PEG polymer to the epsilon amino group of a lysine residue in the IFN alfa-2b molecule. A single $PEG_{12000}$ molecule is conjugated to free amino groups on an IFN alfa-2b molecule via a urethane linkage. This conjugate is characterized by the molecular weight of $PEG_{12000}$ attached. The PEG12000-IFN alfa-2b conjugate is formulated as a lyophilized powder for injection. The objective of conjugation of IFN alfa with PEG is to improve the delivery of the protein by significantly prolonging its plasma half-life, and thereby provide protracted activity of IFN alfa.

Other pegylated interferon alfa conjugates can be prepared by coupling an interferon alfa to a water-soluble polymer. A non-limiting list of such polymers include other polyalkylene oxide homopolymers such as polypropylene glycols, polyoxyethylenated polyols, copolymers thereof and block copolymers thereof. As an alternative to polyalkylene oxide-based polymers, effectively non-antigenic materials such as dextran, polyvinylpyrrolidones, polyacrylamides, polyvinyl alcohols, carbohydrate-based polymers and the like can be used. Such interferon alfa-polymer conjugates are described in U.S. Pat. No. 4,766,106, U.S. Pat. No. 4,917,888, European Patent Application No. 0 236 987, European Patent Application Nos. 0510 356, 0 593 868 and 0 809 996 (pegylated interferon alfa-2a) and International Publication No. WO 95/13090.

Pharmaceutical composition of pegylated interferon alfa suitable for parenteral administration may be formulated with a suitable buffer, e.g., Tris-HCl, acetate or phosphate such as dibasic sodium phosphate/monobasic sodium phosphate buffer, and pharmaceutically acceptable excipients, e.g., sucrose, carriers, e.g., humanor recombinant plasma albumin, tonicity agents, e.g. NaCl, preservatives, e.g., thimerosol, cresol or benyl alcohol, and surfactants, e.g., tweens or polysorabates in sterile water for injection. The pegylated interferon alfa-may be stored as lyophilized powders under a refrigeration at 2°–8° C. The reconstituted aqueous solutions are stable when stored between 2° and 8° C. and used within 24 hours of reconstitution. See for example U.S. Pat. Nos., 4,492,537; 5,762,923 and 5,766, 582.The reconstituted aqueous solutions may also be stored in prefilled, multi-dose syringes such as those useful for delivery of drugs such as insulin. Typical suitable syringes include systems comprising a prefilled vial attached to a pen-type syringe such as the NOVOLET Novo Pen available from Novo Nordisk, as well as prefilled, pen-type syringes which allow easy self-injection by the user. Other syringe systems include a pen-type syringe comprising a glass cartridge containing a diluent and lyophilized pegylated interferon alfa powder in a separate compartment.

A person suffering from chronic hepatitis C infection may exhibit one or more of the following signs or symptoms:

(a) elevated ALT,
(b) positive test for anti-HCV antibodies,
(c) presence of HCV as demonstrated by a positive test for the presence of HCV-RNA in the serum,
(d) clinical stigmata of chronic liver disease,
(e) hepatocelluar damage.

The combination therapy of pegylated interferon-alfa and the esters of ribavirin represented by formulas I–VIII and preferably the 5'-amino acid esters of ribavirin represented by formulas III–VIII may also be administered in association with anti-retroviral therapy, e.g., HAART, to the patient co-infected with the HIV-1 and HCV infection and exhibiting one or more of the above signs or symptoms in amounts sufficient to eliminate or at least alleviate one or more of the signs or symptoms of hte HCV infection, and to lower the HIV-1-RNA and HCV-RNA serum levels each by at least a power of ten, and preferably to eradicate detectable HCV-RNA at least by the end of about 20 to about 50 weeks, preferably at least 24 weeks to 48 weeks and to maintain no detectable HCV-RNA for at least 24 weeks after the end of the about 20 to about 50 weeks. Administration of the 5'-amino acid esters of ribavirin represented by formula I may be discontinued after the end of the second time period depending upon the judgment of the attending clinician.

The term "no detectable HCV-RNA" in the context of the present invention means that there are fewer than 100 copies of HCV-RNA per ml of serum of the patient as measured by quantitative, multi-cycle reverse transcriptase PCR methodology. HCV-RNA is preferably measured in the present invention by research-based RT-PCR methodology well known to the skilled clinician. This methodology is referred to herein as HCV-RNA/qPCR. The lower limit of detection of HCV-RNA is 100 copies/mL. Serum HCV-RNA/qPCR testing and HCV genotype testing will be performed by a central laboratory. See also J. G. McHutchinson et al. (N. Engl. J. Med., 1998, 339:1485–1492), and G. L. Davis et al. (N. Engl. J. Med. 339:1493–1499).

Biological Activity

The compounds of formulas I–VIII are useful for treating patients having susceptible viral infections such as chronic hepatitis C as part of a Combination Therapy with interferon-alfa, especially interferon alfa-2b. The compounds of formulas I and II wherein $R^5$ is $R^6(W)_xCO-$, $R^6(W)_xCS$, $(HO)_2PO-$, $R^6(W)_xP(OH)O-$ or $HOSO_2-$ metabolizes in vivo into ribavirin.

Compounds of formula I wherein $R^2=R^3=H$ and $R^5=(HO)_2PO-$, or

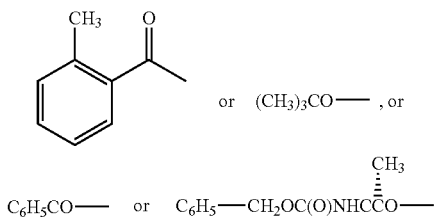

or $(CH_3)_3CO-$, or $C_6H_5CO-$ or $C_6H_5-CH_2OC(O)NH-CCO-$ have produced higher plasma concentration of ribavirin after administration to rats.

TABLE 1

Ribavirin Concentrations of pooled Rat[1] Plasma (2 rats/pool) following oral administration of 40 mpk of the compounds of formula I in 20% hydroxypropyl-beta-cyclodextrin

| Compound[2] | AUC (pooled)[3] (ng · hr/mL) | C.V.[4] (%) | Conc. (6 hr) (ng/mL) | C.V.[4] (%) |
|---|---|---|---|---|
| A | 1523.65 | 23.56 | 142.54 | 49.37 |
| B | 1309.76 | 1.68 | 241.83 | 19.61 |
| C | 1303.34 | 67.42 | 170.42 | 37.78 |
| D | 1065.88 | 29.12 | 116.33 | 10.73 |
| E | 754.77 | 74.42 | 122.71 | 44.68 |

[1]Male Charles River rats obtained from Charles River, Wilmington, MA 01887
[2](a) Compound A is the compound of formula I wherein $R^5$ is $(CH_3)_3CCO-$
(b) Compound B is the compound of formula I wherein $R^5$ is $(HO)_2P(O)-$
(c) Compound C is the compound of formula I wherein $R^5$ is $C_6H_5CO-$
(d) Compound D is the compound of formula I wherein $R^5$ is $C_6H_5CH_2OCONH$ $CH(CH_3)CO-$
(e) Compound E is Ribavirin
[3]Area under the curve measured from 0 to 6 hrs. after oral administration to 2 rats of an aqueous solution of compounds of formula I in 20% HPBCD
[4]% CV is percent coefficient of variation which is a relative measure of variability. See Steele and Torrie, "Principles and Procedures of Statistics", (1980) 2nd Edition, McGraw-Hill, NY, at page 27.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg, according to the particular compound and particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/kg/day to about 100 mg/kg/day, in two to four divided doses.

In a preferred embodiment of the present invention, those patients co-infected with HIV-1 and HCV infections are treated with pegylated interferon alfa in combination with the preferred 5'-amino acid esters of ribavirin represented by formulas III to VIII and a HAART combination considered appropriate by the attending clinician and the patient. See also J. G. McHutchinson et al. (N. Engl. J. Med., 1998, 339:1485–1492), and G. L. Davis et al. (N. Engl. J. Med. 1998, 339:1493–1499).

The preferred compounds of formulas III–VIII are useful for treating patients having susceptible viral infections, e.g., chronic hepatitis C. The compounds of formulas III–VIII metabolize in vivo into ribavirin and are useful for treating susceptible viral infections treatable with ribavirin, alone, or in combination with other anti-viral therapies, e.g., interferon-alfa and HAART. The treating of patients having chronic hepatitis C with the compounds of formulas III–VIII is performed as part of a combination therapy with interferon-alfa, especially interferon alfa-2b.

Compounds of formulas III VIII metabolize in vivo into ribavirin and have produced higher plasma concentrations of ribavirin after oral administration of a compound of formula VII to rats and monkeys compared to administration of ribavirin. The pharmacokinetics of the preferred compounds of formulas VII are presented in Tables 2 & 3

TABLE 2

Ribavirin Concentrations of Pooled Rat[1] Plasma (2 rats/pool) Following Oral Administration of 20 mpk Ribavirin Equivalent Amounts of Salts of the Compounds of Formula VII in 20% Hydroxypropyl-beta-cyclodextrin(HPBCD)

| Compound[2] | AUC (pooled)[3] (ng.hr/mL) | C.V.[4] (%) | Conc. (6 hr) (ng/mL) | C.V.[4] (%) |
|---|---|---|---|---|
| A | 1238 | 81.4 | 152 | 30.5 |
| B | 2554 | 25.0 | 226 | 20.0 |
| C | 1011 | *** | 294 | — |
| D | 2043 | 1.4 | 173 | 67.3 |

[1]Male Sprague Dawely (CD) rats (N = 2)obtained from Charles River, Wilmington, MA 01887: Single dose, PO, (Fasted overnight); 20 mg/Kg(mpk) ribavirin equivalent PO dose of the compound of formula I in 20% HPBCD(w/v);
Concentration: 4 mg/ml ribavirin equivalent and dosing volume: 5 ml/Kg.
[2](a) Compound A is the compound of formula VII wherein $R^{50}$ is H, i.e., ribavirin TABLE 2-continued Ribavirin Concentrations of Pooled Rat[1] Plasma (2 rats/pool) Following Oral Administration of 20 mpk Ribavirin Equivalent Amounts of Salts of the Compounds of Formula VII in 20% Hydroxypropyl-beta-cyclodextrin(HPBCD)

| Compound[2] | AUC (pooled)[3] (ng.hr/mL) | C.V.[4] (%) | Conc. (6 hr) (ng/mL) | C.V.[4] (%) |
|---|---|---|---|---|

(b) Compound B is the trifluoroacetate salt of the compound of formula VII wherein $R^{50}$ is
$[CF_3CO_2^-]L\text{—}CH_3CH_2(CH_3)CHCH(NH_3^{\oplus})\text{—}CO\text{—}$.
(c) Compound C is the ditosylate salt of the compound of formula VII wherein $R^{50}$ is
$2[p\text{-}CH_3C_6H_4SO_3^-]\cdot L\text{—}H_3N^{\oplus}(CH_2)_4CH(NH_3^{\oplus})\text{—}CO\text{—}$.
(d) Compound D is the tosylate salt of the compound of formula VII wherein $R^{50}$ is $[p\text{-}CH_3C_6H_4SO_3^-]$ L-$CH_3CH(NH_3^{\oplus})$—CO—, i.e.,

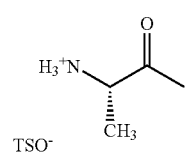

TSO⁻

[3]Area under the curve measured from 0 to 6 hrs. after oral administration to 2 rats of an aqueous solution of compounds of formula VII in 20% HPBCD.
[4]% CV is percent coefficient of variation which is a relative measure of variability. See Steele and Torrie, "Principles and Procedures of Statistics", (1980) 2nd Edition, McGraw-Hill, NY, at page 27.

TABLE 3

Ribavirin Concentrations of Pooled Cynomolgus Monkeys[1] Plasma (2 monkeys/pool) Following Oral Administration of 10 mpk of Ribavirin Equivalent Amounts of Salts of Compounds of Formula VII Dissolved in 0.4% Methylcellulose(MC)

| Compound[2] | AUC (24)[3] (ng.hr/mL) | AUC(48 hr). (ng.hr/mL) | AUC(72 hr) (ng.hr/mL) | Cmax. (ng/mL) |
|---|---|---|---|---|
| A | 4013 | 5506 | 5902 | 398[4] |
| B | 4791 | 5749 | 5749 | 831[5] |
| C | 6033 | 8050 | 8381 | 661[6] |
| D | 9072 | 11632 | 12528 | 1012[7] |

[1]Non-naive male Cynomolgus monkeys(N = 2)
[2](a) Compound A is the compound of formula VII wherein R is H, i.e. , ribavirin.
(b) Compound B is the trifluoroacetate salt of the compound of formula VII wherein $R^{50}$ is
$[CF_3CO_2^-]$ L-$CH_3CH_2(CH_3)CHCH(NH_3^{\oplus})$—CO—.
(c) Compound C is the ditosylate salt of the compound of formula VII wherein $R^{50}$ is
$2[p\text{-}CH_3C_6H_4SO_3^{31}]\cdot$ L-$H_3N^{\oplus}(CH_2)_4CH(NH_3^{\oplus})$—CO—
(d) Compound D is the tosylate salt of the compound of formula VI wherein $R^{50}$ is
$[p\text{-}CH_3C_6H_4SO_3^-]$ L-$CH_3CH(NH_3^{\oplus})$—CO—, i.e.,

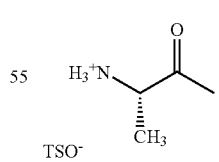

TSO⁻

[3]Area under the curve measured from 0 to 24, 48 or 72 hrs. after oral administration to non-naive male Cynomolgus monkeys of an oral gavage of a 0.4% MC solutions of the compounds of formula I at a target dose of 10 mg (free base)/Kg and at a target dose volume of 2 ml/Kg..
[4]Tmax for A is 1.5 hrs.
[5]Tmax for B is 1.0 hrs.
[6]Tmax for C is 1.5 hrs.
[7]Tmax for D is 1.5 hrs The pharmaceutical compositions of the preferred 5'-amino acid esters of ribavirin of the present invention (represented by formulas III–VIII) may be adapted for any mode of administration e.g., for oral, parenteral, e.g., subcutaneous ("SC"), intramuscular ("IM"), intravenous ("IV") and intraperitoneal ("IP"), topical or vaginal administration or by inhalation (orally or intranasally). Preferably the ribavirin compounds represented by formula I are administered orally.

Such compositions may be formulated by combining a compound of formulas III–VIII or an equivalent amount of a pharmaceutically acceptable salt of compound I with an suitable, inert, pharmaceutically acceptable carrier or diluent which may be either solid or liquid. The compounds of formulas III–VIII are preferably converted into the pharmaceutically acceptable acid addition salts by adding to compounds of formulas III–VIII an equivalent amount (or two equivalents in the case of for example the lysine ester) of a pharmaceutically acceptable acid. Typically suitable pharmaceutically acceptable acids include the mineral acids, e.g., $HNO_3 H_2SO_4$, $H_3PO_4$, HCl, HBr, organic acids, including, but not limited to, acetic, trifluoroacetic, propionic, lactic, maleic, succinic, tartaric, glucuronic and citric acids as well as alkyl or arylsulfonic acids, such as p-toluenesulfonic acid, 2-naphthalenesulfonic acid, or methanesulfonic acid. Typically suitable pharmaceutically acceptable salts include the following anions: acetate, adipate, besylate(benzenesulfonate), bromide, camsylate[(+)-7,7-dimethyl-2-oxobicyclo[2.2.1]hepatane-1-methanesulfonate], chloride, citrate, edisylate(1,2-ethanedisulfonate), estolate(dodecyl sulfate), fumarate, gluceptate(glucoheptonate), gluconate, glucuronate, hippurate, hyclate(hydrochloride, hemiethanolate), hydrobromide, hydrochloride, iodide, isethionate(2-hydroxyethanesulfonate), lactate, lactobionate, maleate, mesylate(methanesulfonate), methylbromide, methylsulfate, napsylate, nitrate, oleate, pamoate [4,4'-methylenebis[3-hydroxy-2-napthalene-carboxylate]], phosphate, polygalacturonate, stearate, succinate, sulfate, sulfosalicylate, tannate, tartrate, terephthalate, tosylate(p-toluenesulfonate), triethiodide.;

and the following catrons:
benzathine(N,N-bis(phenylmethyl)-1,2-ethanediamine),
calcium, diolamine(2,2-iminobis(ethanol), meglumine[1-deoxy-1-(methylamino)-D-glucitol], olamine(2-aminoethanol), potassium, procaine, sodium tromethamine[2-amino-2-(hydroxymethyl)-1,3 propanediol,] and zinc.

The preferred pharmaceutically acceptable salts are trifluoroacetate, tosylate, mesylate, and chloride.

Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection. Solid form preparations may be converted into liquid preparations shortly before use for either oral or administration. Parenteral forms to be injected intravenously, intramuscularly or subcutaneously are usually in the form of sterile solutions and may contain tonicity agents (salts or glucose), and buffers. Opacifiers may be included in oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g., nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in a unit dosage form. In such form, the preparation is subdivided into suitably sized unit doses containing appropriate quantities of the active component, e.g., an effective amount to achieve the desired purpose.

The effective amount or therapeutically effective amount of active compound of the present invention (of formulas I–VIII) in a unit dose of preparation may be varied or adjusted from about 1 mg to about 1600 mg per day, preferably from about 1 mg to about 1200 mg per day, or about 300 mg to about 1200 mg per day, more preferably from about 1 mg to about 800 mg per day, or about 400 mg to about 800 mg per day and most preferably from about 1 mg to about 100 mg per day from about 400 mg to about 600 mg per day, in single or divided doses, according to the particular compound and particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. The dose of the preferred compounds of formulas III to VIII should be chosen to provide steady state plasma concentrations of ribavirin in the range of about 0.1 ug/mL to about 100 ug/mL, preferably in the range of about 0.1 ug/mL to about 50 ug/mL, more preferably in the range of about 1 ug/mL to about 3 ug/mL., and most preferably in the range of about 1.8 ug/mL to about 2.6 ug/mL. Plasma ribavirin concentrations may be determined using high pressure liquid chromatographic material with tandem mass spectrometric detection. The method was validated with respect to linearity, selectivity, precision, accuracy and has a limit of quantitation of 50 microg/mL. A typical recommended daily dosage regimen for oral administration can range from about 1 mg/kg/day to about 100 mg/kg/day, in two to four divided doses.

A compound represented by the formula VI
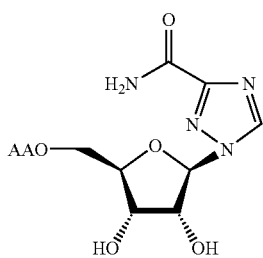
or a pharmaceutically acceptable salt thereof;
wherein AA is a natural or unnatural amino acid moiety represented by the formulas in Table AA herein below:
TABLE AA
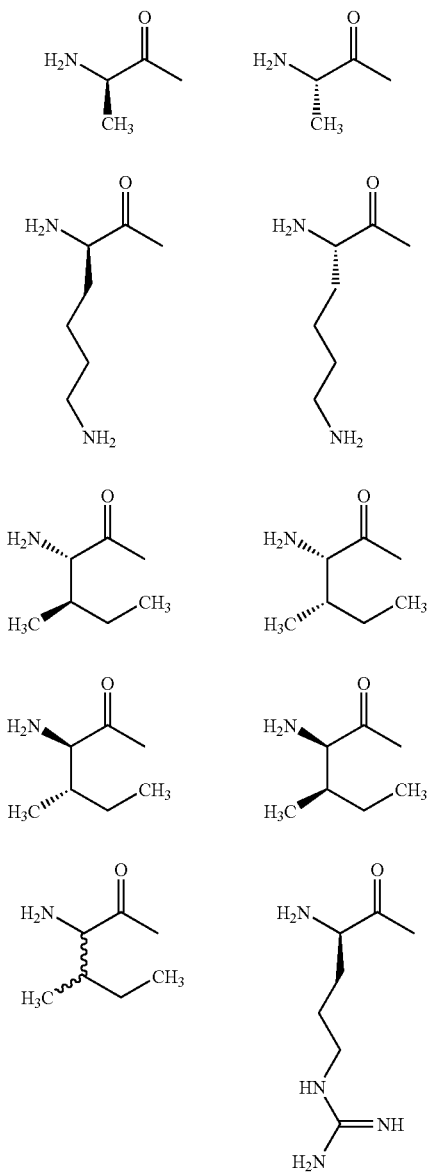
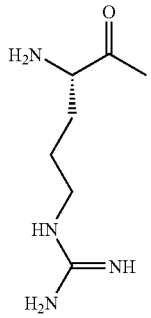
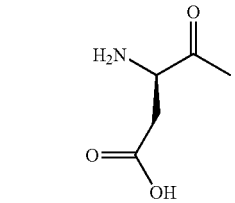
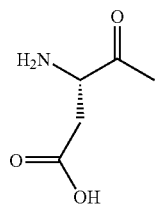
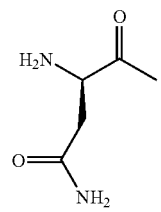
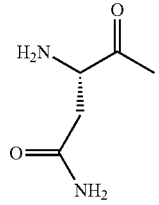
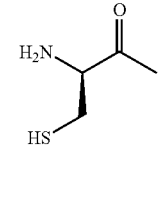
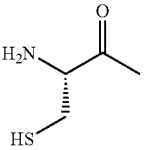
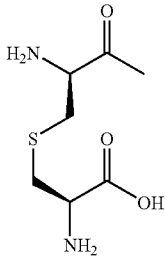
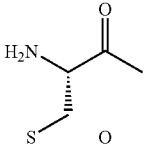
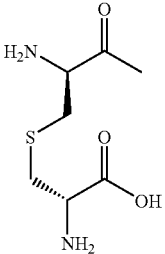
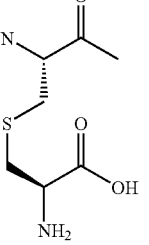
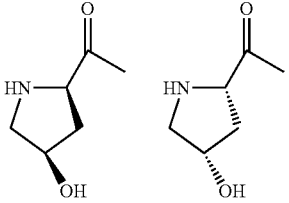

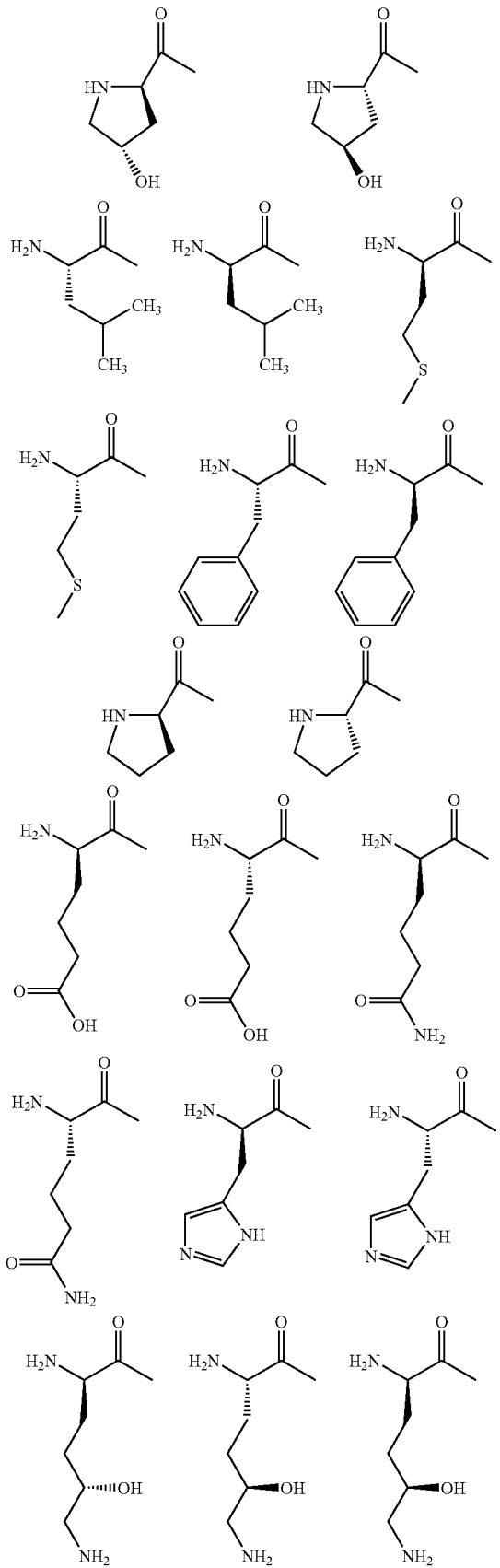
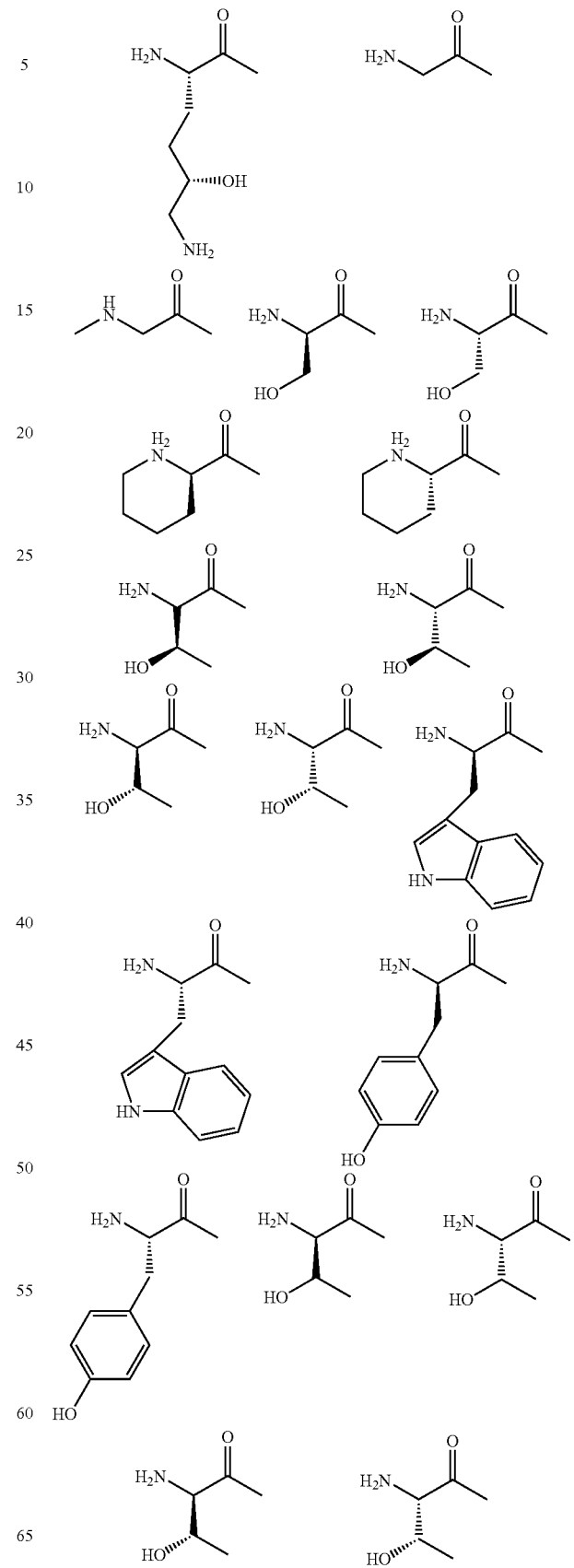

-continued

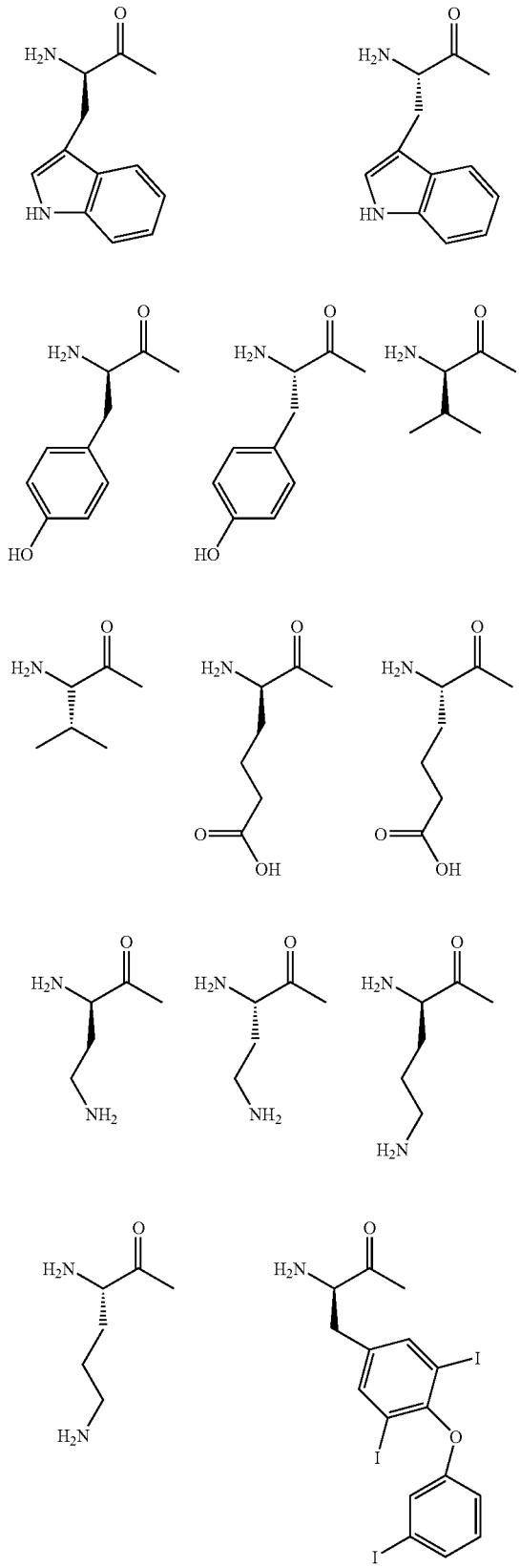

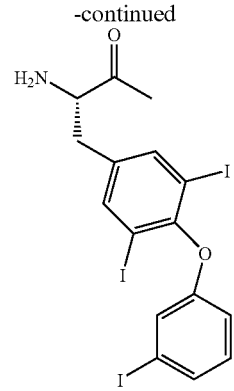

The present invention concerns compounds represented by the formula VII:

VII

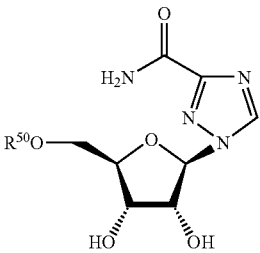

wherein $R^{50}$ is $CH_3CH(NH_2)$—CO—, $CH_3CH_2(CH_3)$ CHCH($NH_2$)—CO— or $H_2N(CH_2)_4CH(NH_2)$—CO—; or stereoisomers thereof, or a pharmaceutically acceptable salt thereof.

R may be $CH_3CH(NH_2)$—CO—, i.e., α-aminopropanoyl, in the form of a stereoisomeric mixture, i.e. the DL-form of α-aminopropanoyl- or as one of the enantiomers, i.e., the L-form:

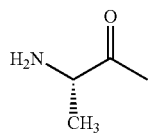

or D-form:

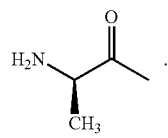

or mixtures thereof.

R may be $CH_3CH_2(CH_3)CHCH(NH_2)$—CO—, i.e., 2-amino-3-methylpentanoyl, (a) as a stereoisomeric mixture, i.e., the DL-Form-DL-(−+) erythro-2-amino-3-methylvaleroyl- of the formula:

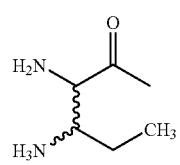

or (b) as one of the diastereomers of the formula, i.e., the L-allo-form of the formula:

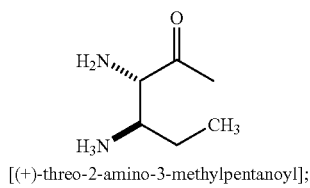

[(+)-threo-2-amino-3-methylpentanoyl];

or the L-form of the formula:

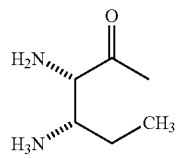

[L-(+)-amino-3-methylpentanoyl, or (2S,3S)-2--amino-3-methylpentanoyl];

or mixtures thereof;
or (c) as one of the diastereomers of the formula:

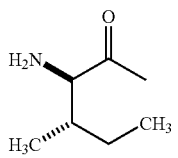

[(2R, 3S)-2--amino-3-methylpentanoyl]; or

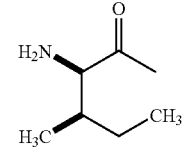

[(2R, 3S)-2--amino-3-methylpentanoyl];

or mixtures thereof.

R may be $H_2N(CH_2)_4CH(NH_2)$—CO— in the form of a stereoisomeric mixture, or as one of the enantiomers, i.e., the L-form of the formula:

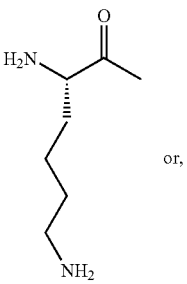

or, the D-form of the formula:

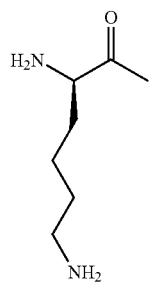

Preferably, R is L-α-aminopropanoyl of the formula:

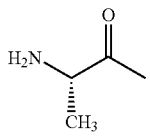

General Synthetic Preparation

Ribavirin, 1-β-D-ribofuranosyl-1H-1,2,4-triazole-3-carboxamide, available from ICN Pharmaceuticals, Inc., Costa Mesa, Calif., is described in the Merck Index, compound No. 8199, Eleventh Edition. Its manufacture and formulation is described in U.S. Pat. No. 4,211,771.

The ribavirin derivatives of formulas I–VIII may be prepared by use of the sequences of steps illustrated in the following Schemes, and in the Examples using the compounds listed hereinafter the Schemes.

In Scheme I, compounds of formula I wherein $R^5=R^{5a}CO—$, $R^3=R^{3a}CO$ and $R^2=H$ and $R^5=R^{5a}CO—$ and $R^2=R^{2a}CO—$ and $R^3=H$ and $R^5=R^{5a}CO—$ and $R^3=R^2=H$, are prepared Compound 110 (ribavirin) and benzaldehyde are treated with $ZnCl_2$ in excess benzaldehyde as solvent at ambient temperature (20 to 25° C.) for 24 hrs. to give compound 111. Treatment of 111 with the alkanoyl chloride $R^{5a}COCl$ in the presence of base e.g. triethylamine ("TEA"); or with the carboxylic acid ($R^{5a}COOH$) and triethylamine and coupling reagent such as dicyclohexylcarbodiimide ("DCC") produces compound 112. Removal of the acetal protecting group with trifluoroacetic acid:water (9:1,v/v) at ambient temperature for 0.25–2 hrs, preferably about 0.05 hrs. provides compound 113. Compound 113 is converted into a mixture of compounds 114 and 115 by treatment of 113 with $R^{3a}COOH$, base and DCC or $R^{3a}COCl$ and base, e.g., TEA.

Compounds 114 and 115 may be separated by standard chromatographic techniques to provide pure compounds 114 and 115.

In Scheme II, compounds of formula 1 wherein $R^5=R^3=H$ and $R^2—R^{2a}CO—$ are prepared from compound 110 (ribavirin). Compound 110 is treated with 1,3-dichloro-1,1,3,3-tetraisopropyldisiloxane, i.e., $[(i-Pr)_2SiCl]_2$ 0, in DMF as solvent in the presence of imidazole for 1–4 hrs. at ambient temperature to give compound 116. Treatment of 116 with $R^{2a}COCl$ and base e.g., TEA or $R^{2a}COOH$, base and a coupling reagent e.g., DCC for 12–48 hrs. at ambient temperature provides 117. Treatment of 17 with $Bu_4NF$ in tetrahydrofuran ("THF") at ambient temperature for 1–10 hrs. provides compound 118.

Scheme IV illustrates preparation of the compounds of formula I wherein $R^5=R^{5a}CO-$ or $R^5=R^{5a}$ and $R^3=R^2=H$. Treatment of ribavirin 110 with $R_{5a}COON=C(CH_3)_2$ in the presence of an enzyme, such as Novo SP 435 lipase at 65° C. in a solvent such as THF or dioxane for 12–48 hrs selectively adds $R^{5a}CO$ to the form compound 124. See also Examples 9 to 14.

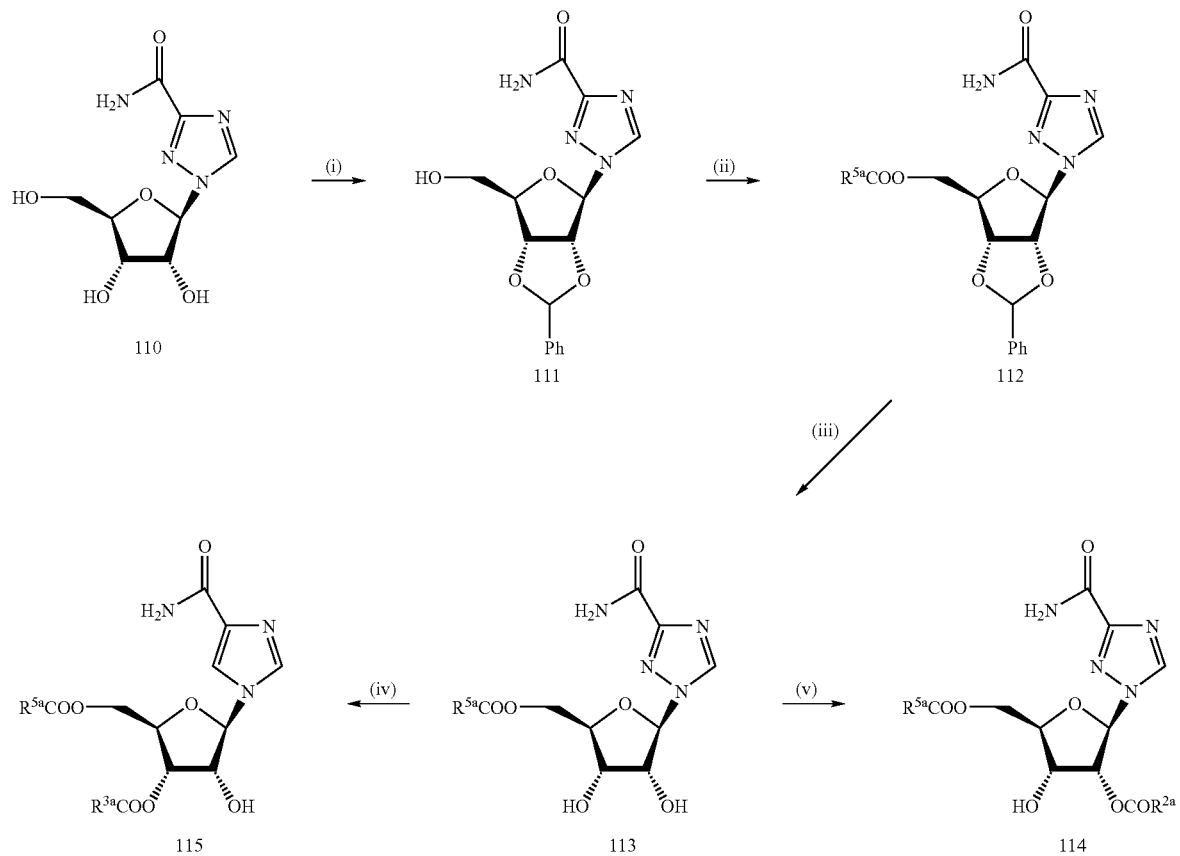

Reagent: (i) $ZnCl_2$, PhCHO,
(ii) $R^{5a}COCl$, $Et_3N$; or $R^{5a}COOH$, $Et_3H$, coupling reagent,
(iii) $TFA-H_2O$ (9:1),
(iv) $R^{3a}COOH$ or $R^{3a}(W)xCOOH$, coupling reagent, base; or $R^{3a}COCl$, or $R^{3a}(W)x$, base,
(v) $R^{3a}COOH$, coupling reagent, base; or $R^{3a}COCl$, base Scheme III illustrates the preparation of the compounds of formula I wherein $R^5=R^2=H$ and $R^3=R^{3a}CO-$ and $R^5=R^3=H$ and $R^2=R^{2a}CO-$ Ribavirin is treated chloride or [MeOC$_6$H$_4$(C$_6$H$_5$)$_2$]CCOCl and base, e.g., pyridine in a solvent DMF at ambient temperature for 6–24 hrs. to provide 119. Treatment of 119 with $R^{2a}COCl$ and base or $R^{2a}COOH$, base and a coupling reagent, e.g., DCC, provides a mixture of compounds 120 and 121. The mixture is separated into the pure compounds by standard chromatographic techniques. Treatment of 120 or 121 with para-toluenesulfonic acid ("p-TsOH") in methanol in the presence of hydrogen and a palladium on charcoal catalyst at ambient temperature for 2–48 hrs. removes the protecting group to give 122 and 123, respectively. p-TsOH salt thereof.

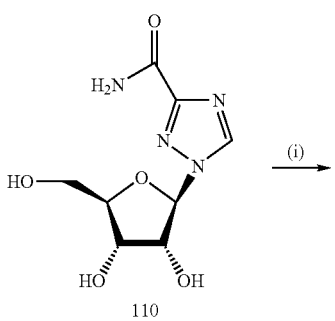

-continued
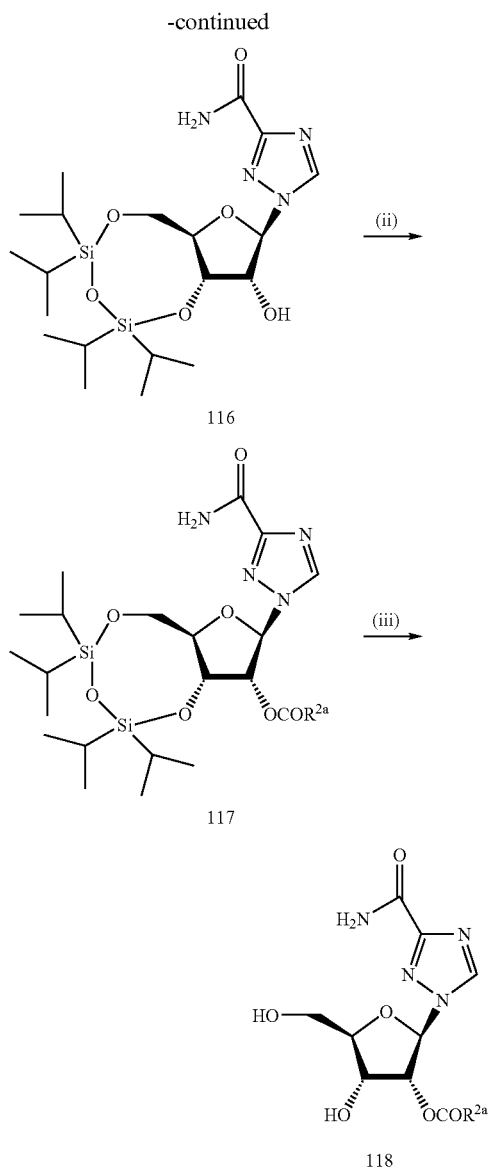
Reagents: (i) [(i-Pr)$_2$SiCl]$_2$O, imidazole, DMF;
(ii) R$^{2a}$COCl, base; or R$^{2a}$COOH, coupling reagent, base;
(iii) Bu$_4$NF, THF
Scheme III (2¢ and 3¢-Substitutions)
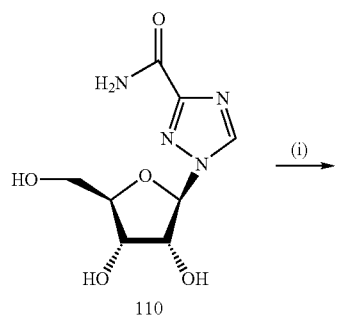
-continued
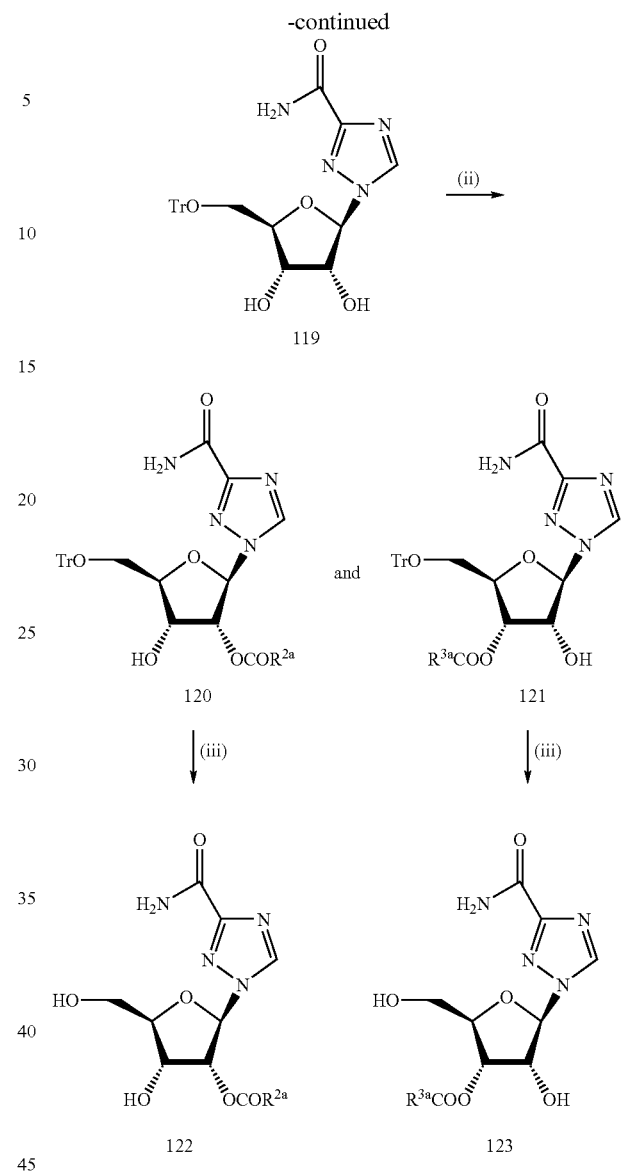
Reagents: (i) TrCl, base;
(ii) R$^{2a}$COCl, base; or R$^{2a}$COOH, base, coupling reagent;
(iii) TsOH, MeOH, H$_2$, Pd/C
Scheme IV (5′-Substitutions)
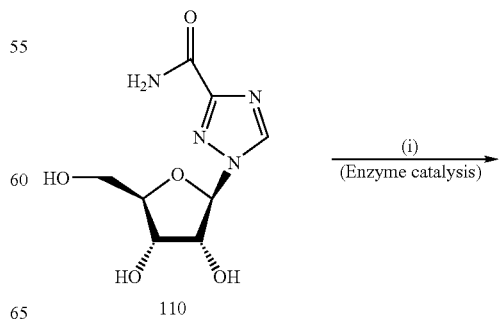

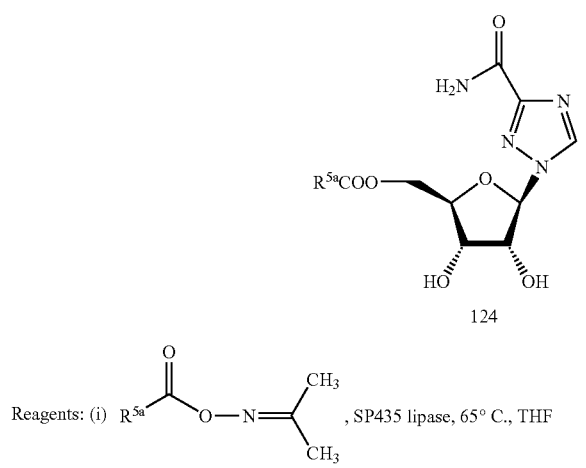
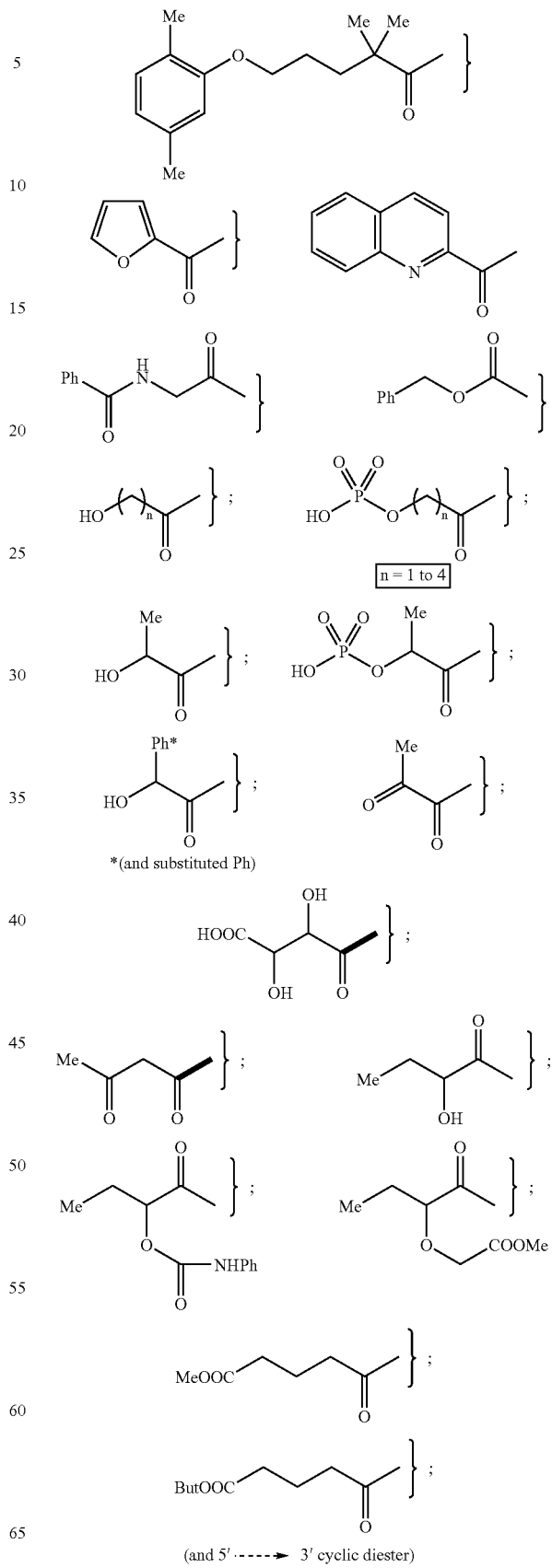
EXAMPLES FOR ALL SCHEMES
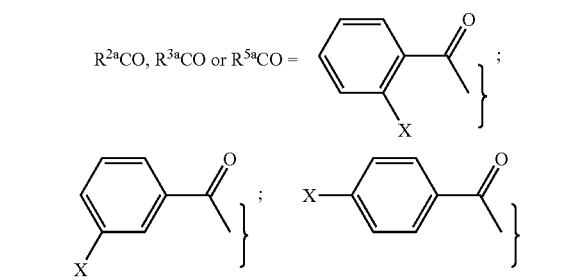
X = OH, OAc, COCH3, NH2, NHCOCH3, CH2OH, NHCbz, OMe, CN, NO2, F, Cl, Br, (C1–C6)alkyl, e.g. CH3, and disubstituted benzoates with a Combination of these group 'X'.
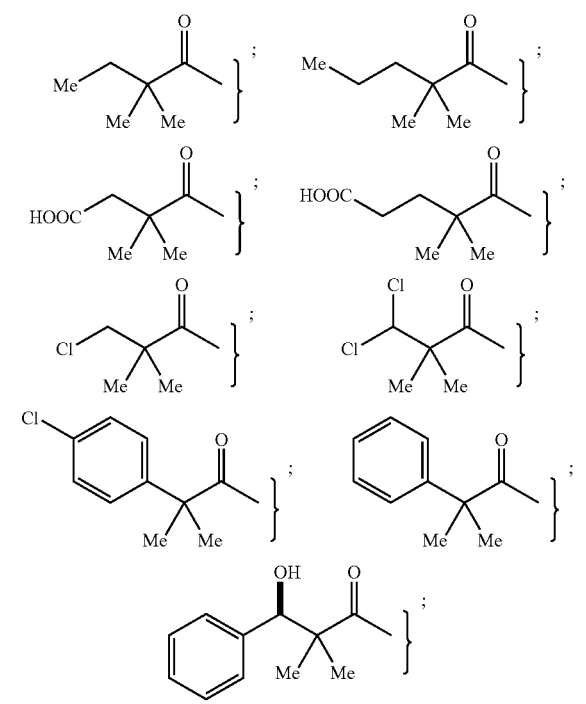

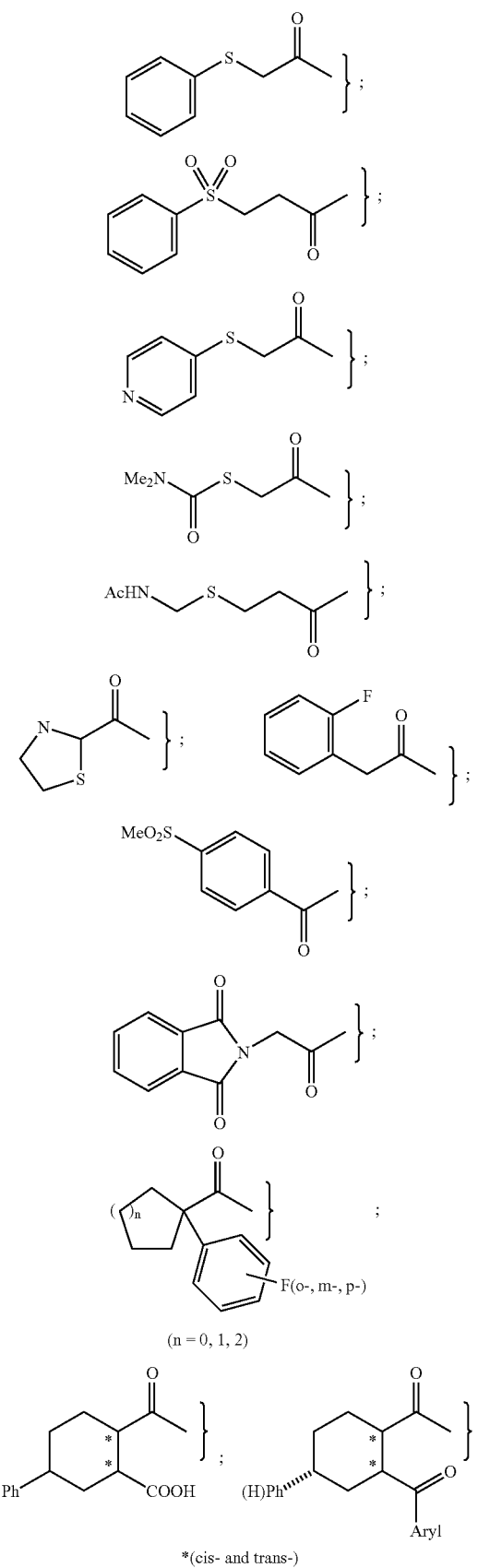
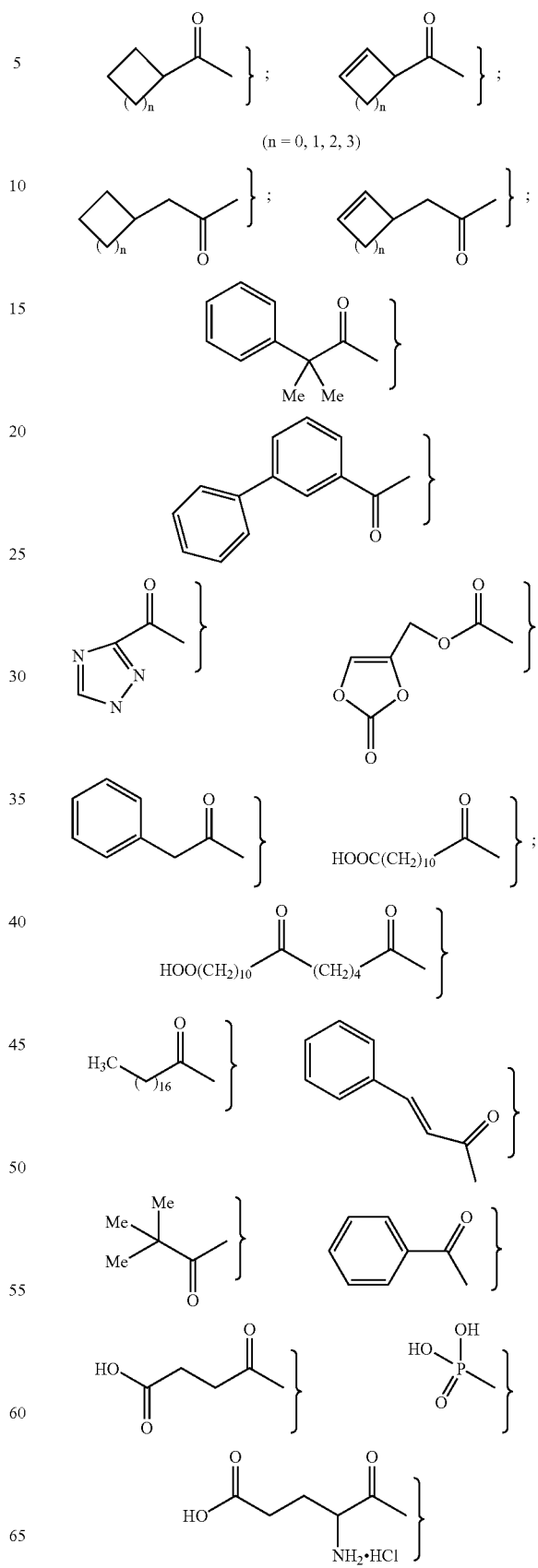

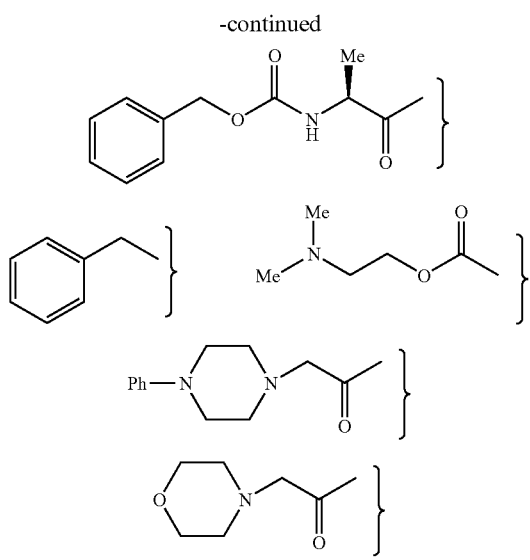

$R^{2a}CO$, $R^{3a}CO$, and $R^{5a}CO$ may also be represented by the formula:

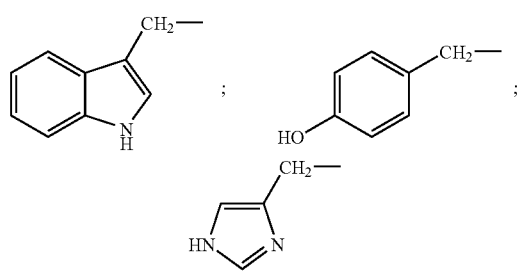

Y=H, $CH_3$; $CH_3CH_2-$; $CH_3CH_2CH_2-$; $Me_2CH-$; $Me_2CH_2CH_2-$; $CH_3CH_2CH(Me)-$ $PhCH_2-$; $HOOCCH_2CH_2-$; $HSCH_2-$; $HOOCCH_2-$; $MeSCH_2CH_2-$; $HOCH_2-$;

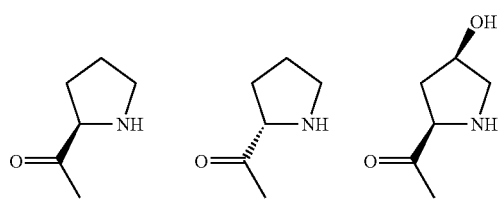

or Y is $H_2N(CH_2)_4-$ or $CH_3CH(OH)-$;
or Y taken together with the ox carbon and N form

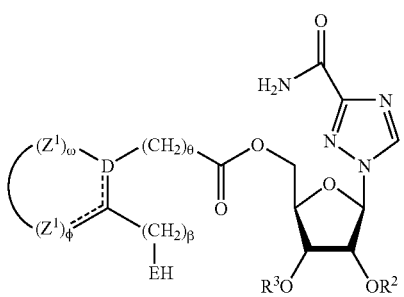

or a pharmaceutically acceptable salt thereof.

Examplary 5'-heteroaryl esters of Formulas I & II wherein $R^5=$

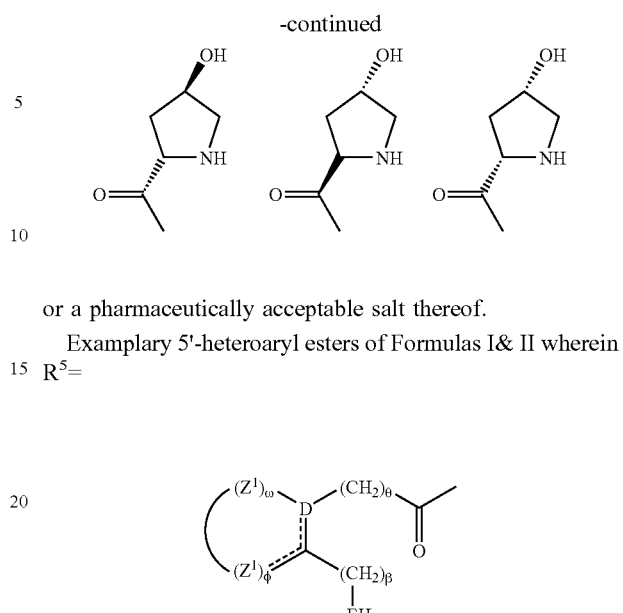

represents a heteroaryl ring of 5–7 total atoms at maximum unsaturation
wherein: D=C, or when θ>0 is N or S
E=O or NH
$Z^1$ and $Z^2$=independently —C(H)=, —C(H)=N—, —N=, —N(H)—, S, S—C(H)= or S—N=
θ and β=independently 0, 1, or
ω and φ independently 1, 2, or 3. The 5'-ester of formula is represented by the formula:

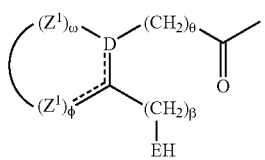

The following 5' esters may be prepared as described in Schemes hereinabive, using appropriately protected acids which are readily obtained by procedures well known to one skilled in the art.

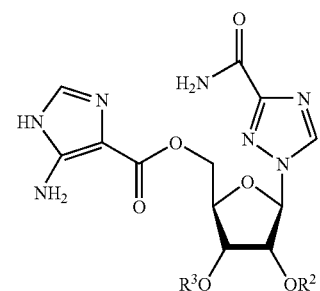

D = C, E = NH, Z¹ = ( —CH═N— ), ω = 1,
Z² = —NH—, φ = 0, and β = 0

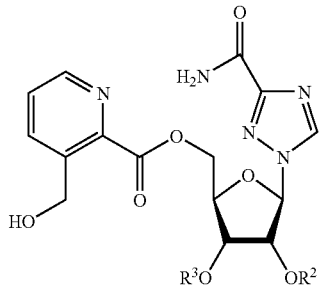

D = C, E = O, Z¹ = ( —CH═N— ), ω = 1,
Z² = —CH═, φ = 2, θ = 0, and β = 1

The following 5'-3' cyclic ester (Formula I wherin $R^2$=H) may be prepared using the Schemes herein above and readily available starting materials.

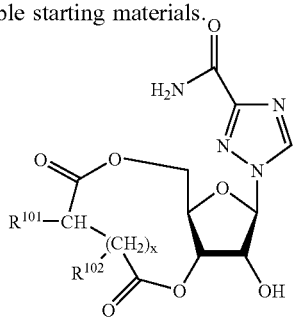

wherein $R^{101}$ and $R^{102}$ are
independently H,
alkanoyloxy, $OR^{7b}$ or $NR^6R^{7b}$ and
x=1 or 2

The following 3'-2' cyclic esters(formula I wherein $R^5$=H) may be made using the Schemes herein above and readily available starting materials.

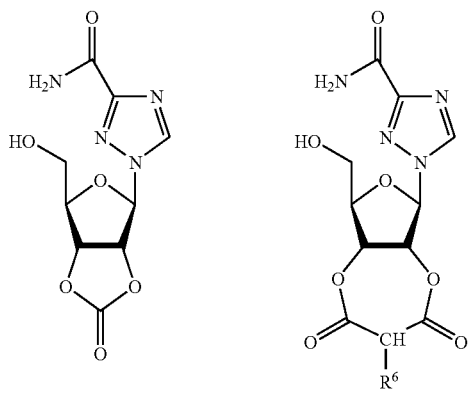

-continued

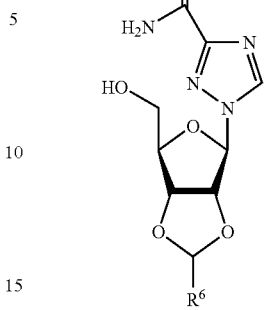 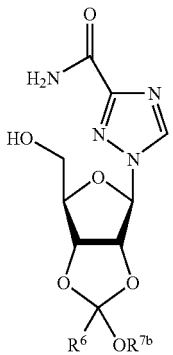

Example 1

A.

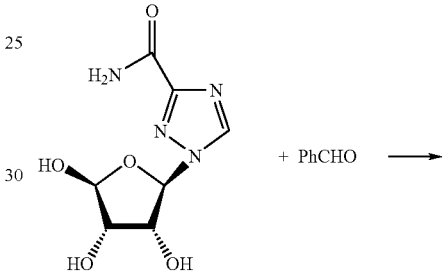

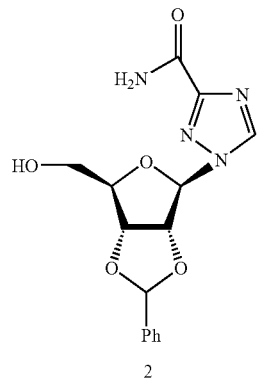

A. Benzylidene Ribavirin

Combine 20 g ribavirin (1, 87 mmol), 200 ml of benzaldehyde, and 20 g of $ZnCl_2$. Stir the so-formed reaction mixture at ambient temperature for 24 hours. Pour the resulting solution, with stirring, into 2.5 L of ethyl ether ($Et_2O$). Suction-filter the resulting mixture and dry the solid precipitate. Mix the solid precipitate with 1.2 L of ice-cold 2N sodium hydroxide (NaOH) solution. Extract the mixture with 2×0.75 L of cold ethyl acetate (EtOAc) and wash the organic layer with brine. Gravity-filter the organic layer through fluted filter paper, then concentrate it in vacuo to leave a solid. Triturate the solid thoroughly with 0.5 L of $Et_2O$, suction-filter and wash the so-formed preciptate with fresh $Et_2O$ to leave 23 g of compound 2 as a solid; Calc. for $C_{15}H_{16}N_4O_5$ (332.32). MS(FAB)=333.1.

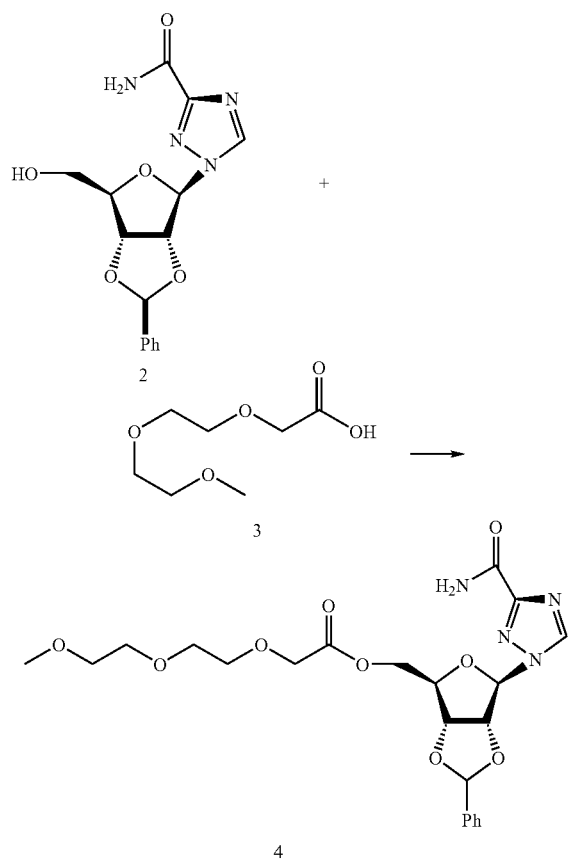

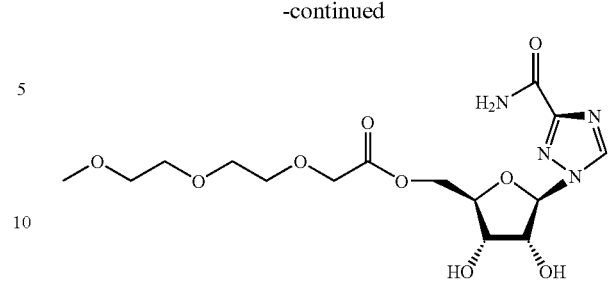

Combine 0.5 g (2.8 mmol) of compound 2 from step A, 0.80 g (2.4 mmol) of compound 4 [MeO(CH$_2$CH$_2$O)$_2$CH$_2$CO$_2$H] and 0.8 g (1.2 mmmol) of 4-(N,N,dimethylamino)pyridine (DMAP) in 15 ml of N,N,-dimethylformamide (DMF). Add 2.5 ml of a 1M solution of dicyclohexylcarbodiimide (DCC) in dichloromethane (CH$_2$Cl$_2$), and stir the resulting mixture at ambient temperature for 0.5 hour. Heat the so-formed reaction mixture at 100° C. for 1 hour. Quench the reaction mixture with aqueous 5% KH$_2$PO$_4$, and extract it with 2×100 ml of ethyl acetate (EtOAc). Wash the organic extract with 20 ml cold water, then with saturated brine. Gravity-filter the organic extract through fluted filter paper, then concentrate the filtrate in vacuo to leave a gum residue. Purify the residue by column chromatography (silica gel, gradient of 1% to 6% methanol-CH$_2$Cl$_2$) to give 0.48 g of compound 4; Calc. for C$_{22}$H$_{28}$N$_4$O$_9$ (492.49); MS(FAB)=493.1.

C. Treat 0.45 g 4 (0.91 mmol) with 10 ml of trifluoroacetic acid (TFA)-water (9:1 v/v) at ambient temperature for 0.5 hour. Quench with 30 ml xylene, then concentrate the so-formed mixture in vacuo to leave a gum. Triturate the gum with EtOAc, dilute with Et$_2$O, then suction-filter and dry the gum to leave 0.23 g of compound 5 as a solid, Calc. C$_{15}$H$_{24}$N$_4$O$_9$ (404.38); MS(FAB)=405.1.

Example 2

Follow the procedures of Example 1A and 1B except substitute an equivalent amount of the compound 6 (MeOCH$_2$CH$_2$OCHCO$_2$H) for compound 3 in step B to form compound 8. Follow the procedures of step C of Example 1 except substitute an equivalent amount of compound 7 for compound 4 to form the compound 8.

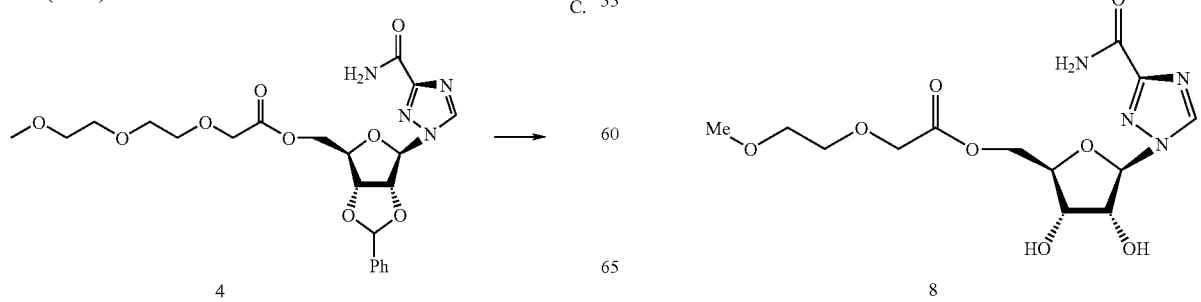

Example 3

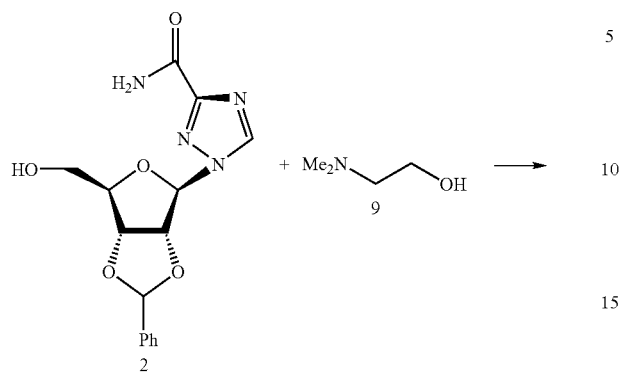

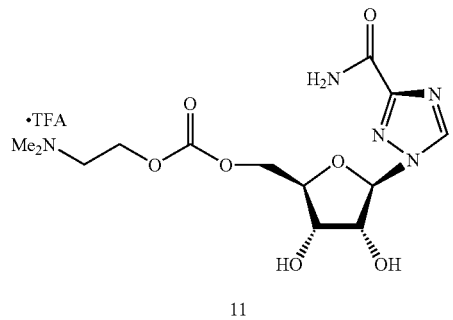

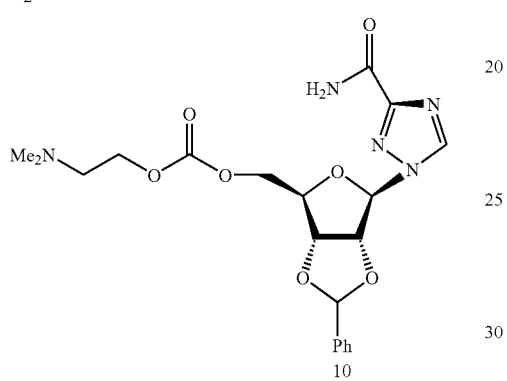

A. Treat a solution of 0.32 g (3.6 mmol) of compound 9 [2-(N,N'-dimethylamino)ethanol] in 10 mL of N,N,-dimethylformamide (DMF) at 5° C. with 0.58 g carbonyldiimidazole (3.6 mmol), and allow the so-formed solution to warm to 20° C. over 0.5 hr. Add to the resulting reaction mixture 0.8 g (2.4 mmol) of compound 2 prepared in accordance with Example 1A and stir the so-formed reaction mixture at ambient temperature for 24 hr. Concentrate the mixture in vacuo, add 50 mL of ethyl ether, and allow the so-formed mixture to set for 24 hr. Decant the supernatant solution, and purify the residue by column chromatography (silica gel, gradient of 10% to 20% methanol-tetrahydrofuran) to give 0.21 g of compound 10; calc. $C_{20}H_{25}N_5O_7$ (447.44). MS(FAB)=448.1.

B.

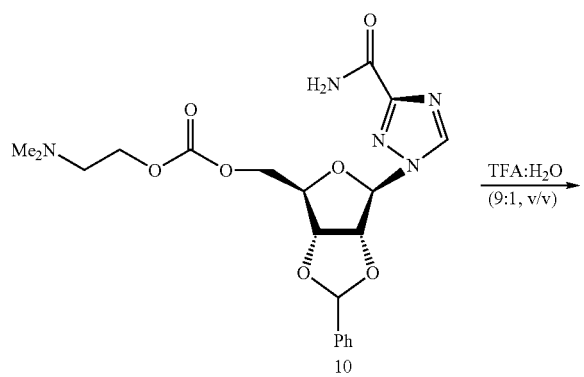

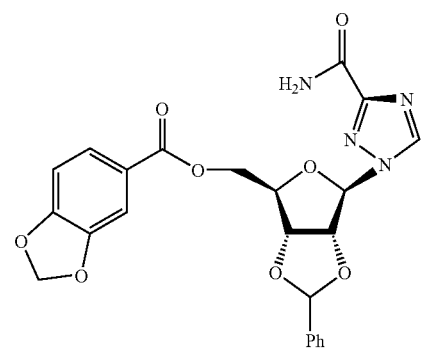

Follow the procedures of Example 1C except substitute an equivalent amount of compound 10 for compound 4 to obtain compound 11.

Example 4

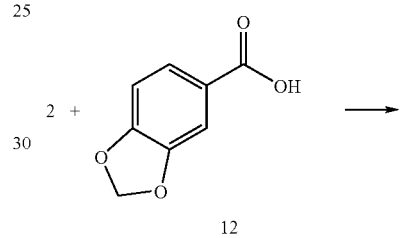

A stirred, dry DMF (5 mL) solution of 500 mg (1.506 mmol) of compound 2 prepared in accordance with the procedures of Example 1A, 300 mg (1.2 eq) of piperonylic acid (compound 12) was treated at ambient temperature with 732 mg (1.1 eq) of benzotriazolyloxytris-(dimethylamino) phosphonium hexafluorophosphate ("BOP reagent") and 576 µL (2.2 eq) of Hunig's base, i.e., -diisopropylethyl amine, [(i-Pr)$_2$NEt], under a nitrogen atmosphere. The so-formed reaction mixture was stirred overnight at ambient temperature. Thin layer chromatography (TLC) showed one major new spot. The reaction mixture was quenched with an aqueous NH$_4$Cl solution and diluted with EtOAc. The organic layer was washed with water and brine and then dried over Na$_2$SO$_4$. The organic solvent was evaporated to produce a crude purple solid. The crude solid was purified on a silica gel chromatography column with 2–3% MeOH/ CH$_2$Cl$_2$ as an eluent. The appropriate fractions were combined to give 550 mg of compound 13 as a purple-tinted solid (76% yield). The ¹H nmr spectrum (350 MHz in CDCl₃) was consistent with the structure of 13.

B.

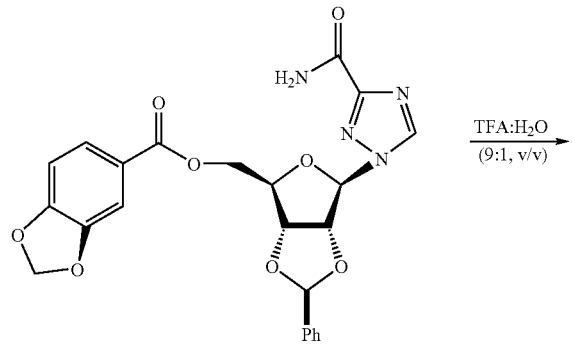

Compound 13 from step A was treated with 4 mL of TFA:H₂O (9:1, v/v) for 40 min. at ambient temperature. The solvents were evaporated to give a yellow solid. Water was added and evaporated. The crude solid was dried overnight. To the crude product was added 2×4 mL of MeOH. The MeOH layer was yellow. The insoluble material was collected and dried to give 342 mg of compound 14 as a white solid. The ¹H nmr spectrum was consistent with the structure of 14.

Example 5

A.

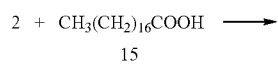

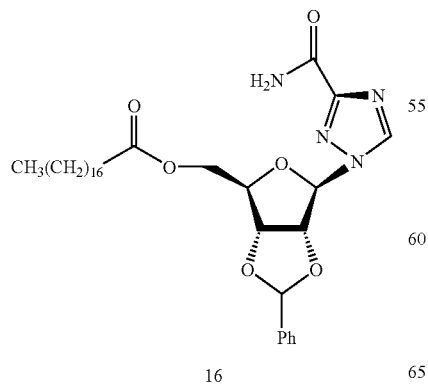

To a stirred solution of 500 mg (1.505 mmol) of 2 prepared in accordance with Example 1A in 3 mL of dry DMF at ambient temperature was added 516 mg (1.2 eq) of stearic acid (compound 15), 670 mg (1.0 eq) of the BOP reagent and 792 μL (3.0 eq) of Hunig's base. The so-formed reaction mixture was stirred overnight at ambient temperature. The reaction mixture was isolated in accordance with the procedures of Example 4A to give 595.5 mg of compound 16 as a viscous white solid (66% yield). The ¹H nmr spectrum was consistent with the structure of 16.

B.

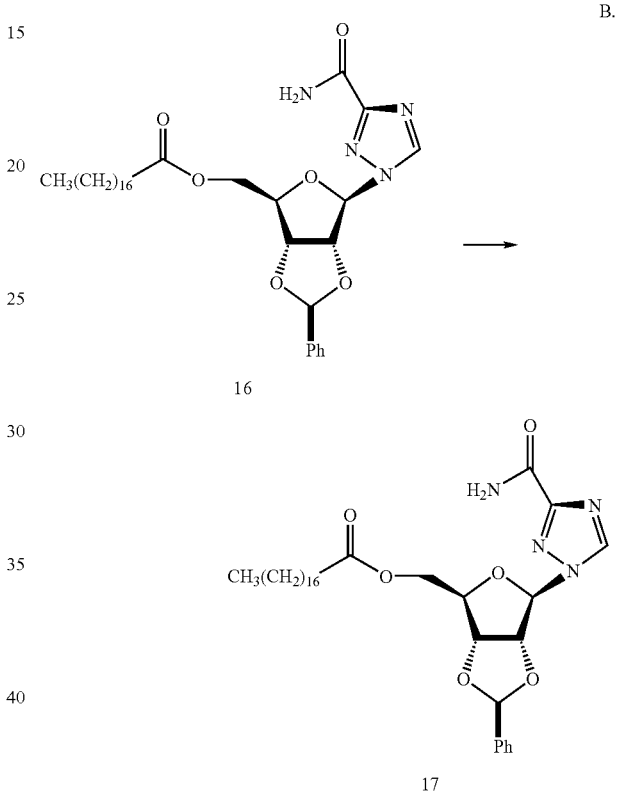

Compound 16 (417 mg, 0697 m mol) was treated in accordance with the procedures of Example 4B to give 330 mg of compound 17 as a white solid (93% yield). The ¹H nmr spectrum and MS-FAB were consistent with the structure of 17.

Example 6

A.

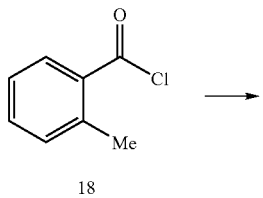

59

-continued

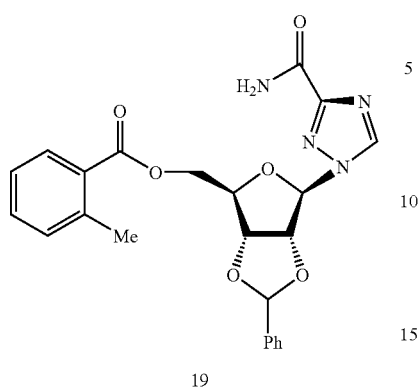

19

To a stirred suspension of 332 mg (1.0 mmol) of compound 2 prepared in accordance with Example 1A in 5 ml of dry $CH_2Cl_2$ was added 209 μL (1.5 eq) of triethylamine ($Et_3N$) and 167 μL (1.2 eq) of o-toluoyl chloride (compound 18). TLC showed completion of the reaction after the reaction mixture had been stirred at ambient temperature for 4 hours. The so-formed clear reaction mixture was diluted with EtOAc and quenched with water. The separated organic layer was washed with water and brine, dried and evaporated to give a crude white solid. The crude solid was purified on silica gel column chromatography elueting with 2–3% MeOH to give 262 mg of compound 19 as a white solid (57% yield).

B.

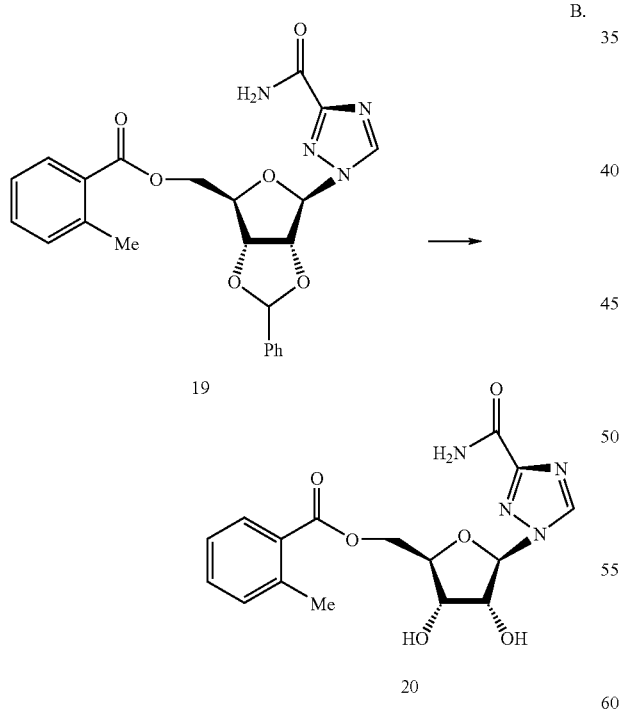

Compound 19 (262 mg) was treated with 3 mL of TFA:$H_2O$ (9:1 v/v) in accordance with the procedure of Example 4A to give 210 mg (99% yield) of the compound 20. The $^1H$ nmr spectrum was consistent with the structure of compound 20.

60

Example 7

A.

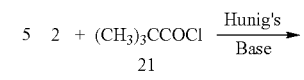

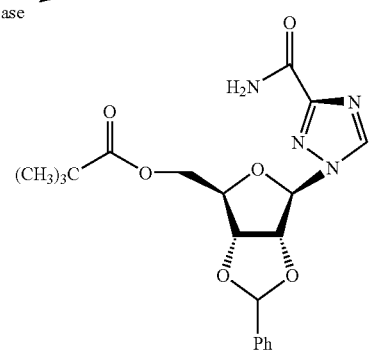

22

To a stirred suspension in a reaction flask immersed in an ice bath of 498 mg (1.5 m mol) of 2 prepared in accordance with Example 1A in 10 mL of dry $CH_2Cl_2$ was added 146 μL (1.80 mmol, 1.2 eq) of pyridine and 203 μL (1.65 mmol, 1.1 eq) of trimethylacetyl chloride (compound 21) at 0° C. The ice bath was removed after 5 min. Stirring was continued for 30 min. and 1 mL of DMF was added; the mixture changed from a suspension to a cloudy solution. By TLC, there was a substantial amount of unreacted starting material (compound 2). The reaction mixture was stirred overnight, and an additional amount of compound 21(203 μL,1.1 eq) and 180 mg (1.5 eq) of DMAP were added. The so-formed reaction mixture was stirred for 4 days at ambient temperature. There was still some unreacted starting material (compound 2) by TLC. The reaction mixture was worked-up by routine extraction between $H_2O$/EtOAc. The crude product was purified by silica gel column chromatography eluting with 2–5% MeOH/$CH_2Cl_2$ to give 411.3 mg of compound 22 (66% yield) as a white solid.

B.

Compound 22 (316 mg) was treated with 4 mL of TFA:H₂O (9:1 v/v) in accordance with the procedures of Example 4B to give 265 mg of compound 23.

Example 8

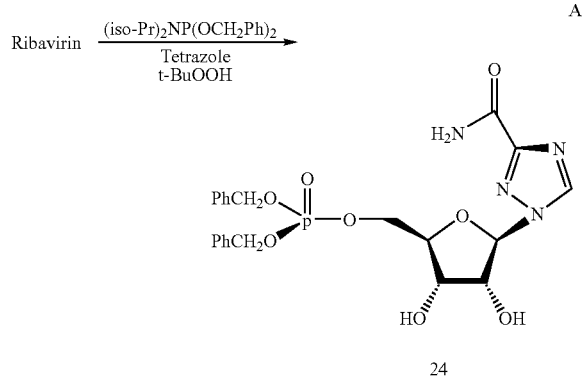

To a stirred mixture of 500 mg (2.1 m mol) of ribavirin and 2.07 g (1.04 mL, 1.5 eg, 3.1 mmol) of N,N-disopropyl-dibenzyl phosphoramide in 5 mL of DMF at room temperature, was added 433 mg (6.1 m mol, 3 eq) of tetrazole. The resulting reaction mixture was stirred at room temperature for 2 hrs., and then 1.11 mL (3 eq) of tert-butylperoxide (5.5M in decane) were added. The so-formed reaction mixture was stirred for 2 hrs. Water was added and the organic layer was washed, dried and evaporated to give a crude product. The crude product was purified on silica gel column chromatography using MeOH/CH₂Cl₂ as an eluent to give 493 mg of compound 24 as white solid. FAB:MS:MH⁺ =505.2.

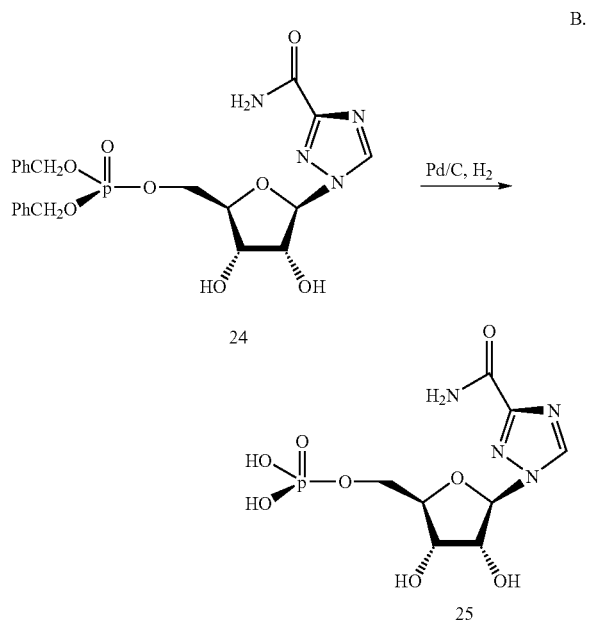

A suspension of compound 24 (278 mg) in a mixture of 3 mL of MeOH and 3 mL of water and 150 mg of 10% Pd on carbon was placed under an atmosphere of hydrogen for 4 hrs. The suspension was filtered through a pad of celite and the solid was washed thoroughly with MeOH. The combined filtrates were concentrated under reduced pressure to give 169.3 mg of the compound 25 as a white solid. FAB-MS, MH⁺=325.1

Example 9

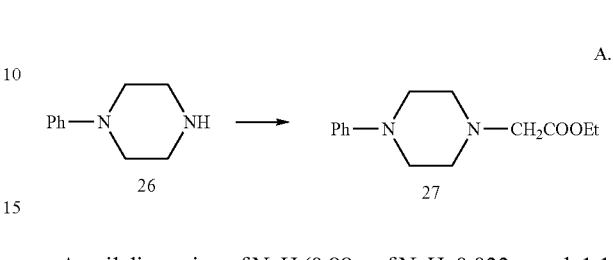

An oil dispersion of NaH (0.88 g of NaH, 0.022 mmol, 1.1 eq) was washed once with dry hexane and then suspended in 10 mL of dry THF. Compound 26 (N-phenylpiperazine, 3.24 g, 20 mmol) was added to the reaction vessel containing NaH in dry THF immersed in an ice bath The ice bath was removed and the so-formed reaction mixture was stirred for 1 hr. at room temperature. To the stirred white reaction mixture was added 2.66 mL (0.024 m mol, 1.2 eq) of ethyl bromoacetate. The so-formed reaction mixture was stirred overnight. The reaction mixture was cooled to ice bath temperature and quenched with an aqueous NH₄Cl solution. The so-formed mixture was extracted with EtOAc and the organic layer was washed with aqueous NH₄Cl brine and dried. The solvent was removed at reduced pressure to provide a crude product which was purified on a silica gel chromatography column using 20% EtOAc/hexane (v/v) as an eluent to provide 2.10 g of compound 27 (ethyl N-phenylpiperazinylacetic acid) as a clear oil. The ¹H nmr spectrum was consistent with the structure of compound 27.

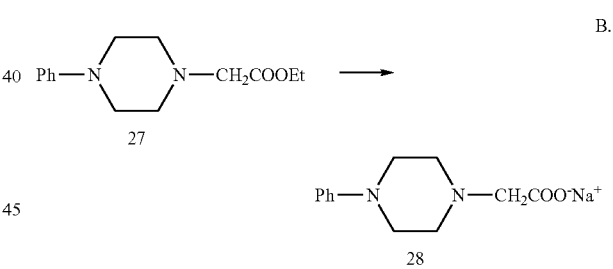

To a stirred solution of 2.10 g (8.47 m mol) of compound 27 in 8.47 mL of MeOH was added 8.47 mL (1.0 eq) of a 1 N NaOH solution. The so-formed reaction mixture was stirred for 3 hrs. at room temperature (no compound 27 was found by TLC). The solvents were removed under reduced pressure to provide a crude product. Water was added to the crude product and the solution was freeze dried overnight to provide 2.10 g of compound 28 as a white solid. The ¹H nmr spectrum was consistent with the structure of compound 28.

C.

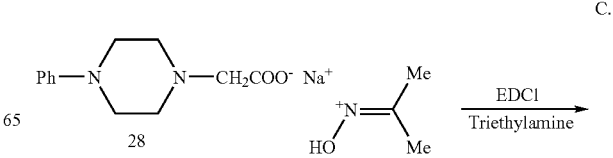

-continued

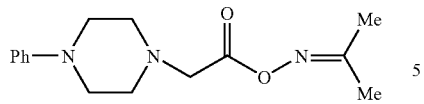

29

To a stirred solution of 1.21 g (5.0 m mol) of compound 28 in a mixture of 15 mL of CH₃CN and 5 mL of DMF was added 1.146 g (6.0 m mol, 1.2 eq) of EDC. HCl followed by 837 μL (6.0 m mol, 1.2 eq) of Et₃N and 731 mg (10.0 mmol, 2 eq) of acetone oxime (compound 28). The so-formed reaction mixture was stirred overnight and then diluted with EtOAc. The organic layer was washed with water and brine, dried and concentrated to give a crude product. The crude product was purified on silica gel column chromatography using 20% EtOAc/hexane (v/v) as an eluant to give 237 mg of compound 29 as a white solid. The 'H nmr spectrum of the oxime ester was consistent with the structure of compound 29.

D.

Ribavirin + 29 ⟶

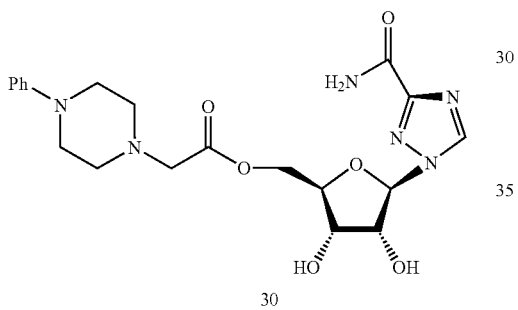

30

A suspension of 105.0 mg (0.431 m mol) of ribavirin 237 mg (0.862 m mol) of oxime ester 29 and 0.1 g of Novo SP435 lipase (*Candida antarctica*) in 5 mL of anhydrous THF was stirred at 65° C. for 24 hrs. The so-formed reaction mixture was cooled to room temperature, filtered and washed with MeOH. The crude material was purified on silica gel column chromatography using 10% MeOH/ CH₂Cl₂ (v/v) as eleunt to produce 66 mg of Compound 30 (a white solid) as a single product (in 42% yield). No other product was observed by TLC. The 'H nmr spectrum (300 MHz, DMSO-d₆) was consistent with the 5' ribavirin ester of structure 30.

Example 10

A.

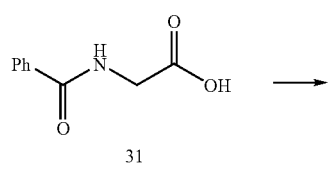

31

-continued

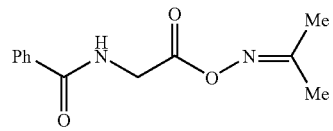

32

To a stirred solution of 2.45 g (1.4 mmol) of hippuric acid (compound 31) and 1.00 g (1.0 eq) of acetone oxime in 10 mL of CH₂Cl₂ at room temperature was added 2.83 g (1.0 eq) of DCC. The so-formed reaction mixture was stirred overnight and then filtered. The filtrate was concentrated under reduced pressure to produce a residue which was purified with EtOAc/hexane to give 2.36 g of the acetone oxime ester (32) as a colorless oil. The FAB-MS: MH⁺=235.1.

B.

Ribavirin + 32 ⟶

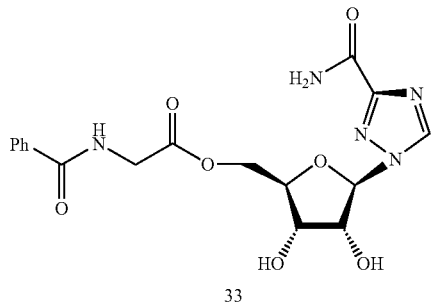

33

The procedure of Example 9, Step D was used except 2.13 g (9 mmol) of compound 32 was substituted for compound 29, 0.734 g (3 mmol, ⅓ eq) of ribavirin and 0.6 g of SP435 lipase were used in 25 ml of THF. The crude product was purified on silica gel column chromatography using CH₂Cl₂: MeOH (20:1, v/v) as an eluent to provide a crude product. The crude product was crystallized from MeOH: Et₂0 to provide 0.936 g of compound 33. FAB:MS, MH⁺=406.1.

Example 11

A.

Ribavirin + 34 ⟶

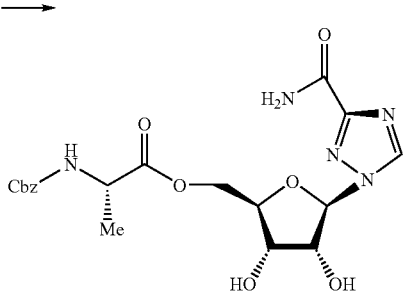

Compound 34, the acetone oxime ester of Cbz-L-alanine, was prepared in accordance with the procedures of F.Morris and V. Gotor, Tetrahedron, 1994, 50, 69–6934 at paragraph bridging 6932–6933. Then, the procedure of Example 10, Step B, was followed using 1.00 g (3.6 mmol) of compound 34 in place of compound 32, 0.294 g (1.2 mmol) of ribavirin, and 0.48 g of Novo SP435 lipase in 12 ml of THF. The crude produce was purified on silica gel column chromatography using CH$_2$Cl$_2$:MeOH (20:1, v/v) as an eluent to give 0.660 g of compound 35 as a white solid. The white solid was recrystallized from MeOH-EtOAc to give 0.532 g of compound 35.

C.

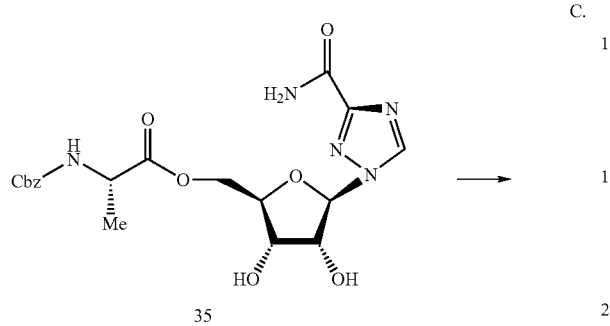

35

To a mixture of 0.100 g (0.222 mmol) of compound 35 and 42.3 mg (1 eq) of TSOH.H$_2$O in 3 ml of aqueous MEOH was added 50 mg of 10% Pd on carbon. The resulting black suspension was placed under a hydrogen atmosphere for 4 hours. The so-formed reaction mixture was filtered through a pad of celite and the solid was washed thoroughly with methanol. The combined filtrates were concentrated and the solvent removed to give 0.101 g of compound 36 as a white solid. FAB:MS MH$^+$=316.1.

Example 12

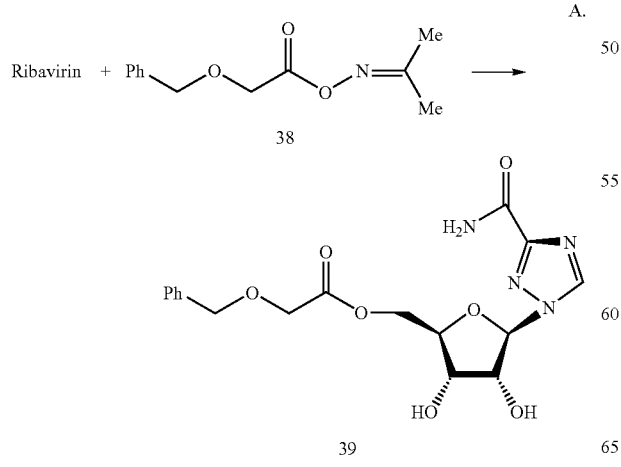

Compound 38 (PhCH$_2$OCH$_2$COO—N=C(CH$_3$)$_2$) was prepared from 2.17 ml (2.53 eq) benzyloxyacetylchloride (Compound 37) and 1.00 g of acetone oxine in 20 ml of CH$_2$Cl$_2$ containing 1.67 g (1 eq) of DMAP in accordance with the procedure of Example 10 Step A. Then, the procedure of Example 10, Step B was followed using 2.40 g (10.8 mmol) of compound 38 in place of compound 32 1.325 g (5.4 mmol) of ribavirin 2.18 g of Novo SP435 lipase in 70 ml of THF. The mixture was treated overnight at 70° C. under a nitrogen atmosphere. The crude product was purified on silica gel column chromatography using CH$_2$Cl$_2$:MeOH (10:1, v/v) as an eluent to provide 0.511 g of a mixture of two compounds. The desired compound 39 was purified by crystallization from MeOH:Et$_2$O to give 0.367 g of compound 39 as a white crystalline product.

B.

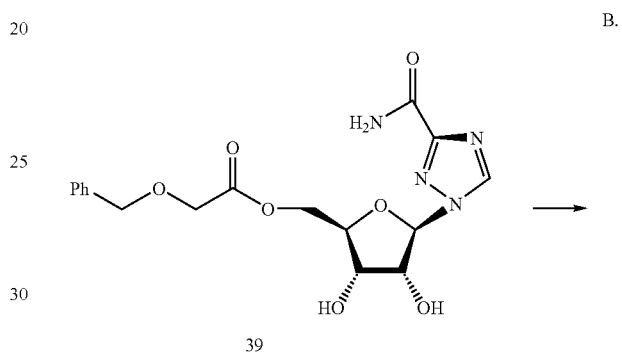

To a stirred suspension of 0.200 g of compound 39 in 5 ml of MeOH containing 50 mg of palladium black under an atmosphere of nitrogen was added 0.20 ml of formic acid. The resulting reaction mixture was heated to reflux for 1 hour. The resulting reaction mixture was cooled and filtered through a pad of cotton wool. The solids were thoroughly washed with methanol and then water. The combined filtrates were concentrated under reduced pressure to give a residue. Methanol was added to provide 99.2 mg of the compound 40. FAB-MS:MH$^+$=303.1.

Example 13

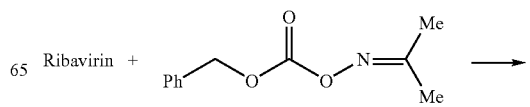

-continued

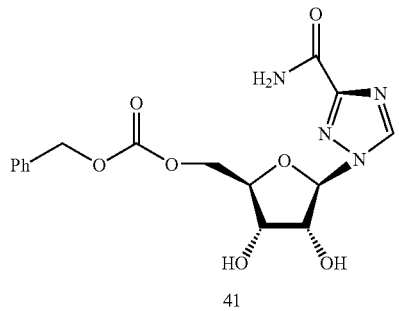

41

Compound 40 (PhCH₂OCOO—N=C(CH₃)) was prepared in accordance with the procedure of Step A of Example 10. Then the procedure of Step B of Example 10 as followed using 500 mg (2.4 mmol) of compound 40 in place of compound 32, 295 mg (1.2 mmol) of ribavirin, 160 mg of Novo SP435 in 15 ml of THF. The so-formed reaction mixture was heated at 70° C. for 3 days. The crude product dissolved in MeOH was purified on silica gel column chromatography using CH₂Cl₂:MeOH (20:1, v/v) as an eleunt to provide 156 mg of compound 41. FAB:MS, MH⁺=379.2.

Example 14

A. The benzyl ether of methyl-L-lactate (compound 42) was prepared from methyl-L-lactate in accordance with the procedures of U. Widner Synthesis 1987, 568.

B.

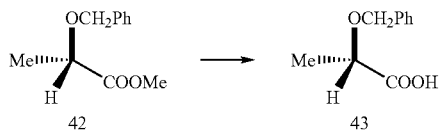

To a stirred solution of 1.00 g of compound 42 in a mixture of 9 ml of MeOH and 3 ml of water was added 216 mg (1 eq) of LiOH.H₂O. The so-formed reaction mixture was stirred for 4 hours. The resulting mixture was partitioned between CH₂Cl₂ and water. The aqueous phase was separated, washed with CH₂Cl₂ and acidified with excess 10% aqueous HCl. The organics were extracted with EtOAc. The EtOAc layer was dried and concentrated to give 779 mg of compound 43 as a colorless oil.

C.

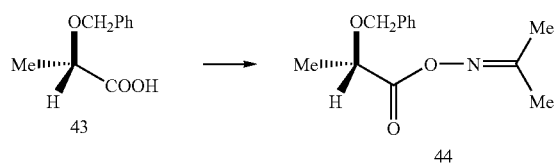

The procedures of Step A of Example 10 were followed using 1.15 g (6.39 mmol) of compound 43 in place of compound 31, 513 mg, (7.03 mmol, 1.1 eq) of acetone oxime, 1.45 g of DCC in 5 ml of CH₂Cl₂ to produce 1.20 g of the acetone oxime ester, compound 44.

D.

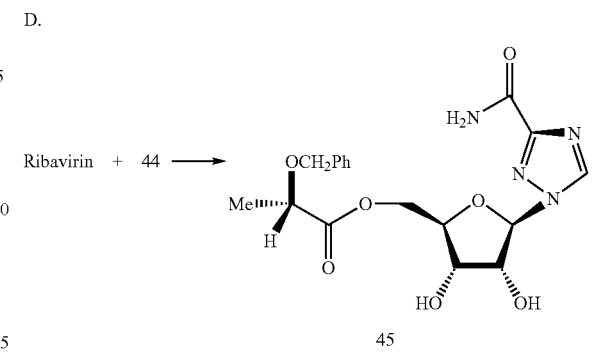

The procedure of Step B of Example 10 was followed using 1.2 g (5.1 mmol) of compound 44 in place of compound 32, 600 mg (2.5 mmol) of ribavirin and 500 mg of Novo SP435 lipase in 20 ml of THF. The mixture washed at 70° C. until no starting found by TLC.

The crude reaction product was purified by silica gel column chromatography using CH₂Cl₂:MeOH (20:1, v/v) to produce 183 mg of compound 45 as a white solid.

Example 15

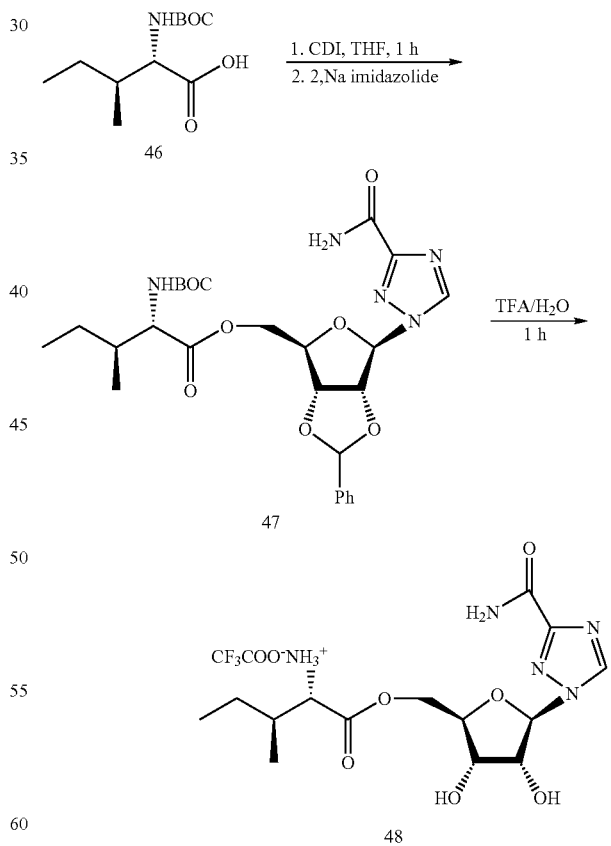

A solution of N-t-Boc-L-isoleucine (available fromSigma Chemical Co. St. Louis, Mo.) (1.270 g, 5.5 mmol) in anhydrous THF (30 mL) was treated with CDI, i.e., carbonyl-diimidazole (981 mg, 6.05 mmol) at room temperature for 1 hr. The compound 2 of Example 1 (1.660 g, 5.00 mmol)

and sodium imidazolide (150 mg, 1.5 mmol) were then added to the reaction mixture. This mixture was heated at 45° C. for 20 hrs. The reaction was diluted with EtOAc and quenched with aqueous NH₄Cl. The organic layer was washed with water three times and once with brine, and dried over Na₂SO₄ The dried organic layer was filtered and the filtrate was concentrated to give an off white solid which was purified on silica gel column chromatography (5–10% by volume of MeOH in CH₂Cl₂) to afford 1.244 g of compound 47.

Compound 47 was treated with trifluoroacetic acid (TFA)/water (9:1 v/v) at room temperature for 1 hr. All volatiles were evaporated. Water was added and evaporated again to afford 1.10 g of compound 48 as a soft solid. MS(FAB)=358 (MH⁺, 100%).

Example 16 evaporated. Water was added and evaporated again to afford the crude product which was purified on a silica gel column (10% by volume of MeOH in CH₂Cl₂) to afford 520 mg of compound 50 as a white solid.

A solution containing compound 50(140 mg, 0.219 mmol) and p-toluenesulfonic acid monohydrate, TsOH H₂O (83 mg, 0.438 mmol) was hydrogenated over 10% Pd/C (50 mg) under H₂ at a pressure of 1 atm for 4 hr. The catalyst was filtered off through a bed of Celite and washed with methanol-water. The filtrate was evaporated to afford 157 mg of compound 51 as a white powder. MS(FAB)=373 (MH⁺, 100%).

Example 17

Follow the procedures of Examples 11, 15 or 16 except substitute an equivalent amount of the Cbz- or Boc-D-amino

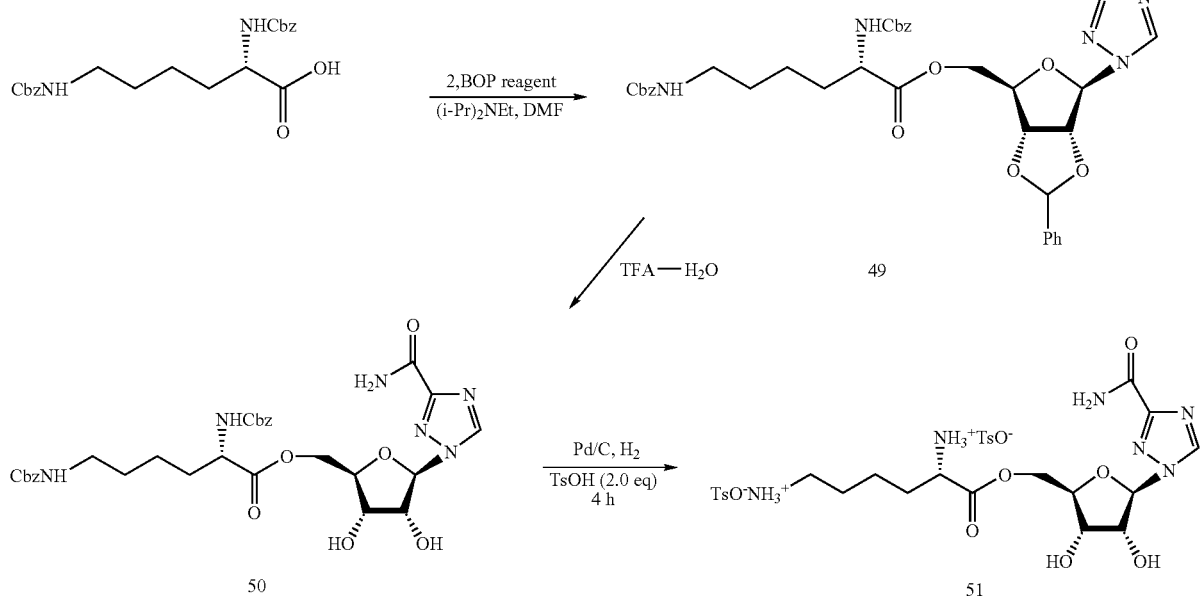

A solution of N,N-diCbz-L-lysine (available fromSigma Chemical Co. St. Louis, Mo.) (749 mg, 1.81 mmol) and compound 2 (500 mg, 1.506 mmol) in anhydrous DMF (5 mL) was treated with (732 mg, 1.66 mmol) of benzotriaz-olyloxytris-(dimethylamino)phosphonium hexafluorophosphate ("BOP reagent" available from Sigma Chemical Co. St. Louis, Mo.) followed by 576 mL, 3.31 mmol of Hunig's base, i.e., N,N-diisopropyl-ethyl amine, ["(i-Pr)₂NEt" available from Aldrich Chemical Co., Milwaukee, Wis.] under a nitrogen atmosphere at room temperature. The reaction mixture was stirred at room temperature overnight. The reaction mixture was diluted with EtOAc and quenched with aqueous NH₄Cl. The organic layer was washed three times with water, once with brine, and dried over Na₂SO₄ and. The dried organic layer was filtered and the filtrate was concentrated to give compound 49 as an off white solid.

Compound 49 was treated with trifluoroacetic acid/ water (9:1 v/v) at room temperature for 1 hr. All volatiles were acid derivative of the amino acid listed in the left hand column in the Table 3 below for the Boc-L-isoleucine used in Example 15, or the diCbz-L-lysine used in Example16, or the Cbz-L-alanine used in Example 11 to obtain the compounds of formula I or a pharmaceutical accepable salt thereof wherein the R is the moiety listed in the right hand column of the Table 4 below.

TABLE 4

| COLUMN A | COLUMN B |
|---|---|
| 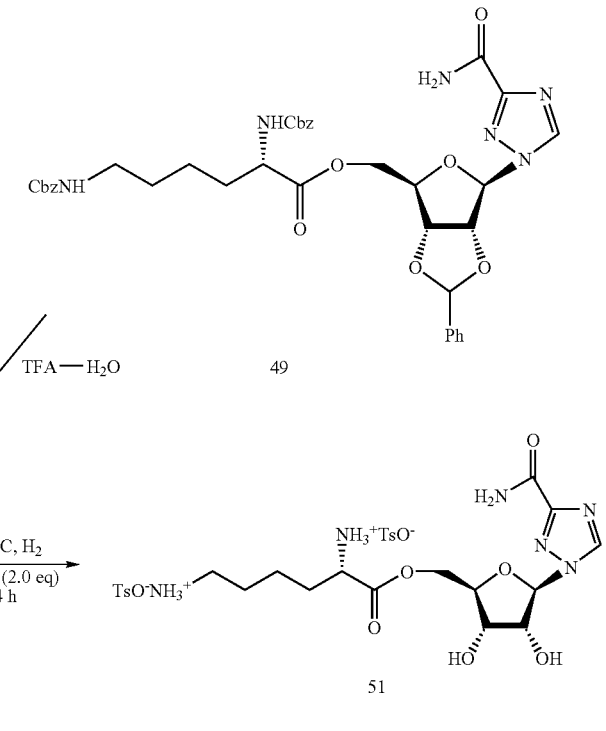 | |

TABLE 4-continued

| COLUMN A | COLUMN B |
|---|---|
| (alanine) | (alanine ketone) |
| (lysine) | (lysine ketone) |
| (lysine) | (lysine ketone) |
| (isoleucine) | (isoleucine ketone) |
| (isoleucine) | (isoleucine ketone) |
| (isoleucine) | (isoleucine ketone) |
| (isoleucine) | (isoleucine ketone) |
| (isoleucine) | (isoleucine ketone) |

TABLE 4-continued

| COLUMN A | COLUMN B |
|---|---|
| (arginine) | (arginine ketone) |
| (arginine) | (arginine ketone) |
| (aspartic acid) | (aspartic acid ketone) |
| (aspartic acid) | (aspartic acid ketone) |
| (asparagine) | (asparagine ketone) |
| (asparagine) | (asparagine ketone) |

TABLE 4-continued
| COLUMN A | COLUMN B |
|---|---|
| 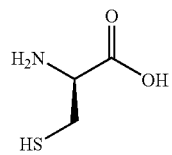 | 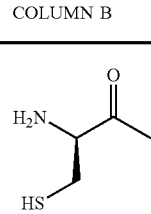 |
| 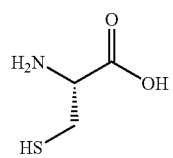 | 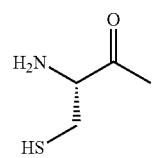 |
| 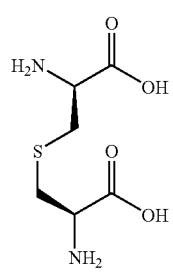 | 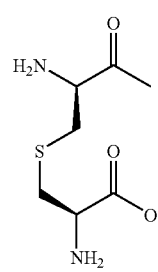 |
| 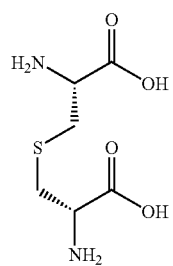 | 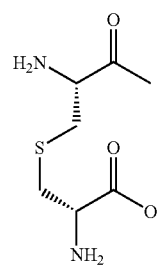 |
| 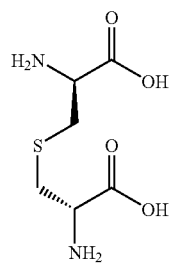 | 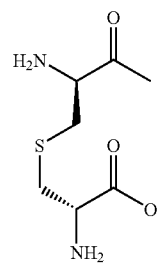 |
| 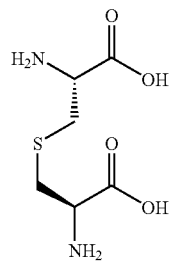 | 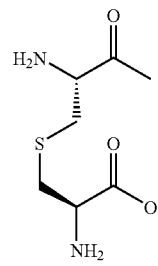 |
| 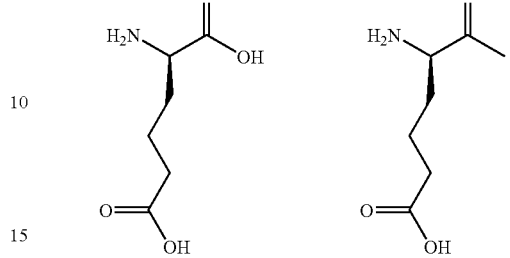 | |
| 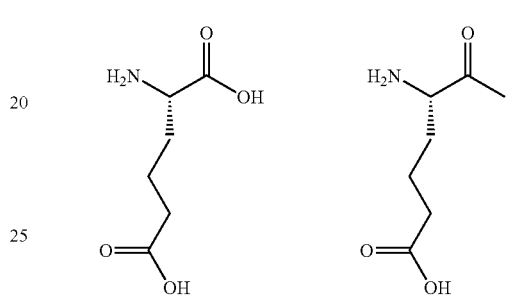 | |
| 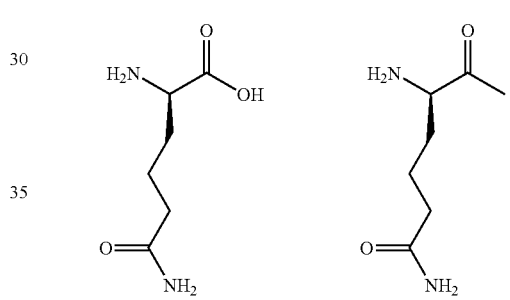 | |
| 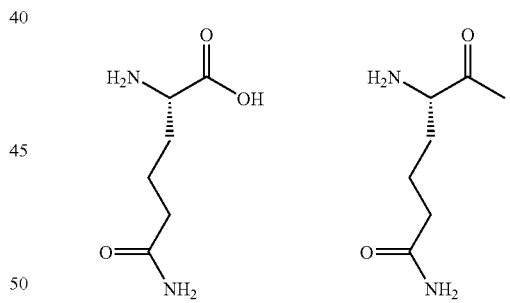 | |
| 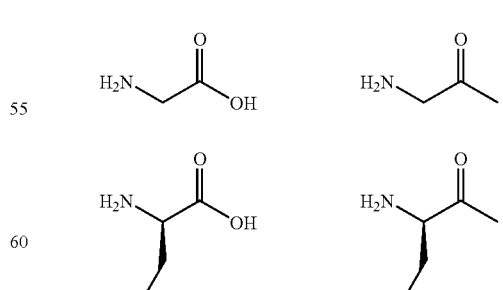 | |
|  | |

TABLE 4-continued
| COLUMN A | COLUMN B |
|---|---|
| 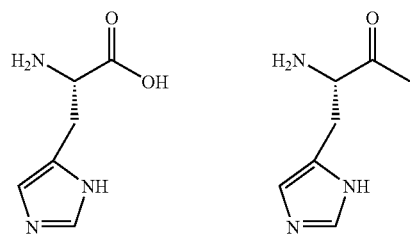 | 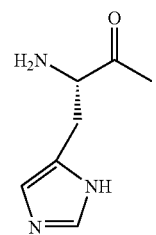 |
| 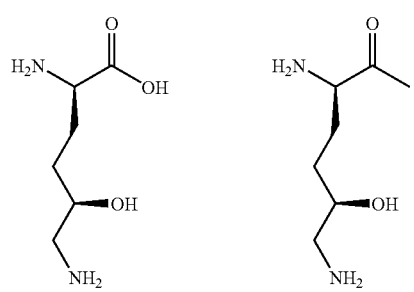 | 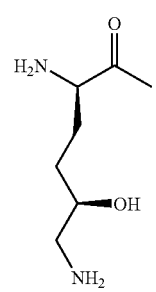 |
| 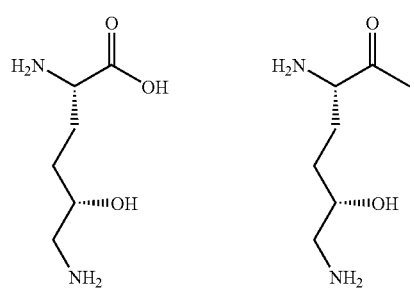 | 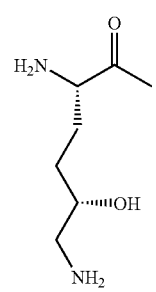 |
| 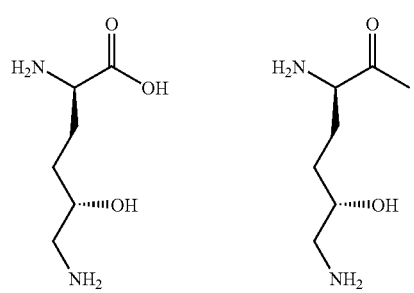 | 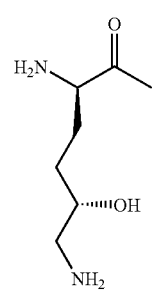 |
| 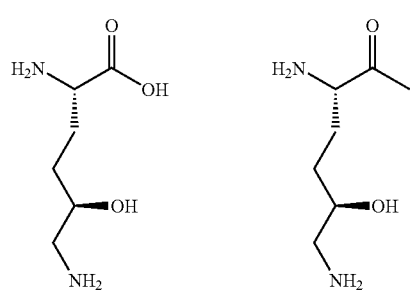 | 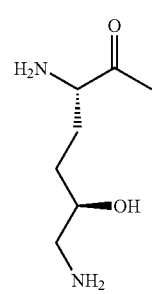 |
TABLE 4-continued
| COLUMN A | COLUMN B |
|---|---|
| 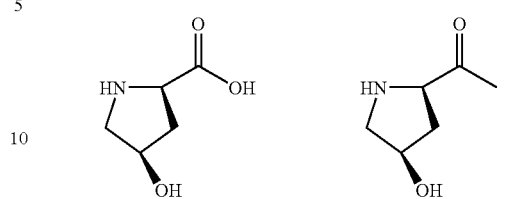 | 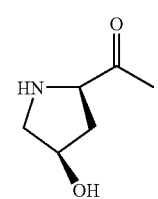 |
| 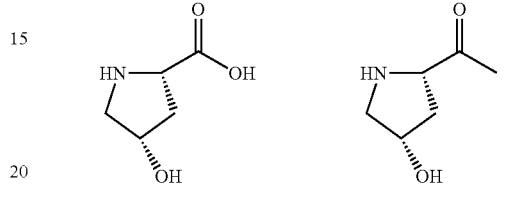 | 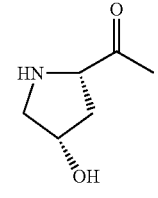 |
| 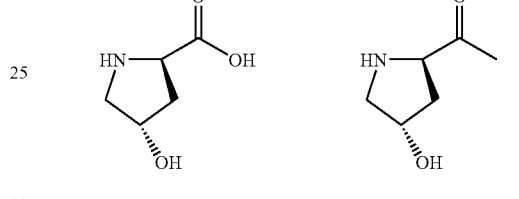 | 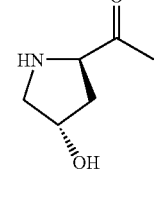 |
| 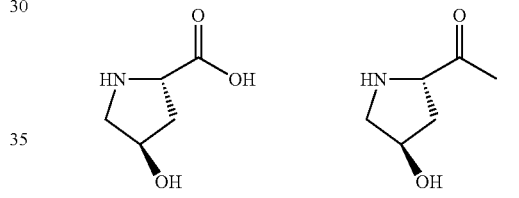 | 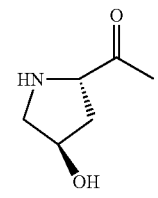 |
| 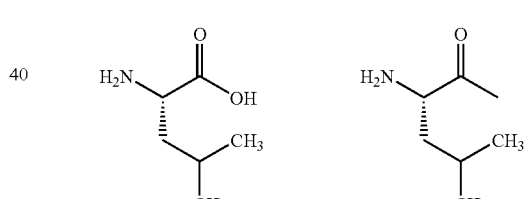 | 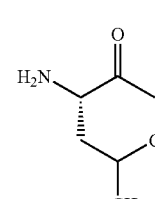 |
| 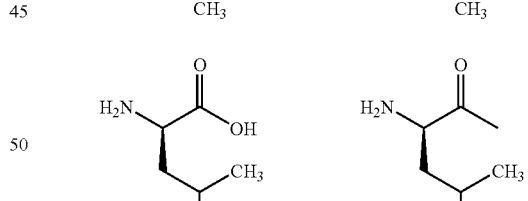 | 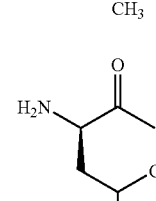 |
| 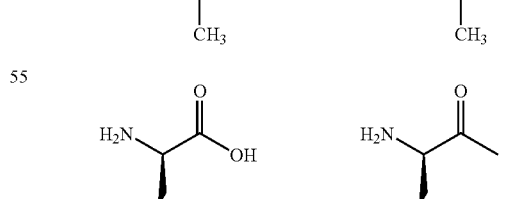 | 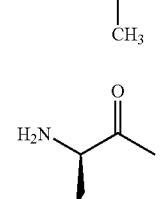 |

TABLE 4-continued
| COLUMN A | COLUMN B |
|---|---|
| 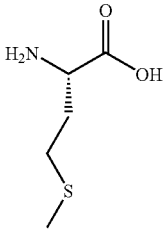 | 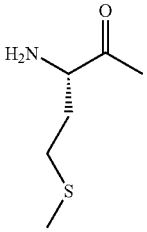 |
| 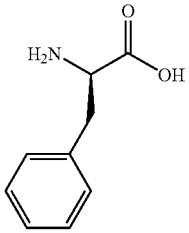 | 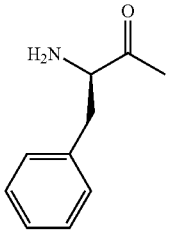 |
| 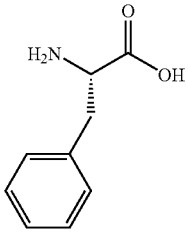 | 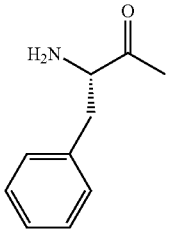 |
| 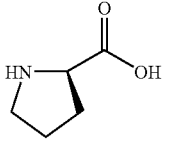 | 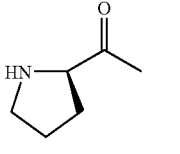 |
| 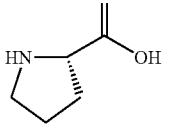 | 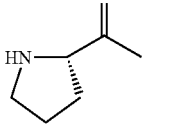 |
| 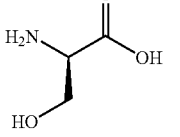 | 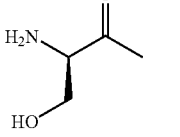 |
| 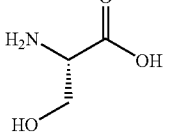 | 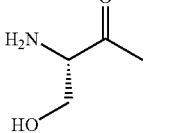 |
| 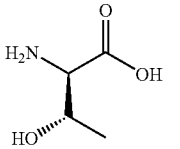 | 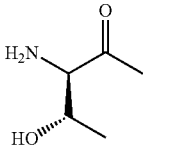 |
TABLE 4-continued
| COLUMN A | COLUMN B |
|---|---|
| 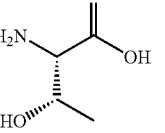 | 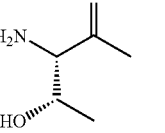 |
| 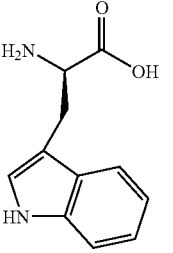 | 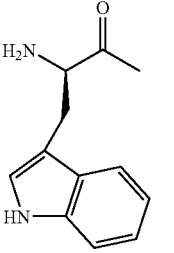 |
| 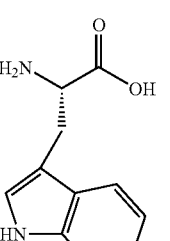 | 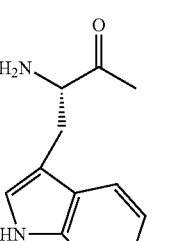 |
| 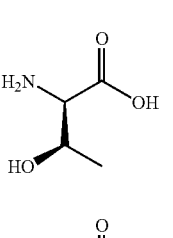 | 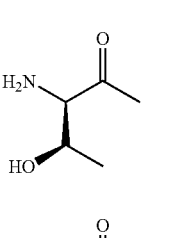 |
| 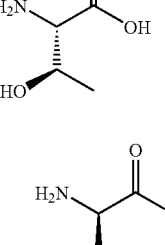 | 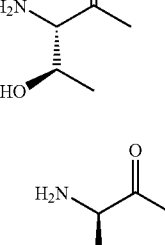 |
| 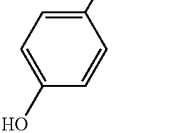 | 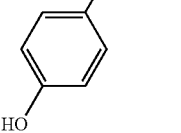 |

TABLE 4-continued
| COLUMN A | COLUMN B |
|---|---|
| 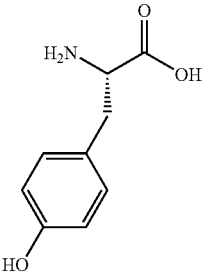 | 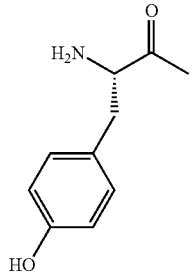 |
| 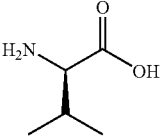 | 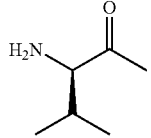 |
| 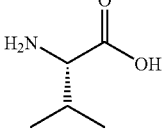 | 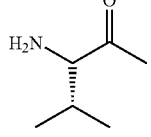 |
| 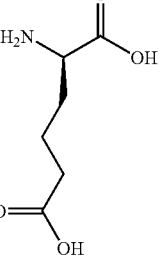 | 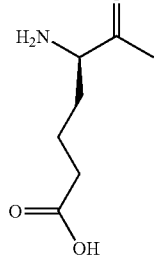 |
| 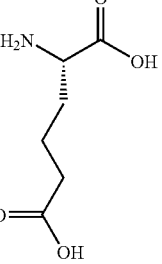 | 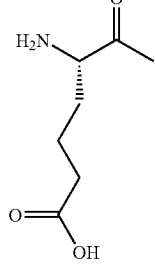 |
| 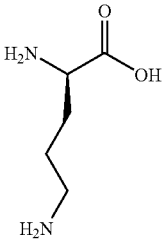 | 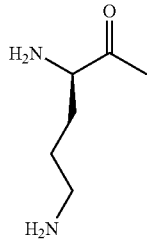 |
| 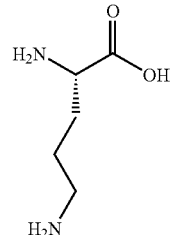 | 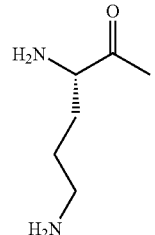 |
| 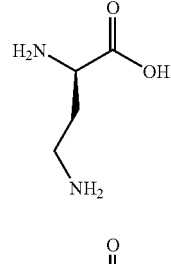 | 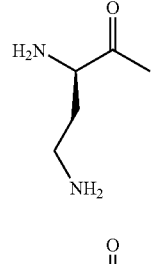 |
| 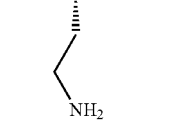 | 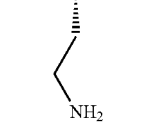 |
| 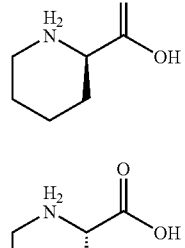 | 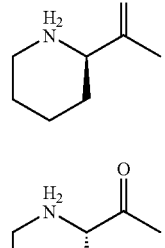 |
| 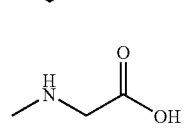 | 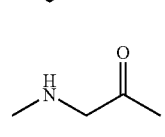 |
| 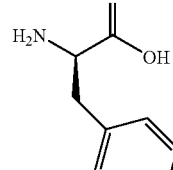 | 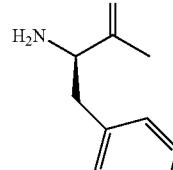 |
| 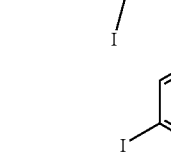 | 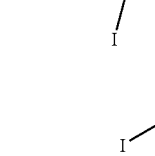 |
|  |  |

TABLE 4-continued

| COLUMN A | COLUMN B |
|---|---|

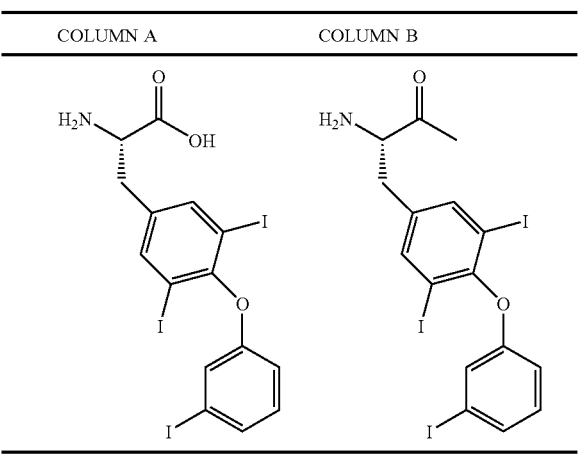

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A compound represented by formula V

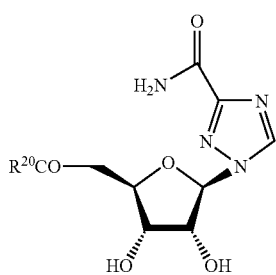

V wherein $R^{20}CO-$ is a natural or unnatural amino acid moiety represented by the formulas

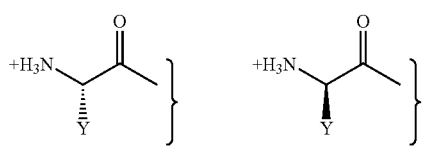

Y=H, CH₃; CH₃CH₂—; CH₃CH₂CH₂—; Me₂CH—; Me₂CH₂CH₂—; CH₃CH₂CH(Me)—PhCH₂—; HOOCCH₂CH₂—; HSCH₂—; HOOCCH₂—; MeSCH₂CH₂—; HOCH₂—;

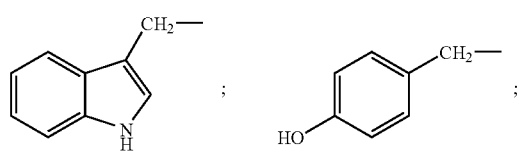

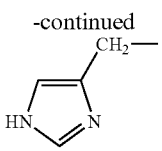

or Y is H₂N(CH₂)₄— or CH₃CH(OH)—; or a pharmaceutically acceptable salt thereof;
or Y taken together with the α carbon and N form

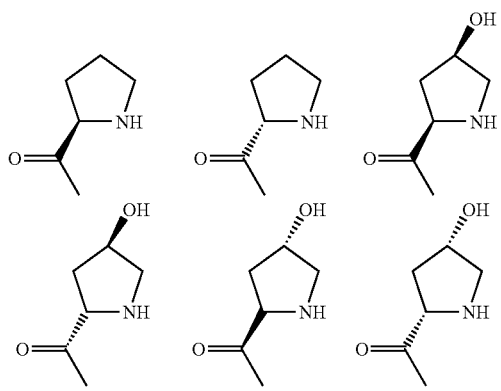

or a phamaceutically acceptable salt thereof;
or Y taken together with the α carbon and N form

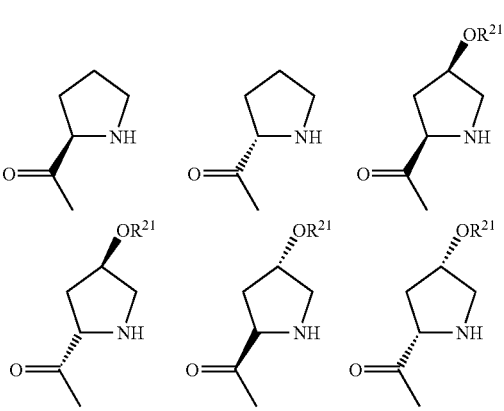

or a phamaceutically acceptable salt thereof,
and wherein $R^{21}$ is H, alkyl, alkanoyl, or aryl, or is alkyl, alkanoyl or aryl substituted by halo, phenyl, CN, NO₂OH, CO₂H or alkoxy.

2. A pharmaceutical composition of a compound of claim 1 or a pharmaceutically acceptable salt thereof together with a pharmaceutically acceptable carrier.

3. A method of treating a patient having a susceptible viral infection, wherein the method comprises administering to the patient a therapeutically effective amount of a ribavirin derivative of formula V of claim 1 or a pharmaceutically acceptable salt thereof, and wherein the susceptible viral infection is a flavivirus, a pestivirus, a hepavirus, an arbovirus, an orthomyxovirus, a poaramyxovirus, an arenavirus, a bunyavirus, a herpes virus, an adenovirus, a poxvirus, or a retrovirus.

4. A method of treating a patient having a chronic hepatitis C viral infection, wherein the method comprises administering to the patient a therapeutically effective amount of a ribavirin derivative of formula V of claim 1 or a pharmaceutically acceptable salt thereof and a therapeutically effective amount of an interferon alpha.

5. The method of claim 4, wherein the interferon alpha is selected from interferon alpha-2a, Interferon alpha-2b, a consensus interferon, a purified interferon alpha product or a pegylated interferon alpha-2a, pegylated interferon alpha-2b, and pegylated consensus interferon.

6. The method of claim 4, wherein the interferon alpha is a pegylated interferon alpha-2b and the amount of pegylated interferon alpha-2b is from 0.5 to 2.0 micrograms/kilogram per week on a weekly, three times a week, every other day or daily basis.

7. The method of claim 4, wherein the interferon alpha is a pegylated interferon alpha-2a and the amount of pegylated interferon alpha-2a administered is from 20 to 250 mlcrograms/kilogrenl per week on a weekly, three times a week, every affier day or daily basis.

* * * * *

UNITED STATES PATENT AND TRADEMARK OFFICE
CERTIFICATE OF CORRECTION

PATENT NO.        : 7,115,578 B2
APPLICATION NO. : 10/885374
DATED             : October 3, 2006
INVENTOR(S)       : Ashit K. Ganguly It is certified that error appears in the above-identified patent and that said Letters Patent is hereby corrected as shown below:

Claim 1, column 81, line 45: delete "$R^{20}CO$-" and insert -- $R^{20}C$- --;

Claim 3, column 82, line 63: delete "poaramyxovirus" and insert --paramyxovirus--;

Claim 5, column 83, line 6: delete "Interferon" and insert --interferon--;

Claim 7, column 84, lines 7-8: delete "mlcrograms/kilogrenl" and insert --micrograms/kilogram--; line 9: delete "affier" and insert --other--.

Signed and Sealed this

First Day of May, 2007

JON W. DUDAS
*Director of the United States Patent and Trademark Office*